US006987004B1

(12) United States Patent
Kawasaki et al.

(10) Patent No.: US 6,987,004 B1
(45) Date of Patent: Jan. 17, 2006

(54) GENES INTEGRATING SIGNAL TRANSDUCTION PATHWAYS

(75) Inventors: Hiroaki Kawasaki, Higashi-Ku (JP); Ann Graybiel, Lincoln, MA (US); David Housman, Newton, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/422,999

(22) Filed: Oct. 22, 1999

Related U.S. Application Data

(60) Provisional application No. 60/108,685, filed on Nov. 16, 1998, provisional application No. 60/105,507, filed on Oct. 23, 1998.

(51) Int. Cl.
*C12N 15/12* (2006.01)
*C12N 15/63* (2006.01)
*C12N 15/00* (2006.01)
*C07H 21/04* (2006.01)

(52) U.S. Cl. .................. 435/69.1; 435/320.1; 435/325; 536/23.5

(58) Field of Classification Search ............... 536/23.5; 435/69.1, 320.1, 325
See application file for complete search history.

(56) References Cited

U.S. PATENT DOCUMENTS

| 4,618,598 A | 10/1986 | Conn |
| 4,959,313 A * | 9/1990 | Taketo ........................ 435/69.1 |
| 5,874,464 A | 2/1999 | Marquez et al. |

FOREIGN PATENT DOCUMENTS

| WO | WO 91/15515 | 10/1991 |
| WO | WO 98/53061 | 11/1998 |

OTHER PUBLICATIONS

Eck, S.L. and Wilson, J. M. "Gene Based Therapy" in The Pharmacological Basis of Therapeutics, McGraw-Hill. 1996, pp. 77-101.*
Bonaldo et al. Normalization and subtraction: two approaches to facilitate gene discovery. Genome research. 1996. vol. 6(9) 791-806.*
Mehta et al. Identification of a Novel cis-Acting Element Participating in Maximal Induction of the Human Low Density Lipoprotein Receptor Gene Transcription in Response to Low Cellular Cholesterol Levels. Jpurnal of Biological Chemistry. vol. 271, No. 52.*
Voet et al. Biochemistry. 1990. John Wiley and Sons, Inc. pp. 126-128 and 228-334.*
Moreadith RW et al. Gene targeting in embryonic stem cells: the new physiology and metabolism. J Mol Med. Mar. 1997;75(3):208-16.*
Seamark RF. et al. Progress and emerging problems in livestock transgenesis: a summary perspective. Reprod Fertil Dev. 1994;6(5):653-7.*
Mullins LJ et al. Transgenesis in the rat and larger mammals. J Clin Invest. Apr. 1, 1996;97(7):1557-60.*
Aklilu, F. et al.: "Induction of Parathyroid Hormone-related Peptide by the Ras Oncogene: Rose of Ras Farnesylation Inhibitors as Potential Therapeutic Agents for Hypercalcemia of Malignancy," *Cancer Research* (Oct. 1997) v. 57, pp. 4517-4522.
Anderson, K.D. et al.: "Ciliary Neurotropic Factor Protects Striatal Output Neurons in an Animal Model of Huntington Disease," *Proc. Natl. Acad. Sci.* (Jul. 1996) v. 93, pp. 7346-7351.
Bailey, C.H. et al.: "Toward a Molecular Definition of Long-Term Memory Storage," *Proc. Natl. Acad. Sci* (Nov. 1996) v. 93, pp. 13445-13452.
Boguski, M.S. et al.: "Proteins Regulating Ras and its Relatives," *Nature* (Dec. 1993) v. 366, pp. 643-654.
Bos, J.L. et al.: "In Search of a Function for the Ras-Like GTPase Rap1" *FEBS* (Mar. 1997) v. 410 pp. 59-62.
Burgering, B.M.T. et al.: "Regulation of Ras-Mediated Signalling: More Than One Way to Skin a Cat," *TIBS*, (Jan. 1995) v.20, pp. 18-22.
Campbell, S.L. et al.: "Increasing Complexity of Ras Signaling" *Oncogene*, (1998) v. 47, pp. 4395-1413.
Chen, et al.: "A Synaptic Ras-GTPase Activating Protein (p135 SynGAP) Inhibited by CaM Kinase II," *Neuron* (May 1998) v.20, pp. 895-904.
Ebinu, J.O. et al.: "RasGRP, a Ras Guanyl Nucleotide-Releasing Protein with Calcium- and Diacylglycerol-Binding Motifs." *Science*, (May 15, 1998) v. 280, pp. 1082-1086, XP000882708.
Fiorillo, C.D. et al.: "Glutamate Mediates an Inhibitory Postsynaptic Potential in Dopamine Neurons" *Nature* (Jul. 1998) v. 394, pp. 78-82.
Fotuhi, M. et al.: "Phosphoinositide Second Messenger System is Enriched in Striosomes: Immunohistochemical Demonstration of Inositol 1, 4, 5-Trisphosphate Receptors and Phospholipase C β and γ in Primate Basal Ganglia" *The Journal of Neuroscience* (Aug. 1993) v. 13, No. 8, pp. 3300-3308.

(Continued)

*Primary Examiner*—Joseph Murphy
(74) *Attorney, Agent, or Firm*—Kirkpatrick & Lockhart Nicholson Graham LLP

(57) ABSTRACT

The present invention describes the identification, isolation, sequencing and characterization of two human CalDAG-GEF, and two human cAMP-GEF genes, which are associated with the Ras pathway. Also identified are CalDAG-GEF gene homologues in mice and cAMP-GEF gene homologues in rats. Nucleic acids and proteins comprising or derived from the CalDAG-GEFs and/or cAMP-GEFs are useful in screening and diagnosing certain Ras-associated cancers, in identifying and developing therapeutics for treatment of certain Ras-associated cancers, and in producing cell lines and transgenic animals useful as models of Ras-associated cancers.

18 Claims, 12 Drawing Sheets

OTHER PUBLICATIONS

Franke, B. et al.: "Rapid $Ca^{2+}$-Mediated Activation of Rap1 in Human Platelets" *The EMBO Journal* (1997) v. 16, No. 2, pp. 252-259.

Gotoh, T. et al.: "Identification of Rap1 as a Target for the Crk SH3 Domain-Binding Guanine Nucleotide-Releasing Factor C3G." *Molecular and Cellular Biology*, (1995) v. 15, pp.. 6746-6753, XP000881340.

Heizman, C.W.: "Calcium-Binding Proteins: Basic Concepts and Clinical Implications" *Gen. Physiol. Biophys.* (1992) vol. 11, pp. 411-425.

Iyengar, R.: "Gating by Cyclic AMP: Expanded Role for an Old Signaling Pathway" *Science* (Jan. 1996) v. 271, pp. 461-463.

Kaibuchi, K. et al.: "Molecular Cloning of the cDNA for Stimulatory GDP/GTP Exchange Protein for smg p21s (ras p21-Like Small GTP-Binding Proteins) and Characterization of Stimulatory GDP/GTP Exchange Protein." *Molecular and Cellular Biology*, (May 1991), v. 11, No. 5, pp. 2873-2880, XP000881341.

Kedra D. et al.: "The Germinal Center Kinase Gene and a Novel CDC25-Like Gene are Located in the Vicinity of the PYGM Gene on 11q13." *Hum Genet* (Oct. 1997) v. 100, pp. 611-619, XP002069545.

Kedra D. et al.: "H. Sapiens mRNA for F25B.3 Kinase Like Protein From *C. Elegans*." AC Y12336, (Jun. 1997).

Kawasaki H. et al.: "A Rap Guanine Nucleotide Exchange Factor Enriched Highly in the Basal Ganglia." *Proc. Natl. Acad. Sci. USA*, (Oct. 1998), v. 95, pp. 13278-13283, XP000882748.

Kim, J.H. et al.: "Syn GAP: a Synaptic RasGAP that Associates with the PSD-95/SAP90 Protein Family" *Neuron* (Apr. 1998) v. 20, pp. 683-691.

Kitayama, H. et al.: "A ras-Related Gene with Transformation Suppressor Activity" *Cell* (1988) pp. 77-84.

Newton, A.C.: "Protein Kinase C: Structure, Function, and Regulation" *The Journal of Biological Chemistry* (Dec. 1995) v. 270, No. 48, pp. 28495-28498.

Overbeck, A.F. et al.: "Guanine Nucleotide Exchange Factors: Activators of Ras Superfamily Proteins" *Molecular Reproduction and Development* (1995) v. 42, pp. 468-476.

Renata, Z. et al.: "Ras-GRF, the Activator of Ras, is Expressed Preferentially in Mature Neurons of the Central Nervous System" *Molecular Brain Research* (1997) v. 48, pp. 140-144.

Santoro, B. et al.: "Identification of a Gene Encoding a Hyperpolarization-Activated Pacemaker channel of Brain" *Cell* (May 1998) v. 93, pp. 717-729.

Scholten, J.D. et al.: "Inhibitors of Farnesyl: Protein Transferase—A Possible Cancer Chemotherapeutic" *Bioorganic & Medicinal Chemistry* (1996) v.4, No. 9, pp. 1537-1543.

Silva, A.J. et al.: "A Mouse Model for the Learning and Memory Deficits Associate With Neurofibromatosis Type I" *Nature Genetics* (1997) v. 15, pp. 281-284.

Sturani, E. et al.: "The Ras Guanine Nucleotide Exchange Factor CDC25Mm is Present at the Synaptic Junction" *Experimental Cell Research* (1997) v. 235, pp. 117-123.

Vossler, M.R. et al.: "cAMP Activates MAP Kinase and Elk-1 Through a B-Raf- and Rap1-Dependent Pathway" *Cell* (1997) 73-82.

Walsh, D.A. et al.: "Multiple Pathway Signal Transduction by the cAMP-Dependent protein Kinase" *The FASEB Journal* (1994) v. 8 1227-1236.

York, R.D. et al: "Rap 1 Mediates Sustained MAP Kinase Activation Induce by Nerve Growth Factor" *Nature* (Apr. 1998) v. 392, pp. 622-626.

Zufall, F. et al: "Cyclic Nucleotide Gated Channels as Regulators of CNS Development and Plasticity" *Current Opinion in Neurobiology* (1997) v. 7, pp. 404-412.

Bos, J., (1998) "All in the family? New insights and questions regarding interconnectivity of Ras, Rap1 and Ral" *The EMBO Journal*, vol. 17; No. 23, pp. 6776-6782.

Coller et al.,(1995) "New Antiplatelet Agents: Platelet GPIIb/IIIa Antagonists" *Thrombosis and Haemostasis*, vol. 74 (1), pp. 302-308.

Newman et al., (Jan. 1985) "Quantitation of Membrane Glycoprotein IIIa on Intact Human Platelets Using the Monoclonal Antibody, AP-3" *Blood*, vol. 65; No. 1, pp. 227-232.

De Bruyn, (Oct., 1974) "Rap1 and Ral in signal transduction; The Ras family: molecular switches in signaling cascades," *Ras-like small GTPases in platelet biology*, University Medical Centre of Utrecht, The Netherlands, Chapter 1; General Introduction.

Zacharaski et al., (1990) "Chronic Calcium Antagonist Use in Carcinoma of the Lung and Colon: A Retrospective Cohort Observational Study" *Cancer Investigation*, vol. 8 (5), pp. 451-458.

Kawasaki et al., (Dec. 1998) "A Family of cAMP-Binding Proteins That Directly Activate Rap1", *Science*, vol. 282, pp. 2275-2279.

* cited by examiner

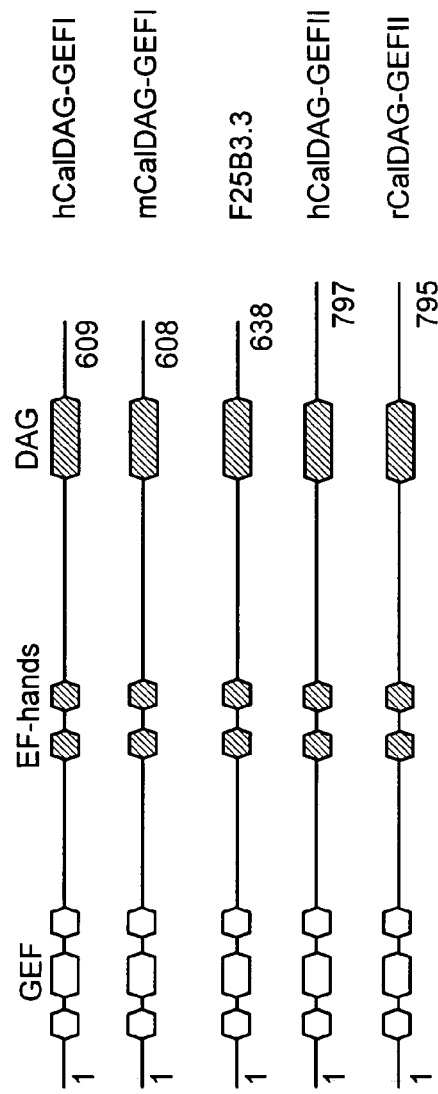
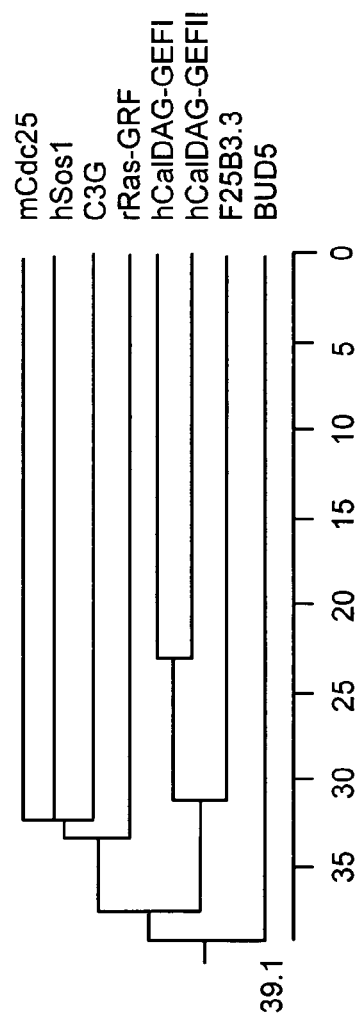
FIG. 2A
FIG. 2B

| FIG. 2D-1 |
|---|
| FIG. 2D-2 |

FIG. 2D

| hCalDAG-GEFI | MAGTLDLDKGCCTVEELLRGCTEAFDDSGKVRDPQLVRNFLNHPNYIPSS |
| mcalDAG-GEFI | MA[S]TLDLDKGCCTVEELLRGCTEAFDDSGKVRDPQLVRNFLNHPNYIPSS |
| hCalDAG-GEFI | KELKALLDQEGNRRHSSLIDIDSVPTYKNKRQVTQRNPVGQKKRKMSLLF |
| mcalDAG-GEFI | KELKALLDQEGNRRHSSLIDI[E]SVPTYKNKRQVTQRNPV[E]QKKRKMSLLF |
| hCalDAG-GEFI | NSVSQNVQLNILSKPTAPQRALVITHFVHVAEKLLQLQNFNTLNAVVGGL |
| mcalDAG-GEFI | NSVSQNVQLNILSKPTA[T]QRALVITHFVHVAEKLLQLQNFNTLNAVVGGL |
| hCalDAG-GEFI | FPILGVHLKDLVALQLALPDWLDPARTRLNGAKNKQLFSILEELANVTSL |
| mcalDAG-GEFI | FPILGVHLKDLVALQLALPDWLDP[G]RTRLNGAKNM[R]QLFSILEELANVTSL |
| hCalDAG-GEFI | PPRPPVLEENTSAAKPKLDQALVVEHIEKNVESVFRNFDVDGDGHISQEE |
| mcalDAG-GEFI | PPRPPVLEENTS[V]AKPKLDQALV[A]EHIEKNVESVFRNFDVDGDGHISQEE |
| hCalDAG-GEFI | FQESNSLRPVACRHCKALILGIYKQGLKCRACGVNCHKQCKDRLSVECRR |
| mcalDAG-GEFI | FQESNSLRPVACRHCKALILGIYKQGLKCRACGVNCHKQCK[E]RLSVECRR |
| hCalDAG-GEFI | EDGVFDIHL |
| mcalDAG-GEFI | EDGVFDIHL |

FIG. 2D-1

```
QLAAKLLHIYQQSRKDNSNSLQVKTCHLVRYNISAFPAEFDLNPELAEQI          100
QLA S KLLHE YQQSRKDNSNSLQVKTCHLVRYN V SAFPAEFDLNPELAE P I    100

DHLEPMELAEHLTYLEYRSFCKILFQDYHSFVTHGCTVDNPVLERFISLF          200
DHLEPMELAEHLTYLEYRSFCKILFQDYHSFVTHGCTVDNPVLERFISLF          200

SHSSISRLKETHSHVSPETIKLMEGLTELVTATGNYRRRLAACVGFR             300
SHSSISRLKETHSHVSP D TIKLMEGLTELVTATGNY S NYRRRLAACVGFR       300

RPPVQAMPDLLSLLTVSLDQYTEDELYQLSLQREPRSKSSPTSCTP              400
RPPVQAMPDLLSLLTVSLDQYTEDELYQLSLQREPRSKSSPTSCTP              400

FQIIRGNFPYLSAFGDLDQNQDGCISREEMVSYFLRSSVLGGRMGFVHM           500
FQIIRGNFPYLSAFGDLDQNQDGCISREEM I SYFLRSSVLGGRMGFVHM         500

RAQSVSLEGSAPSPMNSHHHRAFSFSLPRPGRRGSRPPEIREEVQTV             600
RAQSVSLEGSAPSPM T HM - RAFSFSLPRPGRR S SRPPEIREEVQ S V        599

```
F25B3.3          AVFKHYDRDGFISQEEFQ      473
hCalDAG-GEFI     SVFRNFDVDGDGHISQEEFQ    452
hCalDAG-GEFII    SVFKNYDHDQDGYISQEEFE    447
hCalmodulin      EAFSLFDKDGDGTITTKELG     34
hCalbindin D28K  LMLKLFDSNNDGKLELTEMA    168
hCalcineurin B   FAFRIYDMDKDGYISNGELF    113
hParvalbumin α   KVFHMLDKDKSGFIEEDELG     65
hTroponin C      ECFRIFDRNADGYIQPEELA    117
```

FIG. 2E

```
F25B3.3          HNFHETTFLTPITCNHCNKLLWGILRQGFKCKDCGLAVHSCKSNAVAEC   570
hCalDAG-GEFI     HNFQESNSLRPVACRHCKALILGIYKQGLKCRACGVNCHKQCKDRLSVEC   548
hCalDAG-GEFII    HNFQETTYLKPTFCDNCAGFLWGVIKQGYRCKDCGMNCHKQCKDLVYFEC   542
hPKCα            HKFIARFFKQPTFCSHCTDFIWGFGKQGFQCQVCCFVVHKRCHEFVTFSC    86
hPKCβ1           HKFTARFFKQPTFCSHCTDFIWGFGKQGFQCQVCCFVVHKRCHEFVTFEC    86
hPKCγ            HKFTARFFKQPTFCSHCTDFIWGIGKQGLQCQVCSFVVHRRCHEFVTFEC    85
```

FIG. 2F

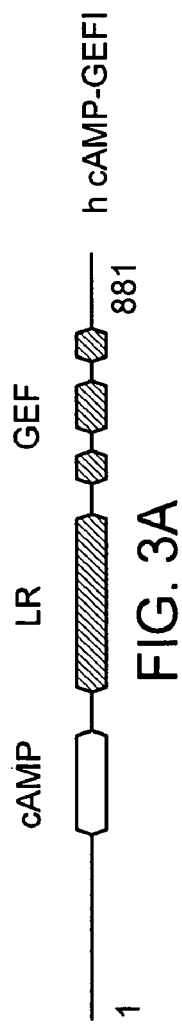
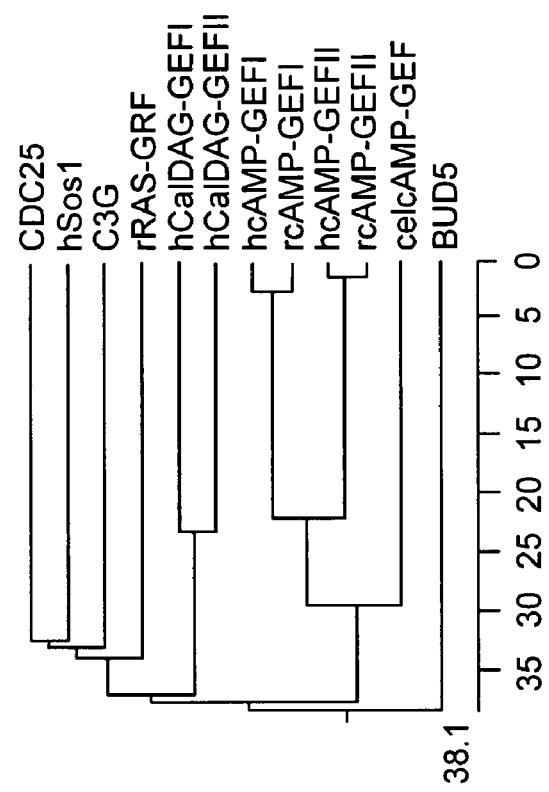
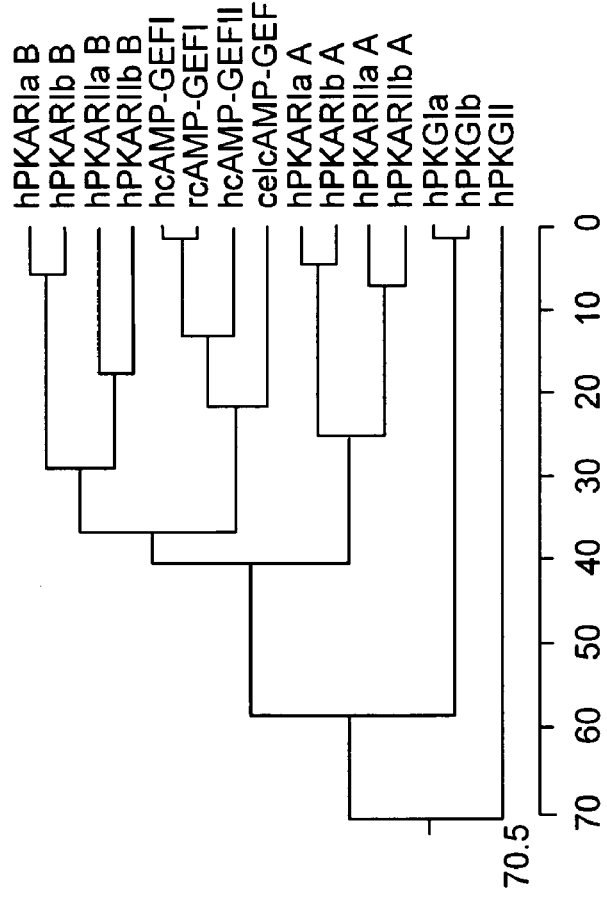
FIG. 3A
FIG. 3B
FIG. 3C

| | | |
|---|---|---|
| hcAMP-GEFI | M V L - - - - - - - - - - - - - - - - - | |
| hcAMP-GEFII | M V A A H A A H S S S S A E W I A C L D K | |
| hcAMP-GEFI | - - - - - - - - - - - - - - - - - H Q H P | |
| hcAMP-GEFII | Y A V L A G S L D V K V S E T S S H Q D A | |
| hcAMP-GEFI | - - - - - - - - - - - - - - - - - - T P | |
| hcAMP-GEFII | P Y G V M E T G S N N D R I P D K E N T P | |
| hcAMP-GEFI | L V D G I L A L G L G V H S R S Q V V G I | |
| hcAMP-GEFII | L V D W M M Q Q T P C V H S R T Q A V G M | |
| hcAMP-GEFI | S Q R G P D A L L T V A L R K P P G Q R T | |
| hcAMP-GEFII | S Q M G P D A H M R M I L R K P P G Q R T | |
| hcAMP-GEFI | G S V N V V T H G K G L V T T L H E G D D | |
| hcAMP-GEFII | G S V N V V I Y G K G V V C T L H E G D D | |
| hcAMP-GEFI | A S Q G A - G P S R P P T P G R N R Y T V | |
| hcAMP-GEFII | V P A G N R A S N Q G N S Q P Q Q K Y T V | |
| hcAMP-GEFI | G G S E Q E R S T Y V C N K R Q Q I L R L | |
| hcAMP-GEFII | Q G T E Q E K M D Y A L N N K R R V I R L | |
| hcAMP-GEFI | S P Q M K A R N L P V W L P N Q D E P L P | |
| hcAMP-GEFII | A P Q K K H K V L L Q Q F N T G D E R - A | |
| hcAMP-GEFI | G D A I G L Q P D A R G V A T S L G L N E | |
| hcAMP-GEFII | G E K V V L K P N D V S V F T T L T I N G | |
| hcAMP-GEFI | H Y V L G P Q H L R D V T T A N L E R F M | |
| hcAMP-GEFII | Y H T F G R H N F K K - T T A N L D L F L | |
| hcAMP-GEFI | R L A H T W E R L P H K V R K L Y S A L E | |
| hcAMP-GEFII | R L A L T W E K L P S K F K K F Y A E F E | |
| hcAMP-GEFI | A A R M L H H C R S H N P V P L S P L R S | |
| hcAMP-GEFII | T A R T V R Y Y R S Q - - - P F N P - - - | |

| - - - C S Y Q L L L E - - - - - - - - - - - - - - - | 20 |
| I C L C G Y Y E N L E K G I T L F R Q G D I G T N W | 80 |

| - L R - - - - - - - - - - W - - - - - - - - - - - - | 32 |
| L L R I E Q K D F K A L W E K Y R Q Y M A G L L A P | 160 |

| L A T C P N L I R D R K Y H L R L Y R Q C C S G R E | 92 |
| L S R A P H M I R D R K Y H L K T Y R Q C C V G T E | 240 |

| P E - - P V G T H E M - - - - E E L A E A V A L L | 166 |
| H E D A P L P T E E E K K E C D E E L Q D T M L L L | 319 |

| F E P H S K A G T V L F S Q G D K G T S W Y I I W K | 246 |
| F E S H A K G G T V L F N Q G E E G T S W Y I I L K | 399 |

| N R I I K D V E A K T M R L E E H G K V V L V L E R | 326 |
| N R I L R D V E A N T V R L K E H D Q D V L V L E K | 479 |

| L L T H R V F M P S A Q L C A A L H H F H V E P A | 405 |
| I M M H C V F M P N T Q L C P A L V A H Y H A Q P S | 559 |

| R L S N L L R E Q W P E R R C H R L E N G C G N A | 485 |
| R M I A A L K E Q L P E L E K I V K Q I S E - D A K | 638 |

| V R E V M A A L A Q E D G W T K G Q V L V K V N S A | 565 |
| V K E V I S A V A D K L G S G E G L I I V K M S S G | 717 |

| S A K D L A G Q L T D H D W S L F N S I H Q V E L I | 645 |
| S S K D L A Y Q M T I Y D W E L F N C V H E L E L I | 797 |

| A A H L K E Q K N V N S F F A V M F G L S N S P I S | 725 |
| A A H C K E Y K N L N S F F A I V M G L S N I A V S | 876 |

| M T F I H E G N H T L V E N L I N F E K M R M M A R | 805 |
| M T F T H E G N K T F I D N L V N F E K M R M I A N | 956 |

| V Q Q L K V I D N Q R E L S R L S R E L E P | 881 |
| V R Q L N V I D N Q R T L S Q M S H R L E P R R P | 1011 |

FIG. 3F-3

GENES INTEGRATING SIGNAL TRANSDUCTION PATHWAYS

RELATED APPLICATIONS

This application claims the benefit of U.S. application Nos. 60/105,507, filed on Oct. 23, 1998, and 60/108,685, filed on Nov. 16, 1998.

GOVERNMENT SUPPORT

This invention was made with government support under Grant Numbers HD28341, CA42063, HG00299 and HL41484 awarded by the National Institutes of Health. The government has certain rights in the invention.

FIELD OF THE INVENTION

The present invention relates generally to novel polynucleotides and proteins encoded by such polynucleotides, along with therapeutic, diagnostic, and research utilities for these polynucleotides and proteins.

BACKGROUND OF THE INVENTION

Ras proteins are key regulators of growth, differentiation and malignant transformation. In addition, these proteins are implicated in synaptic function and region-specific learning and memory functions in the brain.

As shown schematically in FIG. 1, Ras proteins cycle between inactive GDP-complexed and active GTP-complexed states. GTPase-activating proteins (GAPs) inactivate Ras proteins by stimulating hydrolysis of the bound GTP to GDP, whereas guanine nucleotide exchange factors (GEFs) activate Ras proteins by stimulating release of GDP and the uptake of GTP. So essential are GEFs to Ras action, that genetic loss of GEF function has similar effects to those induced by loss of the Ras proteins themselves. Loss of GEF function can be circumvented by mutations that constitutively activate the Ras proteins, such as an oncogene mutation, or, in some cases, through loss of GAP activity. Activated Ras proteins, which are localized at the plasma membrane, transmit signals from tyrosine kinases to a cascade of serine/threonine kinases, which delivers the signals to the cell nucleus.

Activation of Ras can result in the activation of the mitogen-activated protein (MAP) kinase (also known as extracellular-signal regulated kinase, or ERK) pathway. For example, a receptor tyrosine kinase is activated by a peptide mitogen such as epidermal growth factor (EGF). The EGF-stimulated receptor undergoes autophosphorylation of specific tyrosine residues in its cytoplasmic domain which creates phosphotyrosyl binding sites for the Src homology 2 (SH2) and/or phosphotyrosyl binding (PTB) domains of certain adapter proteins. The adapter protein becomes autophosphorylated on association with activated receptor tyrosine kinases. The GEF is stably associated with the adapter protein which, upon autophosphorylation, mediates translocation of the GEF to the plasma membrane. The GEF then activates the Ras protein. Activated Ras relays its signal downstream through a cascade of cytoplasmic proteins, including Raf-1 serine/threonine kinase. The Ras:Raf association promotes translocation of the normally cytoplasmic Raf protein to the plasma membrane, where subsequent events lead to the activation of its kinase function. Upon activation, Raf phosphorylates and activates two MAP kinases (also known as MEKs). MEKs directly associate with the catalytic domain of Raf-1 and are phosphorylated by Raf. Activated MEKs function as dual-specificity kinases and phosphorylate tandem threonine and tyrosine residues in the MAP kinases to activate them. Once activated, the MAP kinases translocate to the nucleus where they phosphorylate and activate a variety of substrates.

Rap proteins, members of the Ras small GTPase superfamily, can inhibit Ras signaling of the Ras/Raf-1(a serine/threonine kinase)/MAP kinase pathway or, through B-Raf, can activate MAP kinase. Rap1 consists of two isoforms, Rap1A and Rap1B, which differ mainly at the C-terminus. Characteristic features of Rap1 are its geranylgeranyl modification at the C-terminus, which is responsible for membrane attachments, and a threonine residue at position 61. In most other GTPases, the corresponding residue is a glutamine. Rap proteins, like Ras proteins, cycle between inactive GDP-complexed and active GTP-complexed states. GEFs are required to activate Rap proteins by stimulating the release of GDP and the uptake of GTP.

Constitutive activation of the Ras pathway contributes to malignant transformation. In fact, the Ras gene has been implicated in many human cancers, including lung cancer, breast cancer, colorectal cancer, exocrine pancreatic cancer, and myeloid leukemia. Biological and biochemical studies of Ras action indicate that Ras functions like a G-regulatory protein since Ras must be localized in the plasma membrane and must bind with GTP in order to transform cells. Gibbs et al., 53 MICROBIOL. REV. 171–286 (1989).

Targeting components of the Ras signaling pathways has been proposed as one approach for the development of anti-Ras drugs for cancer treatment. One potential approach for targeting Ras for cancer treatment involves the use of farnesyltransferase inhibitors (FTIs). Inhibition of farnesyl-protein transferase, and thereby of farnesylation of the Ras protein, blocks the ability of Ras to transform normal cells to cancer cells. Certain inhibitors of Ras farnesylation cause an increase in soluble Ras which can act as a dominant negative inhibitor of Ras function. While soluble Ras in cancer cells can become a dominant negative inhibitor, soluble Ras in normal cells would not be an inhibitor. A cytosol-localized and activated form of Ras acts as a dominant negative Ras inhibitor of membrane-bound Ras function. Gibbs et al., 86 PROC. NAT'L ACAD. SCI. USA 6630–34 (1989). FTIs block Ras function by preventing its post-translational modification by the farnesyl isoprenoid.

Intervention of Ras signaling at multiple or various points can significantly impact the ability of Ras to cause cellular transformation. Since Ras protein function is believed to be crucial to so many cellular processes, targeting only a subset of Ras functions by downstream intervention may provide significant advantages. Thus, there remains a need for identifying additional means for disrupting the Ras pathway. Applicants have discovered four new targets, namely GEFs specific for Rap1A, for disrupting the Ras pathway.

SUMMARY OF THE INVENTION

Applicants have discovered four mammalian genes which have been designated CalDAG-GEFI, CalDAG-GEFII, cAMP-GEFI, and cAMP-GEFII, which encode proteins having a substrate specificity for Rap1A. The proteins encoded by CalDAG-GEFI and CalDAG-GEFII, referred to herein generally as "CalDAG-GEF," have dual binding domains for calcium and diacylglycerol. The proteins cAMP-GEFI and cAMP-GEFII, referred to herein generally as "cAMP-GEF," have a binding domain for cyclic adenosine 3′,5′-monophosphate. The present disclosure provides polypeptide and polynucleotide sequences for *Mus musculus* CalDAG-GEFI, *Homo sapiens* CalDAG-GEFI, *Rattus norvegicus* CalDAG-GEFII, *Homo sapiens* CalDAG-GEFII, *Rattus norvegicus* cAMP-GEFI, *Homo sapiens* cAMP-GEFI, *Homo sapiens* alternatively spliced cAMP-GEFI, *Rattus norvegicus* cAMP-GEFII, and *Homo sapiens* cAMP-GEFII. See Kawasaki et al., 95 Proc. Natl. Acad. Sci. USA 13278–83 (1998), and Kawasaki et al., 282 Sci. 2275–79 (1998), the disclosures of both of which are incorporated by reference herein.

Thus, in one series of embodiments, the present invention provides isolated nucleic acids including nucleotide sequences comprising or derived from CalDAG-GEF or cAMP-GEF, or encoding polypeptides comprising or derived from CalDAG-GEF or cAMP-GEF proteins. The sequences of the invention include the specifically disclosed sequences, splice variants of these sequences, allelic variants of these sequences, synonymous sequences, and homologous or orthologous variants of these sequences. Thus, for example, the invention provides nucleic acid sequences from the *Mus musculus* CalDAG-GEFI, *Homo sapiens* CalDAG-GEFI, *Rattus norvegicus* CalDAG-GEFII, *Homo sapiens* CalDAG-GEFII, *Rattus norvegicus* cAMP-GEFI, *Homo sapiens* cAMP-GEFI, *Homo sapiens* alternatively spliced cAMP-GEFI, *Rattus norvegicus* cAMP-GEFII, and *Homo sapiens* cAMP-GEFII. The present invention also provides allelic variants and homologous or orthologous sequences by providing methods by which such variants may be routinely obtained. Because the nucleic acids of the invention may be used in a variety of diagnostic, therapeutic and recombinant applications, various subsets of the CalDAG-GEF and cAMP-GEF sequences are also provided. For example, for use in allele specific hybridization screening or PCR amplification techniques, subsets of the CalDAG-GEF and cAMP-GEF sequences, including both sense and antisense sequences, and both normal and mutant sequences, as well as intronic, exonic and untranslated sequences, are provided. Such sequences may comprise a small number of consecutive nucleotides from the sequences which are disclosed or otherwise enabled herein, but preferably include at least 8–10, more preferably 10–15, and most preferably 15–25, consecutive nucleotides from a CalDAG-GEF or cAMP-GEF sequence. In another embodiment, such sequences include between 25–500 consecutive nulceotides. Other preferred subsets of a CalDAG-GEF or cAMP-GEF sequence include those encoding one or more of the functional domains or antigenic determinants of the CalDAG-GEF or cAMP-GEF protein and, in particular, may include either normal (wild-type) or mutant sequences. The invention also provides for various nucleic acid constructs in which CalDAG-GEF or cAMP-GEF sequences, either complete or subsets, are operably joined to exogenous sequences to form cloning vectors, expression vectors, fusion vectors, transgenic constructs, and the like. Thus, in accordance with another aspect of the invention, a recombinant vector for transforming a mammalian or invertebrate tissue cell to express a normal or mutant CalDAG-GEF and/or cAMP-GEF sequence in the cells is provided.

In another series of embodiments, the present invention provides for host cells which have been transfected or otherwise transformed with one of the nucleic acids of the invention. The cells may be transformed merely for purposes of propagating the nucleic acid constructs of the invention, or may be transformed so as to express the CalDAG-GEF and/or cAMP-GEF sequences. The transformed cells of the invention may be used in assays to identify proteins and/or other compounds which affect normal or mutant CalDAG-GEF and/or cAMP-GEF expression, which interact with the normal or mutant CalDAG-GEF and/or cAMP-GEF proteins, and/or which modulate the function or effects of the normal or mutant proteins, or to produce the CalDAG-GEF and/or cAMP-GEF proteins, fusion proteins, functional domains, antigenic determinants, and/or antibodies of the invention. Transformed cells may also be implanted into hosts, including humans, for therapeutic or other reasons. Preferred host cells include mammalian cells, including pure or mixed cell cultures, as well as bacterial, yeast, nematode, insect and other invertebrate cells. For uses as described below, preferred cells also include embryonic stem cells, zygotes, gametes, and germ line cells.

In another series of embodiments, the present invention provides transgenic animal models of diseases or disorders associated with mutations in the CalDAG-GEF and/or cAMP-GEF genes. The animal may be essentially any non-human mammal, including rats, mice, hamsters, guinea pigs, rabbits, dogs, cats, goats, sheep, pigs, and non-human primates. In addition, invertebrate models, including nematodes and insects, may be used for certain applications. The animal models are produced by standard transgenic methods including microinjection, electroporation, transfection, or other forms of transformation of embryonic stem cells, zygotes, gametes, and germ line cells with vectors including genomic or cDNA fragments, minigenes, homologous recombination vectors, viral insertion vectors and the like. Suitable vectors include vaccinia virus, adenovirus, adeno-associated virus, retrovirus, liposome transport, neuraltropic viruses, and Herpes simplex virus. The animal models may include transgenic sequences comprising or derived from the CalDAG-GEF and/or cAMP-GEF genes, including normal and mutant sequences, intronic, exonic and untranslated sequences, and sequences encoding subsets of the CalDAG-GEF and/or cAMP-GEF proteins, such as functional domains. The major types of animal models provided include: (1) Animals in which a normal human CalDAG-GEF and/or cAMP-GEF gene has been recombinantly introduced into the genome of the animal as an additional gene, under the regulation of either an exogenous or an endogenous promoter element, and as either a recombinant gene or a large genomic fragment; in which a normal human CalDAG-GEF and/or cAMP-GEF gene has been recombinantly substituted for one or both copies of the animal's homologous CalDAG-GEF and/or cAMP-GEF gene by homologous recombination or gene targeting; and/or in which one or both copies of one of the animal's homologous CalDAG-GEF and/or cAMP-GEF genes have been recombinantly "humanized" by the partial substitution of sequences encoding the human homologue by homologous recombination or gene targeting; (2) Animals in which a mutant human CalDAG-GEF and/or cAMP-GEF gene has been recombinantly introduced into the genome of the animal as an additional gene, under the regulation of either an exogenous or an endogenous promoter element, and as either a recombinant gene or a large genomic fragment; in which a mutant human CalDAG-GEF and/or cAMP-GEF gene has been recombinantly substituted for one or both copies of the animal's homologous CalDAG-GEF and/or cAMP-GEF gene by homologous recombination or gene targeting; and/or in which one or both copies of one of the animal's homologous CalDAG-GEF and/or cAMP-GEF gene have been recombinantly "humanized" by the partial substitution of sequences encoding a mutant human homologue by homologous recombination or gene targeting; (3) Animals in which a mutant version of one of that animal's CalDAG-GEF or cAMP-GEF gene has been recombinantly introduced into the genome of the animal as an additional gene, under the regulation of either an exogenous or an endogenous promoter element, and as either a recombinant gene or a large genomic fragment; and/or in which a mutant version of one of that animal's CalDAG-GEF or cAMP-GEF gene has been recombinantly substituted for one or both copies of the animal's homologous CalDAG-GEF or cAMP-GEF gene by homologous recombination or gene targeting; and (4) "Knock-out" animals in which one or both copies of one of the animal's CalDAG-GEF or cAMP-GEF genes have been partially or completely deleted by homologous recombination or gene targeting, or have been inactivated by the insertion or substitution by homologous recombination or gene targeting of exogenous sequences.

In another series of embodiments, the present invention provides for substantially pure protein preparations including polypeptides comprising or derived from the CalDAG-GEF and/or cAMP-GEF proteins. The CalDAG-GEF and cAMP-GEF protein sequences of the invention include the specifically disclosed sequences, variants of these sequences resulting from alternative mRNA splicing, allelic variants of these sequences, and homologous or orthologous variants of these sequences. Thus, for example, the invention provides amino acid sequences from the *Mus musculus* CalDAG-GEFI protein, *Homo sapiens* CalDAG-GEFI protein, *Rattus norvegicus* CalDAG-GEFII protein, *Homo sapiens* CalDAG-GEFII protein, *Rattus norvegicus* cAMP-GEFI protein, *Homo sapiens* cAMP-GEFI protein, *Homo sapiens* alternatively spliced cAMP-GEFI protein, *Rattus norvegicus* cAMP-GEFII protein, and *Homo sapiens* cAMP-GEFII protein. The present invention also provides allelic variants and homologous or orthologous proteins by providing methods by which such variants may be routinely obtained. The present invention also specifically provides for mutant or disease-causing variants of CalDAG-GEF and cAMP-GEF by providing methods by which such variants may be routinely obtained. Because the proteins of the invention may be used in a variety of diagnostic, therapeutic and recombinant applications, various subsets of the CalDAG-GEF and cAMP-GEF protein sequences and combinations of the CalDAG-GEF and cAMP-GEF protein sequences with heterologous sequences are also provided. For example, for use as immunogens or in binding assays, subsets of the CalDAG-GEF and cAMP-GEF protein sequences, including both normal and mutant sequences, are provided. Such protein sequences may comprise a small number of consecutive amino acid residues from the sequences which are disclosed or otherwise enabled herein, but preferably include at least 4–8, and preferably at least 9–15 consecutive amino acid residues from a CalDAG-GEF or cAMP-GEF sequence. In another embodiment, such sequences comprise at least 15–200 consectuive amino acid residues. Other preferred subsets of the CalDAG-GEF and cAMP-GEF protein sequences include those corresponding to one or more of the functional domains or antigenic determinants of the CalDAG-GEF and cAMP-GEF proteins and, in particular, may include either normal (wild-type) or mutant sequences. The invention also provides for various protein constructs in which a CalDAG-GEF and/or cAMP-GEF sequences, either complete or subsets thereof, are joined to exogenous sequences to form fusion proteins and the like. In accordance with these embodiments, the present invention also provides for methods of producing all of the above described proteins which comprise, or are derived from, CalDAG-GEF and/or cAMP-GEF.

In another series of embodiments, the present invention provides for the production and use of polyclonal and monoclonal antibodies, including antibody fragments, including Fab fragments, F(ab')$_2$, and single chain antibody fragments, which selectively bind to CalDAG-GEF or cAMP-GEF, or to specific antigenic determinants of CalDAG-GEF or cAMP-GEF. The antibodies may be raised in mouse, rabbit, goat or other suitable animals, or may be produced recombinantly in cultured cells such as hybridoma cell lines. Preferably, the antibodies selectively bind to a sequence comprising at least 4–8, and preferably at least 9–15, and more preferably at least 15–200 consecutive amino acid residues from a CalDAG-GEF or cAMP-GEF sequence. The antibodies of the invention may be used in the various diagnostic, therapeutic and technical applications described herein.

In another series of embodiments, the present invention provides methods of screening or identifying proteins, small molecules or other compounds which are capable of inducing or inhibiting the expression and/or function of the CalDAG-GEF and/or cAMP-GEF genes or proteins. The assays may be performed in vitro using non-transformed cells, immortalized cell lines, or recombinant cell lines, or in vivo using the transgenic animal models enabled herein. In particular, the assays may detect the presence of increased or decreased expression of CalDAG-GEF and/or cAMP-GEF-related genes or proteins on the basis of increased or decreased mRNA expression, increased or decreased levels of CalDAG-GEF and/or cAMP-GEF-related protein products, or increased or decreased levels of expression of a marker gene (e.g., β-galactosidase, green fluorescent protein, alkaline phosphatase or luciferase) operably joined to a 5' regulatory region in a recombinant construct. Cells known to express CalDAG-GEF or cAMP-GEF, or transformed to express CalDAG-GEF or cAMP-GEF, are incubated and one or more test compounds are added to the medium. After allowing a sufficient period of time (e.g., 0–72 hours) for the compound to induce or inhibit the expression of the CalDAG-GEF or cAMP-GEF, any change in levels of expression from an established baseline may be detected using any of the techniques described above. In particularly preferred embodiments, the cells are from an immortalized cell line such as a human neuroblastoma, glioblastoma or a hybridoma cell line, or are transformed cells of the invention.

In another series of embodiments, the present invention provides methods for identifying proteins and other compounds which bind to, or otherwise directly interact with, CalDAG-GEF and/or cAMP-GEF. The proteins and compounds will include endogenous cellular components which interact with the CalDAG-GEF and/or cAMP-GEF in vivo and which, therefore, provide new targets for pharmaceutical and therapeutic interventions, as well as recombinant, synthetic, and otherwise exogenous compounds which may have CalDAG-GEF and/or cAMP-GEF binding capacity and, therefore, may be candidates for pharmaceutical agents. Particularly useful components will bind with a SCR1, SCR2, SCR3, EF hand, DAG-binding or cAMP-binding domain. Thus, in one series of embodiments, cell lysates or tissue homogenates (e.g., human brain homogenates, lymphocyte lysates) may be screened for proteins or other compounds which bind to one of the normal or mutant CalDAG-GEF or cAMP-GEF proteins. Alternatively, any of a variety of exogenous compounds, both naturally occurring and/or synthetic (e.g., libraries of small molecules or peptides), may be screened for CalDAG-GEF or cAMP-GEF binding capacity. In each of these embodiments, an assay is conducted to detect binding between a "CalDAG-GEF component" or a "cAMP-GEF component" and some other moiety. The "CalDAG-GEF component" or the "cAMP-GEF component" in these assays may be any polypeptide comprising or derived from a normal or mutant CalDAG-GEF or cAMP-GEF protein, including functional domains or antigenic determinants of CalDAG-GEF or cAMP-GEF, or CalDAG-GEF or cAMP-GEF fusion proteins. In one embodiment, a CalDAG-GEF component is a SCR1, SCR2, SCR3, EF hand, or DAG-binding domain. In another embodiment a cAMP-GEF component is a SCR1, SCR2, SCR3, or cAMP-binding domain. Binding may be detected by non-specific measures (e.g., changes in intracellular $Ca^{2+}$, GTP/GDP ratio) or by specific measures (e.g., changes in the expression of downstream genes which can be monitored by differential display, 2D gel electrophoresis, differential hybridization, or SAGE methods). The preferred methods involve variations on the following techniques: (1) direct extraction by affinity chromatography; (2) co-isolation of CalDAG-GEF or cAMP-GEF components and bound proteins or other compounds by immunoprecipitation; (3) the Biomolecular Interaction Assay (BIAcore); and (4) the yeast two-hybrid systems.

In another series of embodiments, the present invention provides for methods of identifying proteins, small molecules and other compounds capable of modulating the activity of normal or mutant CalDAG-GEF or cAMP-GEF. Using normal cells or animals, the transformed cells and transgenic animal models of the present invention, or cells obtained from subjects bearing normal or mutant CalDAG-GEF or cAMP-GEF genes, the present invention provides methods of identifying such compounds on the basis of their ability to affect the expression of CalDAG-GEF and/or cAMP-GEF, the intracellular localization of the CalDAG-GEF and/or cAMP-GEF, or other biochemical, histological, or physiological markers which distinguish cells bearing normal and mutant CalDAG-GEF and/or cAMP-GEF sequences. Using the transgenic animals of the invention, methods of identifying such compounds are also provided on the basis of the ability of the compounds to affect behavioral, physiological or histological phenotypes associated with mutations in CalDAG-GEF and/or cAMP-GEF.

In another series of embodiments, the present invention provides methods and reagents for the screening and diagnosis of diseases or disorders associated with mutations in the CalDAG-GEF and/or cAMP-GEF genes. Screening and/or diagnosis can be accomplished by methods based upon the nucleic acids (including genomic and mRNA/cDNA sequences), proteins, and/or antibodies disclosed and enabled herein, including functional assays designed to detect failure or augmentation of the normal CalDAG-GEF and/or cAMP-GEF activity and/or the presence of specific new activities conferred by the mutant CalDAG-GEF and/or cAMP-GEF. Thus, for example, screens and diagnostics based upon CalDAG-GEF and/or cAMP-GEF proteins are provided which detect differences between mutant and normal CalDAG-GEF or cAMP-GEF in electrophoretic mobility, in proteolytic cleavage patterns, in molar ratios of the various amino acid residues, or in ability to bind specific antibodies. In addition, screens and diagnostics based upon nucleic acids (gDNA, cDNA or mRNA) are provided which detect differences in nucleotide sequences by direct nucleotide sequencing, hybridization using allele specific oligonucleotides, restriction enzyme digest and mapping (e.g., RFLP, REF-SSCP), electrophoretic mobility (e.g., SSCP, DGGE), PCR mapping, RNase protection, chemical mismatch cleavage, ligase-mediated detection, and various other methods. Other methods are also provided which detect abnormal processing of CalDAG-GEF and/or cAMP-GEF or proteins reacting with CalDAG-GEF and/or cAMP-GEF, alterations in CalDAG-GEF and/or cAMP-GEF transcription, translation, and post-translational modification; alterations in the intracellular and extracellular trafficking of CalDAG-GEF and/or cAMP-GEF gene products; or abnormal intracellular localization of CalDAG-GEF and/or cAMP-GEF. Such methods and reagents are also useful in the analysis of neoplasias and mammalian immune system function, as well as functional in vivo imaging of mammalian organ systems. In accordance with these embodiments, diagnostic kits are also provided which will include the reagents necessary for the above-described diagnostic screens.

In another series of embodiments, the present invention provides methods and therapeutic agents for use in the treatment of conditions such as neurological and neuropsychiatric disorders such as Huntington's disease, Parkinson's disease, Alzheimer's disease, dystonia, Tourette's syndrome, obsessive-compulsive disorder, attention deficit/hyperactive disorder, depression, schizophrenia, and stroke; neoplasias such as solid tumors including colon, breast, lung, prostate, and hematopoietic tumors such as leukemia, Hodgkins, and non-Hodgkins lymphomas; and autoimmune diseases, allergies, and asthma; as well as for the enhancement of the immune response in normal and immunocompromised individuals. These methods and therapeutic agents may be based upon (1) administration of normal CalDAG-GEF and/or cAMP-GEF proteins; (2) gene therapy with normal CalDAG-GEF and/or cAMP-GEF genes to compensate for or replace the mutant genes; (3) gene therapy based upon antisense sequences to mutant CalDAG-GEF and/or cAMP-GEF genes or upon sequences which "knock-out" the mutant genes; (4) gene therapy based upon sequences which encode a protein which blocks or corrects the deleterious effects of CalDAG-GEF and/or cAMP-GEF mutants; (5) immunotherapy based upon antibodies to normal and/or mutant CalDAG-GEF and/or cAMP-GEF proteins; or (6) small molecules (drugs) which alter CalDAG-GEF and/or cAMP-GEF expression, block interactions between (normal or mutant) forms of CalDAG-GEF and/or cAMP-GEF and other proteins or ligands, or which otherwise block the function of (normal or mutant) CalDAG-GEF and/or cAMP-GEF proteins by altering the structure of the proteins, by enhancing their metabolic clearance, or by inhibiting their function.

In accordance with another aspect of the invention, the proteins of the invention can be used as starting points for rational drug design to provide ligands, therapeutic drugs or other types of small chemical molecules. Alternatively, small molecules or other compounds identified by the above-described screening assays may serve as "lead compounds" in rational drug design.

BRIEF DESCRIPTION OF THE DRAWINGS

FIG. 2A shows human (h) and mouse (m) CalDAG-GEFI, human (h) and rat (r) CalDAG-GEFII, and C. elegans (cel) (F25B3.3, GenBank accession number: 1262950) CalDAG-GEF.

FIG. 2B shows a computer-generated phylogenetic tree analysis of the GEF domains of hCalDAG-GEFI and hCalDAG-GEFII in relation to mCdc25, hSos1, C3G, rRas-GRF, C. elegans (cel) (F25B3.3, GenBank accession number: 1262950) and BUD5.

FIG. 2D shows the full-length amino acid sequences of human (h) (SEQ. ID NO: 4), and mouse (m) (SEQ. ID NO: 2) CalDAG-GEFI (box indicates amino acid differences).

FIG. 2E shows the sequence similarity (black indicates identity) of EF-hand domains in hCalDAG-GEFI (SEQ. ID NO: 4: 433–452), hCalDAG-GEFII (SEQ. ID NO: 60), hCalmodulin (SEQ. ID NO: 38), hCalbindin D28K (SEQ. ID NO: 39), hCalcineurin B (SEQ. ID NO: 40), hParvalbumin α (SEQ. ID NO: 41), hTroponin C (SEQ. ID NO: 42), and *C. elegans* (cel)(F25B3.3, GenBank accession number: 1262950 (SEQ. ID NO: 37).

FIG. 2F shows the sequence similarity of DAG-binding domains of hCalDAG-GEFI (SEQ. ID NO: 4: 499–548), hCalDAG-GEFII (SEQ. ID NO: 61), hPKCα (SEQ. ID NO: 44), hPKCβ1 (SEQ. ID NO: 45), hPKCγ (SEQ. ID NO: 46) and *C. elegans* (cel) (F25B3.3, GenBank accession number: 1262950)(SEQ. ID NO: 43).

FIG. 3A is a schematic representation of human (h) cAMP-GEFI protein.

FIG. 3B is a phylogenetic tree analysis of cAMP binding domains of cAMP-GEFI and II and other cyclic nucleotide binding proteins.

FIG. 3C is a phylogenetic tree analysis of GEF domains of cAMP-GEFI and II and other Ras superfamily GEFs.

FIG. 3E shows the amino acid sequences of the cAMP binding pockets of human (h) cAMP-GEFI (SEQ. ID NO: 12), and rat (r) cAMP-GEFI (SEQ. ID NO: 10), human (h) cAMP-GEFII (SEQ. ID NO: 59), celcAMP-GEF (SEQ. ID NO: 51), hPKARla A (SEQ. ID NO: 52), hPKARlla A (SEQ. ID NO: 53), hPKARla B (SEQ. ID NO: 54), hPKARlla B (SEQ. ID NO: 55), hPKGla (SEQ. ID NO: 56), hPKGlb (SEQ. ID NO: 57), and hPKGll (SEQ. ID NO: 58). The positions of invariant amino acid residues are shown by black diamonds. The open diamond indicates the amino acid that determines the binding specificity for cAMP or cGMP. The arrow indicates the position of amino acid substitutions specific to cAMP-GEFs.

FIG. 3F is the full-length amino acid sequences of human cAMP-GEFI (SEQ. ID NO: 12) and human cAMP-GEFII (SEQ. ID NO: 59)(boxes indicate amino acid identity).

DETAILED DESCRIPTION OF THE INVENTION

Figure 1:
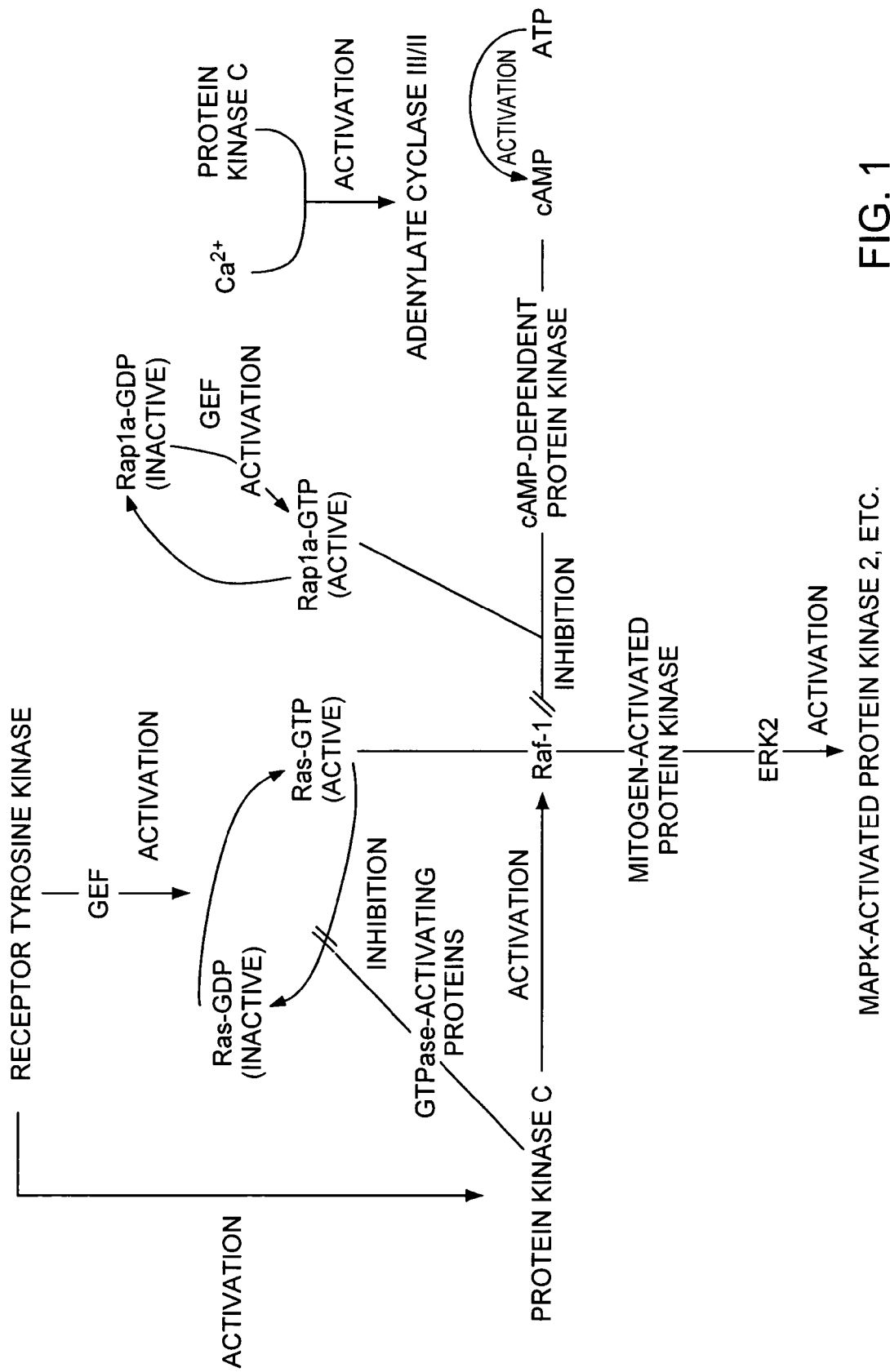
FIG. 1 is a partial schematic diagram of a Ras pathway.

The present invention is based, in part, upon the discovery of a family of mammalian genes which are associated with the Ras pathway. The discovery of these genes, designated CalDAG-GEFI, CalDAG-GEFII, cAMP-GEFI, and cAMP-GEFII, as well as the characterization of these genes, their protein products, mutants, and possible functional roles, are described below.

I. Definitions

In order to facilitate review of the various embodiments of the invention, and an understanding of the various elements and constituents used in making and using the invention, the following definitions are provided for particular terms used in the description and the claims which follow:

CalDAG-GEF. As used without further modification herein, the terms "CalDAG-GEF" or "CalDAG-GEFs" refer to the CalDAG-GEFI and/or the CalDAG-GEFII genes/proteins. In particular, the unmodified terms "CalDAG-GEF" or "CalDAG-GEFs" refer to the mammalian genes/proteins and, preferably, the human genes/proteins.

cAMP-GEF. As used without further modification herein, the terms "cAMP-GEF" or "cAMP-GEFs" refer to the cAMP-GEFI and/or the cAMP-GEFII genes/proteins. In particular, the unmodified terms "cAMP-GEF" or "cAMP-GEFs" refer to the mammalian genes/proteins and, preferably, the human genes/proteins.

CalDAG-GEF gene. As used herein, the term "CalDAG-GEF gene" means the mammalian genes represented by SEQ ID NOS: 1, 3, 5, and 7, as well as any allelic variants and heterospecific mammalian homologues. A murine CalDAG-GEFI cDNA sequence is disclosed herein as SEQ ID NO: 1, and a human CalDAG-GEFI cDNA sequence is disclosed herein as SEQ ID NO: 3. A rat CalDAG-GEFII cDNA sequence is disclosed herein as SEQ ID NO: 5, and a human CalDAG-GEFII cDNA sequence is disclosed herein as SEQ ID NO: 7. The term "CalDAG-GEF gene" primarily relates to a coding sequence, but can also include some or all of the flanking regulatory regions and/or introns. The term "CalDAG-GEF gene" specifically includes artificial or recombinant genes created from cDNA or genomic DNA, including recombinant genes based upon splice variants.

CalDAG-GEF protein. As used herein, the term "CalDAG-GEF protein" means a protein encoded by a CalDAG-GEF gene, including allelic variants and heterospecific mammalian homologues. A murine CalDAG-GEFI protein sequence is disclosed herein as SEQ ID NO: 2, and a human CalDAG-GEFI protein sequence is disclosed herein as SEQ ID NO: 4. A rat CalDAG-GEFII protein sequence is disclosed herein as SEQ ID NO: 6, and a human CalDAG-GEFII protein sequence is disclosed herein as SEQ ID NO: 8. Splice variants are also embraced by the term CalDAG-GEF protein as used herein. The protein may be produced by recombinant cells or organisms, may be substantially purified from natural tissues or cell lines, or may be synthesized chemically or enzymatically. Therefore, the term "CalDAG-GEF protein" is intended to include the protein in glycosylated, partially glycosylated, or unglycosylated forms, as well as in phosphorylated, partially phosphorylated, unphosphorylated, sulphated, partially sulphated, or unsulphated forms. The term also includes allelic variants and other functional equivalents of the CalDAG-GEF amino acid sequences, including biologically active proteolytic or other fragments.

hCalDAG-GEF gene and/or protein. As used herein, the abbreviation "hCalDAG-GEF" refers to the human homologue and human allelic variants of the CalDAG-GEF genes and/or proteins. Two cDNA sequences of the human CalDAG-GEF genes are disclosed herein as SEQ ID NOS:

3 and 7. The corresponding hCalDAG-GEF protein sequences are disclosed herein as SEQ ID NOS: 4 and 8. Allelic variants, including deleterious mutants, are enabled in the description which follows.

mCalDAG-GEF gene and/or protein. As used herein, the abbreviation "mCalDAG-GEF" refers to the murine homologues and murine allelic variants of the CalDAG-GEF gene and/or protein. A cDNA sequence of one murine CalDAG-GEF gene is disclosed herein as SEQ ID NO: 16. The corresponding mCalDAG-GEF protein sequence is disclosed herein as SEQ ID NO: 17. Allelic variants, including deleterious mutants, are enabled in the description which follows.

rCalDAG-GEF gene and/or protein. As used herein, the abbreviation "rCalDAG-GEF" refers to the rat homologue and rat allelic variants of the CalDAG-GEF genes and/or proteins. A cDNA sequence of one rat CalDAG-GEF gene is disclosed herein as SEQ ID NO: 5. The corresponding rCalDAG-GEF protein sequence is disclosed herein as SEQ ID NO: 6. Allelic variants, including deleterious mutants, are enabled in the description which follows.

cAMP-GEF gene. As used herein, the term "cAMP-GEF gene" means the mammalian genes represented by SEQ ID NOS: 9, 11, 13, 15, and 17, as well as any allelic variants and heterospecific mammalian homologues. A rat cAMP-GEFI cDNA sequence is disclosed herein as SEQ ID NO: 9, and a human cAMP-GEFI cDNA sequence is disclosed as SEQ ID NO: 11. Another human cAMP-GEFI cDNA sequence, resulting from alternative splicing of the mRNA transcript, is disclosed as SEQ ID NO: 13. A rat cAMP-GEFII cDNA sequence is disclosed as SEQ ID NO: 15, and a human cAMP-GEFII cDNA sequence is disclosed as SEQ ID NO: 17. The term "cAMP-GEF gene" primarily relates to a coding sequence, but can also include some or all of the flanking regulatory regions and/or introns. The term cAMP-GEF gene specifically includes artificial or recombinant genes created from cDNA or genomic DNA, including recombinant genes based upon splice variants.

cAMP-GEF protein. As used herein, the term "cAMP-GEF protein" means a protein encoded by a cAMP-GEF gene, including allelic variants and heterospecific mammalian homologues. A rat cAMP-GEFI protein sequence is disclosed herein as SEQ ID NO: 10, and a human cAMP-GEFI protein sequence is disclosed as SEQ ID NO: 12. Another human cAMP-GEFI protein sequence, resulting from alternative splicing of the mRNA transcript, is disclosed as SEQ ID NO: 14. A rat cAMP-GEFII protein sequence is disclosed as SEQ ID NO: 16, and a human cAMP-GEFII protein sequence is disclosed as SEQ ID NO: 18. Splice variants are also embraced by the term cAMP-GEF protein as used herein. The protein may be produced by recombinant cells or organisms, may be substantially purified from natural tissues or cell lines, or may be synthesized chemically or enzymatically. Therefore, the term "cAMP-GEF protein" is intended to include the protein in glycosylated, partially glycosylated, or unglycosylated forms, as well as in phosphorylated, partially phosphorylated, unphosphorylated, sulphated, partially sulphated, or unsulphated forms. The term also includes allelic variants and other functional equivalents of the cAMP-GEF amino acid sequences, including biologically active proteolytic or other fragments.

hcAMP-GEF gene and/or protein. As used herein, the abbreviation "hcAMP-GEF" refers to the human homologue and human allelic variants of the cAMP-GEF gene and/or protein. One cDNA sequences of the human cAMP-GEF gene is disclosed herein as SEQ ID NO: 7. The corresponding hcAMP-GEF protein sequence is disclosed herein as SEQ ID NO: 8. Numerous allelic variants, including deleterious mutants, are disclosed and enabled throughout the description which follows.

rcAMP-GEF gene and/or protein. As used herein, the abbreviation "rcAMP-GEF" refers to the rat homologue and rat allelic variants of the cAMP-GEF gene and/or protein. Two cDNA sequences of rat cAMP-GEF genes are disclosed herein as SEQ ID NOS: 9 and 15. The corresponding rcAMP-GEF protein sequences are disclosed herein as SEQ ID NOS: 10 and 16. Numerous allelic variants, including deleterious mutants, are disclosed and enabled throughout the description which follows.

Normal. As used herein with respect to genes, the term "normal" refers to a gene which encodes and expresses a normal protein. As used herein with respect to proteins, the term "normal" means a protein which performs its usual or normal physiological role and which is not associated with, or causative of, a pathogenic condition or state. Therefore, as used herein, the term "normal" is essentially synonymous with the usual meaning of the phrase "wild type." For any given gene, or corresponding protein, a multiplicity of normal allelic variants may exist, none of which is associated with the development of a pathogenic condition or state. Such normal allelic variants include, but are not limited to, variants in which one or more nucleotide substitutions do not result in a change in the encoded amino acid sequence.

Mutant. As used herein with respect to genes, the term "mutant" refers to a gene which encodes a mutant protein and/or fails to express a normal protein. As used herein with respect to proteins, the term "mutant" means a protein which does not perform its usual or normal physiological role and which is associated with, or causative of, a pathogenic condition or state. Therefore, as used herein, the term "mutant" is essentially synonymous with the terms "dysfunctional," "pathogenic," "disease-causing," and "deleterious." With respect to the CalDAG-GEF and cAMP-GEF genes and proteins of the present invention, the term "mutant" refers to CalDAG-GEF and cAMP-GEF genes/proteins bearing one or more nucleotide/amino acid substitutions, insertions and/or deletions which cause the genes/proteins to be dysfunctional, pathogenic, disease-causing or otherwise deleterious. This definition is understood to include the various mutations that naturally exist, including but not limited to those disclosed herein, as well as synthetic or recombinant mutations produced by human intervention. The term "mutant," as applied to the CalDAG-GEF and cAMP-GEF genes, is not intended to embrace sequence variants which, due to the degeneracy of the genetic code, encode proteins identical to the normal sequences disclosed or otherwise enabled herein; nor is it intended to embrace sequence variants which, although they encode different proteins, encode proteins which are functionally equivalent to normal CalDAG-GEF and/or cAMP-GEF proteins.

Functional equivalent. As used herein in describing gene sequences and amino acid sequences, the term "functional equivalent" means that a recited sequence need not be identical to a particularly disclosed sequence of the SEQ ID NOs but need only provide a sequence which functions biologically and/or chemically as the equivalent of the disclosed sequence.

Substantially pure. As used herein with respect to protein preparations, the term "substantially pure" means a preparation which contains at least 60% (by dry weight) the protein of interest, exclusive of the weight of other intentionally included compounds. Preferably the preparation is at least 75%, more preferably at least 90%, and most preferably at least 99%, by dry weight the protein of interest, exclusive of the weight of other intentionally included compounds. Purity can be measured by any appropriate method, e.g., column chromatography, gel electrophoresis, or HPLC analysis. If a preparation intentionally includes two or more different proteins of the invention, a "substantially pure" preparation means a preparation in which the total dry weight of the proteins of the invention is at least 60% of the total dry weight, exclusive of the weight of other intentionally included compounds. Preferably, for such preparations containing two or more proteins of the invention, the total weight of the proteins of the invention be at least 75%, more preferably at least 90%, and most preferably at least 99%, of the total dry weight of the preparation, exclusive of the weight of other intentionally included compounds. Thus, if the proteins of the invention are mixed with one or more other proteins (e.g., serum albumin, 6-OST) or compounds (e.g., diluents, detergents, excipients, salts, polysaccharides, sugars, lipids) for purposes of administration, stability, storage, and the like, the weight of such other proteins or compounds is ignored in the calculation of the purity of the preparation.

Isolated nucleic acid. As used herein, an "isolated nucleic acid" is a ribonucleic acid, deoxyribonucleic acid, or nucleic acid analog comprising a polynucleotide sequence that has been isolated or separated from sequences that are immediately contiguous (one on the 5' end and one on the 3' end) in the naturally occurring genome of the organism from which it is derived. The term therefore includes, for example, a recombinant nucleic acid which is incorporated into a vector, into an autonomously replicating plasmid or virus, or into the genomic DNA of a prokaryote or eukaryote; or which exists as a separate molecule (e.g., a cDNA or a genomic DNA fragment produced by PCR or restriction endonuclease treatment) independent of other sequences. It also includes a recombinant DNA which is part of a hybrid gene encoding additional polypeptide sequences and/or including exogenous regulatory elements.

Transformed cell. As used herein, a "transformed cell" is a cell into which (or into an ancestor of which) has been introduced, by means of recombinant DNA techniques, a nucleic acid molecule of interest. The nucleic acid of interest will typically encode a peptide or protein. The transformed cell may express the sequence of interest or may be used only to propagate the sequence. The term "transformed" may be used herein to embrace any method of introducing exogenous nucleic acids including, but not limited to, transformation, transfection, electroporation, microinjection, viral-mediated transfection, and the like.

Operably joined. As used herein, a coding sequence and a regulatory region are said to be "operably joined" when they are covalently linked in such a way as to place the expression or transcription of the coding sequence under the influence or control of the regulatory region. If it is desired that the coding sequences be translated into a functional protein, two DNA sequences are said to be operably joined if induction of promoter function results in the transcription of the coding sequence and if the nature of the linkage between the two DNA sequences does not (1) result in the introduction of a frame-shift mutation, (2) interfere with the ability of the regulatory region to direct the transcription of the coding sequences, or (3) interfere with the ability of the corresponding RNA transcript to be translated into a protein. Thus, a regulatory region would be operably joined to a coding sequence if the regulatory region were capable of effecting transcription of that DNA sequence such that the resulting transcript might be translated into the desired protein or polypeptide.

Stringent hybridization conditions. Stringent hybridization conditions is a term of art understood by those of ordinary skill in the art. For any given nucleic acid sequence, stringent hybridization conditions are those conditions of temperature, chaotrophic acids, buffer, and ionic strength which will permit hybridization of that nucleic acid sequence to its complementary sequence and not to substantially different sequences. The exact conditions which constitute "stringent" conditions, depend upon the nature of the nucleic acid sequence, the length of the sequence, and the frequency of occurrence of subsets of that sequence within other non-identical sequences. By varying hybridization conditions from a level of stringency at which non-specific hybridization occurs to a level at which only specific hybridization is observed, one of ordinary skill in the art can, without undue experimentation, determine conditions which will allow a given sequence to hybridize only with complementary sequences. Suitable ranges of such stringency conditions are described in KRAUSE ET AL., METHODS IN ENZYMOLOGY, 200: 546–56 (1991). Stringent hybridization conditions, depending upon the length and commonality of a sequence, may include temperatures of 20° C.–65° C. and ionic strengths from 5× to 0.1×SSC. Highly stringent hybridization conditions may include temperatures as low as 40–42° C. (when denaturants such as formamide are included) or up to 60–65° C. in ionic strengths as low as 0.1×SSC. These ranges, however, are only illustrative and, depending upon the nature of the target sequence, and possible future technological developments, may be more stringent than necessary. Less than stringent conditions are employed to isolate nucleic acid sequences which are substantially similar, allelic or homologous to any given sequence.

Selectively bind. As used herein with respect to antibodies, an antibody is said to "selectively bind" to a target if the antibody recognizes and binds the target of interest but does not substantially recognize and bind other molecules in a sample, e.g., a biological sample, which includes the target of interest.

CalDAG-GEF- or cAMP-GEF-associated disorder, condition, or disease. AS used herein, the term "CalDAG-GEF or cAMP-GEF associated disorder, condition, or disease" means any disorder, condition, or disease to which a normal or mutant CalDAG-GEF and/or cAMP-GEF is related in any manner, such as in the causation, prevention, exacerbation, alleviation of the disorder. Thus, as used herein, a CalDAG-GEF- or cAMP-GEF-associated disorder, condition, or disease includes disorders related to the Ras-pathway, such as Ras-related cancers.

Adapter protein. As used herein, the term "adapter protein" means any protein that binds or is bound to a CalDAG-GEF or a cAMP-GEF protein, and facilitates localization of the bound CalDAG-GEF or cAMP-GEF at the plasma membrane, thereby facilitating Ras activation.

Variant. As used herein a "variant" sequence has, or will result in having, a sufficient amino acid similarity to have a reasonable expectation of success in the methods of the present invention. In order to produce variants of the disclosed sequences that may also functionally serve as a CalDAG-GEF or cAMP-GEF protein, any one or more of the naturally-occurring CalDAG-GEF or cAMP-GEF sequences disclosed herein may be used as a reference sequence to determine whether a candidate sequence possesses sufficient amino acid similarity to have a reasonable expectation of success in the methods of the present invention. Preferably, variant sequences are at least 70% similar or 60% identical, more preferably at least 75% similar or 65% identical, and most preferably 80% similar or 70% identical to one of the disclosed, naturally-occurring sequences.

To determine whether a candidate peptide region has the requisite percentage similarity or identity to a reference polypeptide or peptide oligomer, the candidate amino acid sequence and the reference amino acid sequence are first aligned using the dynamic programming algorithm described in Smith and Waterman (1981), *J. Mol. Biol.* 147:195–197, in combination with the BLOSUM62 substitution matrix described in FIG. 2 of Henikoff and Henikoff (1992), "Amino acid substitution matrices from protein blocks", *PNAS* (1992 November), 89:10915–10919. For the present invention, an appropriate value for the gap insertion penalty is –12, and an appropriate value for the gap extension penalty is –4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pairwise similarity score is zero; otherwise the pairwise similarity score is 1.0. The raw similarity score is the sum of the pairwise similarity scores of the aligned amino acids. The raw score is then normalized by dividing it by the number of amino acids in the smaller of the candidate or reference sequences. The normalized raw score is the percent similarity. Alternatively, to calculate a percent identity, the aligned amino acids of each sequence are again compared sequentially. If the amino acids are non-identical, the pairwise identity score is zero; otherwise the pairwise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

In all instances, variants of the naturally-occurring CalDAG-GEF or cAMP-GEF proteins, as described above, must be tested for biological activity as described below. Specifically, the proteins must exhibit guanine nucleotide exchange factor activity, and, preferably, they have the ability to inhibit Ras signaling of the Ras/Raf-1/MAP kinase pathway.

II. The CalDAG-GEFs

CalDAG-GEFI has a substrate specificity for Rap1A, dual binding domains for calcium ($Ca^{2+}$) and diacylglycerol (DAG), and enriched expression in brain basal ganglia pathways and their axon-terminal regions. Expression of CalDAG-GEFI activates Rap1A and inhibits Ras-dependent activation of the Erk/MAP kinase cascade in 293T cells. $Ca^{2+}$ ionophore and phorbol ester strongly and additively enhance this Rap1A activation. By contrast, CalDAG-GEFII exhibits a different brain expression pattern and fails to activate Rap1A, but activates H-Ras, R-Ras and the Erk/MAP kinase cascade under $Ca^{2+}$ and DAG modulation. The CalDAG-GEF proteins have a critical neuronal function in determining the relative activation of Ras and Rap1 signaling induced by $Ca^{2+}$ and DAG mobilization. The expression of CalDAG-GEFI and CalDAG-GEFII in hematopoietic organs indicates that such control has broad significance in Ras/Rap regulation of normal and malignant states.

The basal ganglia are centrally implicated in movement control and in forms of procedural learning related to habit formation. It is not yet known whether particular neurochemical specializations of the basal ganglia contribute to these behavioral functions. The basal ganglia do, however, have a unique double-inhibitory pathway design combined with abundant expression of neuromodulators in striatal neurons. A number of genes with differentially high expression in the striatum have also been identified. These include genes coding for proteins with signaling functions, such as adenylate cyclase V (Glatt et al., 361 NATURE (LONDON), 536–38 (1993)) and DARPP-32 (Hemmings et al., 310 NATURE (LONDON) 502–05 (1984)). To identify other cellular signaling molecules that could contribute to basal ganglia functions, a search for striatum-enriched transcripts was performed by a differential display method, as discussed in Example 1. Among the transcripts identified in this search were a family of genes characterized by the presence of a Ras superfamily (GEF) domain.

Figure 2C:
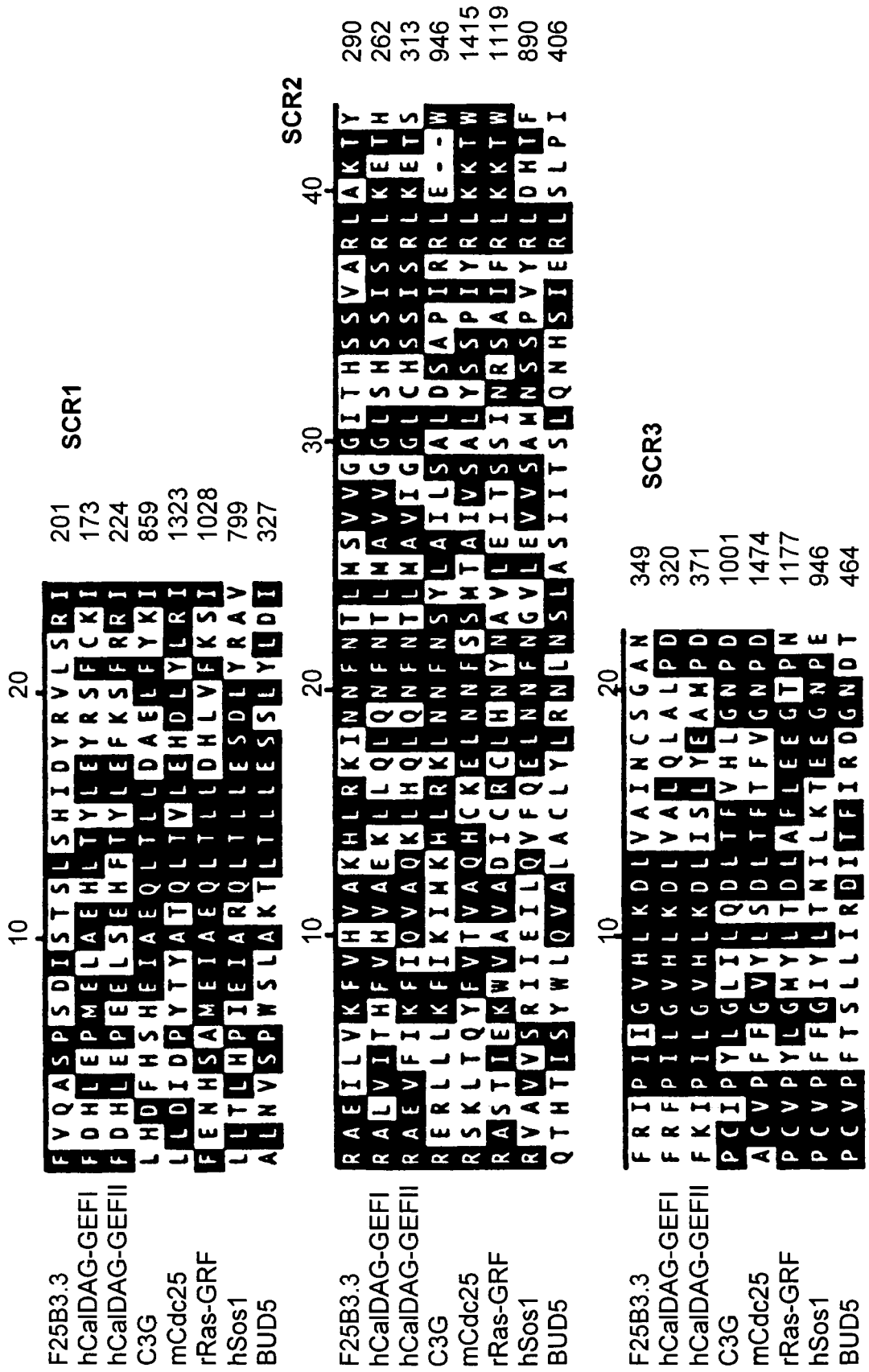
FIG. 2C shows multiple alignment of GEF structurally conserved regions (SCRs) of F25B3.3 (SEQ. ID NOS. 19, 20 and 21), hCalDAG-GEFI (SEQ. ID NO: 4: 150–173, 220–262 and 299–320), hCalDAG-GEFII (SEQ. ID NOS: 63, 65 and 67), C3G (SEQ. ID NOS. 22, 23 and 24), mCdc25 (SEQ. ID NOS. 25, 26 and 27), rRas-GRF (SEQ. ID NOS. 28, 29 and 30), hSos1 (SEQ. ID NOS. 31, 32 and 33), BUD5 (SEQ. ID NOS. 34, 35 and 36) and *C. elegans* (cel) (F25B3.3, GenBank accession number: 1262950)(SEQ. ID NO: 37).
Figure 3D:
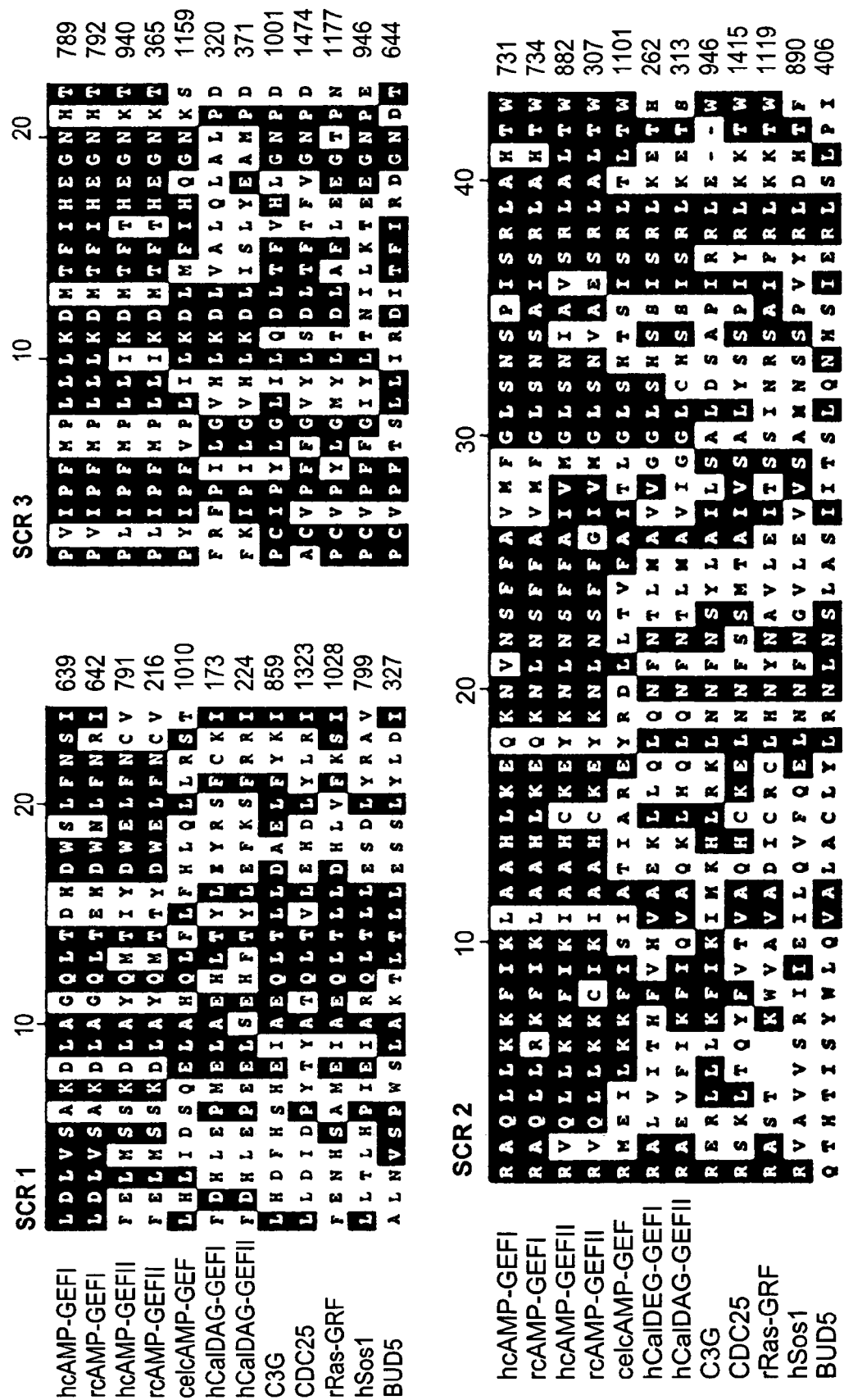
FIG. 3D shows the amino acid sequences of the structurally conserved regions (SCRs) of human (h) cAMP-GEFI (SEQ. ID NO: 12: 616–639, 689–731 and 768–789), rat (r) cAMP-GEFI (SEQ. ID NO: 10: 619–642, 692–734 and 771–792), human (h) cAMP-GEFII (SEQ. ID NO. 59: 768–791, 840–882 and 919–940), rat (r) cAMP-GEFII (SEQ. ID NOS: 62, 64 and 66), celcAMP-GEF (SEQ. ID NO: 47, 49 and 50), hCalDEG-GEFI (SEQ. ID NO: 4: 150–173, 219–262 and 298–320), hCalDAG-GEFII (SEQ. ID NOS: 63, 65 and 67), C3G (SEQ. ID NOS. 22, 23 and 24), CDC25 (SEQ. ID NOS. 25, 26 and 27), rRas-GRF (SEQ. ID NOS. 28, 29 and 30), hSos1 (SEQ. ID NOS. 31, 32 and 33), and BUD5 (SEQ. ID NOS. 34, 35 and 36).

Specific domains identified include structurally conserved GEF regions SCR1, SCR2, and SCR3, as shown in FIGS. 2C and 3D, and as shown in the following table.

TABLE 1

| Gene | SCR1 | SCR2 | SCR3 |
|---|---|---|---|
| hCalDAG-GEFI | SEQ ID NO.3: 608–679 | SEQ ID NO.3: 818–946 | SEQ ID NO.3: 1055–1120 |
|  | SEQ ID NO.4: 150–173 | SEQ ID NO.4: 220–262 | SEQ ID NO.4: 299–320 |
| hCalDAG-GEFII | SEQ ID NO.7: 704–775 | SEQ ID NO.7: 914–1042 | SEQ ID NO.7: 1151–1216 |
|  | SEQ ID NO.8: 201–224 | SEQ ID NO.8: 271–313 | SEQ ID NO.8: 350–371 |
| hcAMP-GEFI | SEQ ID NO.11: 2061–2132 | SEQ ID NO.11: 2280–2408 | SEQ ID NO.11: 2517–2612 |
|  | SEQ ID NO.12: 616–639 | SEQ ID NO.12: 689–731 | SEQ ID NO.12: 768–789 |
| reAMP-GEFI | SEQ ID NO.9: 2051–2122 | SEQ ID NO.9: 2270–2270 | SEQ ID NO.9: 2507–2572 |
|  | SEQ ID NO.10: 619–642 | SEQ ID NO.10: 692–734 | SEQ ID NO.10: 771–792 |
| heAMP-GEFII | SEQ ID NO.17: 2222–2293 |  |  |
|  | SEQ ID NO.18: 606–629 |  |  |
| reAMP-GEFII | SEQ ID NO.15: 144–215 |  |  |
|  | SEQ ID NO.16: 48–71 |  |  |

In addition, the EF hand and DAG-binding domains were identified as shown in FIGS. 2E and 2F, and as shown in the following table:

TABLE 2

| Gene | EF Hand Domain | DAG-Binding Domain |
|---|---|---|
| hCalDaG-GEFI | SEQ ID NO.3: 1457–1516 | SEQ ID NO.3: 1655–1804 |
|  | SEQ ID NO.4: 433–452 | SEQ ID NO.4: 499–548 |

TABLE 2-continued

| Gene | EF Hand Domain | DAG-Binding Domain |
| --- | --- | --- |
| hCalDAG-GEFII | SEQ ID NO.7:<br>1532–1591[444]<br>SEQ ID NO.8:<br>477–496 | SEQ ID NO.7:<br>1727–1875<br>SEQ ID NO.8:<br>542–591 |

Finally, the cAMP-binding domains were identified as shown in FIG. 3E, and as shown in the following table:

TABLE 3

| Gene | cAMP-Binding Domain |
| --- | --- |
| hcAMP-GEFI | SEQ ID NO.11:<br>906–1115<br>SEQ ID NO.12:<br>231–300 |
| rcAMP-GEFI | SEQ ID NO.9:<br>887–1096<br>SEQ ID NO.10:<br>231–300 |
| hcAMP-GEFII | SEQ ID NO.17:<br>1070–1279<br>SEQ ID NO.18:<br>222–291 |

III. The cAMP-GEFs

Cyclic adenosine 3',5'-monophosphate (cAMP) is a universal second messenger that induces a variety of physiological responses in eukaryotic cells ranging from growth, differentiation, and gene expression to secretion and neurotransmission. The cAMP second messenger system has also been centrally implicated in modulating synaptic function, neuroplasticity and learning and memory. Most of these effects have been attributed to the binding of cAMP to cAMP-dependent protein kinase (PKA), leading in turn to the activation of intracellular phosphorylation cascades. Reported herein is the identification of a new family of cAMP binding proteins that are differentially distributed in the brain and body organs and that are characterized by the presence of both a cAMP binding domain and a guanine nucleotide exchange factor (GEF) domain. These proteins, cAMP-GEFs, bind cAMP and selectively activate the Ras superfamily small G protein, Rap1A, in a cAMP-dependent but PKA-independent manner.

The general concept of cAMP signaling involves the sequential activation (or inhibition) of cAMP production by G proteins, the binding of cAMP to PKA, and the triggering of a series of downstream serine-threonine phosphorylation cascades. Viewed as the nearly exclusive target of cAMP binding in eukaryotic cells, PKA has been considered the essential effector molecule mediating a wide range of physiological effects of G protein/cAMP-triggered phosphorylation cascades. As the main cAMP effector, PKA has also been shown to function in the indirect coupling of the cAMP signal transduction system to other intracellular signaling cascades. The cAMP signaling system has also been strongly implicated in neuronal functions ranging from neurotransmitter-initiated signaling to neuroplasticity underlying development and memory, but PKA has not been clearly linked to all of these neuronal functions, and region-specific neuronal effects have been observed as well. The cAMP-GEF gene has a Ras superfamily GEF motif. Thus, the gene codes for a novel cAMP binding protein that directly couples the cAMP signal transduction system to Ras superfamily cascades.

IV. Preferred Embodiments

Based, in part, upon the discoveries disclosed and described herein, the following preferred embodiments of the present invention are provided.

1. Isolated Nucleic Acids

In one series of embodiments, the present invention provides isolated nucleic acids corresponding to, or relating to, the CalDAG-GEF or cAMP-GEF nucleic acid sequences disclosed herein. As described more fully below, these sequences include normal CalDAG-GEF and cAMP-GEF sequences from humans and other mammalian species, mutant CalDAG-GEF and cAMP-GEF sequences from humans and other mammalian species, homologous sequences from non-mammalian species such as Drosophila and C. elegans, subsets of these sequences useful as probes and PCR primers, subsets of these sequences encoding fragments of the CalDAG-GEF or cAMP-GEF proteins or corresponding to particular domains or polymorphic regions, complementary or antisense sequences corresponding to fragments of the CalDAG-GEF or cAMP-GEF genes, sequences in which the CalDAG-GEF and/or cAMP-GEF coding regions have been operably joined to exogenous regulatory regions, and sequences encoding fusion proteins of the portions of the CalDAG-GEF or cAMP-GEF proteins fused to other proteins useful as markers of expression, as "tags" for purification, or in screens and assays for proteins interacting with the CalDAG-GEFs and/or cAMP-GEFs.

Thus, in a first series of embodiments, isolated nucleic acid sequences are provided which encode normal versions of the CalDAG-GEF and cAMP-GEF proteins. Examples of such nucleic acid sequences are disclosed herein. These nucleic acids may be genomic sequences or may be cDNA sequences (e.g., SEQ ID NOs: 1, 3, 5, 7, 9, 11, 13, 15, and 17). Thus, for example, the invention provides nucleic acid sequences in which the alternative splice variants described herein are incorporated at the DNA level, thereby, enabling cells including these sequences to express only one of the alternative splice variants at each splice position. For example, a recombinant gene may be produced in which one of the splice variants of cAMP-GEF is incorporated into DNA such that cells having this recombinant gene can express only one of these variants. For purposes of reducing the size of a recombinant CalDAG-GEF or cAMP-GEF gene, a cDNA gene may be employed or various combinations of the introns and untranslated exons may be removed from a DNA construct. Such constructs may be particularly useful, as described below, in identifying compounds which can induce or repress the expression of the CalDAG-GEF or cAMP-GEF genes.

In addition to the disclosed CalDAG-GEF and/or cAMP-GEF sequences, one of ordinary skill in the art is now enabled to identify and isolate nucleic acids corresponding to CalDAG-GEF or cAMP-GEF genes or cDNAs which are allelic to the disclosed sequences or which are heterospecific homologues. Thus, the present invention provides isolated nucleic acids corresponding to these alleles and homologues, as well as various recombinant constructs derived from these sequences, by means which are well known in the art. Briefly, one of ordinary skill in the art may now screen preparations of genomic or cDNA, including samples prepared from individual organisms (e.g., human cancer patients or their family members) as well as bacterial, viral, yeast or other libraries of genomic or cDNA, using probes or PCR primers to identify allelic or homologous sequences. Because it is desirable to identify additional CalDAG-GEF and/or cAMP-GEF gene mutations which may contribute to the development of Ras-related cancers, because it is desirable to identify additional CalDAG-GEF and/or cAMP-GEF polymorphisms which are not mutant or have antitumorigenic effects, and because it is also desired to create a variety of animal models which may be used to study Ras-related cancers and screen for potential therapeutics, it is particularly contemplated that additional CalDAG-GEF and/or cAMP-GEF sequences will be isolated from other preparations or libraries of human nucleic acids and from preparations or libraries from animals including rats, mice, hamsters, guinea pigs, rabbits, dogs, cats, goats, sheep, pigs, and non-human primates. Furthermore, CalDAG-GEF and/or cAMP-GEF homologues from yeast or invertebrate species, including C. elegans and other nematodes, as well as Drosophila and other insects, may have particular utility for drug screening. For example, invertebrates bearing mutant CalDAG-GEF and/or cAMP-GEF homologues (or mammalian CalDAG-GEF and/or cAMP-GEF transgenes) which cause a rapidly occurring and easily scored phenotype (e.g., abnormal eye development after several days) can be used as screens for drugs which block the effect of the mutant gene. Such invertebrates may prove far more rapid and efficient for mass screenings than larger vertebrate animals. Once lead compounds are found through such screens, they may be tested in higher animals.

Depending upon the intended use, the present invention provides nucleic acid subsequences of the CalDAG-GEF and/or cAMP-GEF genes which may have lengths varying from 8–10 nucleotides (e.g., for use as PCR primers) to nearly the full size of the CalDAG-GEF and/or cAMP-GEF genes. Thus, the present invention provides isolated nucleic acids comprising sequences corresponding to at least 8, preferably at least 10, and more preferably at least 15 consecutive, nucleotides of the CalDAG-GEF and/or cAMP-GEF genes, as disclosed or otherwise enabled herein, or to their complements.

In another series of embodiments, the present invention provides for isolated nucleic acids encoding all or a portion of the CalDAG-GEF and/or cAMP-GEF proteins in the form of a fusion protein. In these embodiments, a nucleic acid regulatory region (endogenous or exogenous) is operably joined to a first coding region which is covalently joined in-frame to a second coding region. The CalDAG-GEF and/or cAMP-GEF sequences of the fusion protein may represent the first, second, or any additional coding regions. The CalDAG-GEF and/or cAMP-GEF sequences may be conserved or non-conserved domains and can be placed in any coding region for the fusion protein.

In another series of embodiments, the present invention provides isolated nucleic acids in the form of recombinant DNA constructs in which a marker or reporter gene (e.g., β-galactosidase, luciferase) is operably joined to the 5' regulatory region of a CalDAG-GEF and/or cAMP-GEF gene such that expression of the marker gene is under the control of the CalDAG-GEF and/or cAMP-GEF regulatory sequences. Such isolated nucleic acids may be used to produce cells, cell lines or transgenic animals which are useful in the identification of compounds which can, directly or indirectly, differentially affect the expression of the CalDAG-GEFs and/or cAMP-GEFs.

Finally, the isolated nucleic acids of the present invention include any of the above described sequences when included in vectors. Appropriate vectors include cloning vectors and expression vectors of all types, including plasmids, phagemids, cosmids, episomes, and the like, as well as integration vectors. The vectors may also include various marker genes (e.g., antibiotic resistance or susceptibility genes) which are useful in identifying cells successfully transformed therewith. In addition, the vectors may include regulatory sequences to which the nucleic acids of the invention are operably joined, and/or may also include coding regions such that the nucleic acids of the invention, when appropriately ligated into the vector, are expressed as fusion proteins. Such vectors may also include vectors for use in yeast "two hybrid," baculovirus, and phage-display systems.

2. Substantially Pure Proteins

The present invention provides for substantially pure preparations of the CalDAG-GEF and/or cAMP-GEF proteins, fragments of the CalDAG-GEF and/or cAMP-GEF proteins, and fusion proteins including the CalDAG-GEFs and/or cAMP-GEFs or fragments thereof. The proteins, fragments and fusions have utility, as described herein, in the generation of antibodies to normal and mutant CalDAG-GEFs and/or cAMP-GEFs, in the identification of CalDAG-GEF and/or cAMP-GEF binding proteins, and in diagnostic and therapeutic methods. Therefore, depending upon the intended use, the present invention provides substantially pure proteins or peptides comprising amino acid sequences which are subsequences of the complete CalDAG-GEF and/or cAMP-GEF proteins and which may have lengths varying from 4–8 amino acids (e.g., for use as immunogens), or 9–15 amino acids (e.g., for use in binding assays), to the complete CalDAG-GEF and/or cAMP-GEF proteins. Thus, the present invention provides substantially pure proteins or peptides comprising sequences corresponding to at least 4, preferably at least 9, more preferably at least 15 consecutive amino acids of the CalDAG-GEF and/or cAMP-GEF proteins, as disclosed or otherwise enabled herein.

Purification can be achieved using standard protein purification procedures including, but not limited to, gel-filtration chromatography, ion-exchange chromatography, high-performance liquid chromatography (RP-HPLC, ion-exchange HPLC, size-exclusion HPLC, high-performance chromatofocusing chromatography, hydrophobic interaction chromatography, immunoprecipitation, or immunoaffinity purification. Gel electrophoresis (e.g., PAGE, SDS-PAGE) can also be used to isolate a protein or peptide based on its molecular weight, charge properties, and hydrophobicity.

A CalDAG-GEF or cAMP-GEF protein, or a fragment thereof, may also be conveniently purified by creating a fusion protein including the desired CalDAG-GEF or cAMP-GEF sequence fused to another peptide such as an antigenic determinant or poly-His tag (e.g., QIAexpress vectors, (QIAGEN Corp., Chatsworth, Calif.)), or a larger protein (e.g. GST using the pGEX-27 vector (Amrad, USA) or green fluorescent protein using the Green Lantern vector (GIBCO/BRL. Gaithersburg, Md.)).

3. Antibodies to the CalDAG-GEF and/or cAMP-GEFs

The present invention also provides antibodies, and methods of making antibodies, which selectively bind to the CalDAG-GEF and/or cAMP-GEF proteins or fragments thereof. The antibodies of the invention have utility as laboratory reagents for, inter alia, immunoaffinity purification of the CalDAG-GEFs and/or cAMP-GEFs, Western blotting to identify cells or tissues expressing the CalDAG-GEFs and/or cAMP-GEFs, and immunocytochemistry or immunofluorescence techniques to establish the subcellular location of the protein.

The antibodies of the invention may be generated in a host using the entire CalDAG-GEF and/or cAMP-GEF proteins of the invention or using any CalDAG-GEF and/or cAMP-GEF epitope which is characteristic of that protein and which substantially distinguishes it from host proteins. Such epitopes may be identified by comparing sequences of, for example, 4–8 amino acid residues from a CalDAG-GEF and/or cAMP-GEF sequence to computer databases of protein sequences from the relevant host. Antibodies against highly conserved domains are expected to have the greatest utility for purification or identification of CalDAG-GEFs and/or cAMP-GEFs.

Amino acid residue positions which are potential antigenic sites in the CalDAG-GEF or cAMP-GEF proteins and which may be useful in generating the antibodies of the invention may be determined by using computer programs such as the IBI Pustell program. Other methods of choosing antigenic determinants are known in the art and may, of course, be employed. In addition, larger fragments (e.g, 9–15 residues) including some of these epitopes may also be employed. Even larger fragments, including, for example, entire functional domains or multiple functional domains may also be preferred. For an overview of antibody techniques, see *Antibody Engineering: A Practical Guide*, Borrebaek, ed., W.H. Freeman & Company, NY (1992), or *Antibody Engineering*, 2nd Ed., Borrebaek, ed., Oxford University Press, Oxford (1995).

The antibodies of the invention may be labelled or conjugated with other compounds or materials for diagnostic and/or therapeutic uses. For example, they may be coupled to radionuclides, fluorescent compounds, or enzymes for imaging or therapy, or to liposomes for the targeting of compounds contained in the liposomes to a specific tissue location.

4. Transformed Cell Lines

The present invention also provides for cells or cell lines, both prokaryotic and eukaryotic, which have been transformed or transfected with the nucleic acids of the present invention so as to cause clonal propagation of those nucleic acids and/or expression of the proteins or peptides encoded thereby. Such cells or cell lines will have utility not only in the propagation and production of the nucleic acids and proteins of the present invention but also, as further described herein, as model systems for diagnostic and therapeutic assays. As used herein, the term "transformed cell" is intended to embrace any cell, or the descendant of any cell, into which has been introduced any of the nucleic acids of the invention, whether by transformation, transfection, infection, electroporation, microinjection or other means. Methods of producing appropriate vectors, transforming cells with those vectors, and identifying transformants are well known in the art and are only briefly reviewed here (see, for example, Sambrook et al. (1989) *Molecular Cloning: A Laboratory Manual*, 2nd ed., Cold Spring Harbor Laboratory Press, Cold Spring Harbor, N.Y.).

Vectors may be introduced into the recipient or "host" cells by various methods well known in the art including, but not limited to, calcium phosphate transfection, strontium phosphate transfection, DEAE dextran transfection, electroporation, lipofection (e.g., Dosper Liposomal transfection reagent, Boehringer Mannheim, Germany), microinjection, ballistic insertion on micro-beads, protoplast fusion or, for viral or phage vectors, by infection with the recombinant virus or phage.

5. Transgenic Animal Models

The present invention also provides for the production of transgenic non-human animal models for the study of Ras-related cancers, for the screening of candidate pharmaceutical compounds, for the creation of explanted mammalian cell cultures (e.g., neuronal, glial, organotypic or mixed cell cultures) in which mutant or wild type CalDAG-GEF and/or cAMP-GEF sequences are expressed or in which the CalDAG-GEF and/or cAMP-GEF genes have been inactivated (e.g., "knock-out" deletions), and for the evaluation of potential therapeutic interventions.

Species suitable for use as animal models in the present invention include, but are not limited to, rats, mice, hamsters, guinea pigs, rabbits, dogs, cats, goats, sheep, pigs, and non-human primates (e.g., Rhesus monkeys, chimpanzees).

Various techniques for generating transgenic animals, as well as techniques for homologous recombination or gene targeting, are now widely accepted and practiced. See, for example, Hogan et al., Manipulating Mouse Embryo (1986). To create a transgene, the target sequence of interest (e.g., mutant or wild-type CalDAG-GEF or cAMP-GEF sequences) is typically ligated into a cloning site located downstream of a promoter element which will regulate the expression of RNA from the CalDAG-GEF or cAMP-GEF sequence. An alternate approach to creating a transgene is to use endogenous CalDAG-GEF or cAMP-GEF regulatory sequences to drive expression of the CalDAG-GEF or cAMP-GEF transgene.

6. Assays for Drugs Which Affect CalDAG-GEF and/or cAMP-GEF Expression

In another series of embodiments, the present invention provides assays for identifying small molecules or other compounds which are capable of inducing or inhibiting the expression of the CalDAG-GEF or cAMP-GEF genes and proteins. The assays may be performed in vitro using non-transformed cells, immortalized cell lines, or recombinant cell lines, or in vivo using the transgenic animal models enabled herein.

In particular, the assays may detect the presence of increased or decreased expression of CalDAG-GEF, cAMP-GEF, or other CalDAG-GEF or cAMP-GEF-related genes or proteins, on the basis of increased or decreased mRNA expression (using, e.g., the nucleic acid probes disclosed and enabled herein), increased or decreased levels of CalDAG-GEF, cAMP-GEF or other CalDAG-GEF or cAMP-GEF-related protein products (using, e.g., the anti-CalDAG-GEF of anti-cAMP-GEF antibodies disclosed and enabled herein), or increased or decreased levels of expression of a marker gene (e.g., β-galactosidase or luciferase) operably joined to a CalDAG-GEF or cAMP-GEF 5' regulatory region in a recombinant construct.

Thus, for example, one may culture cells known to express a particular CalDAG-GEF or cAMP-GEF and add to the culture medium one or more test compounds. After allowing a sufficient period of time (e.g., 0–72 hours) for the compound to induce or inhibit the expression of the CalDAG-GEF or cAMP-GEF, any change in levels of expression from an established baseline may be detected using any of the techniques described above and well known in the art. In particularly preferred embodiments, the cells are from an immortalized cell line such as a human neuroblastoma, glioblastoma or a hybridoma cell line. Using the nucleic acid probes and/or antibodies disclosed and enabled herein, detection of changes in the expression of a CalDAG-GEF or cAMP-GEF and thus, identification of the compound as an inducer or repressor of CalDAG-GEF and/or cAMP-GEF expression, requires only routine experimentation.

In particularly preferred embodiments, a recombinant assay is employed in which a reporter gene such a β-galactosidase, green fluorescent protein, alkaline phosphatase, or luciferase is operably joined to a 5' regulatory region of a CalDAG-GEF or cAMP-GEF gene. The reporter gene and regulatory regions are joined in-frame (or in each of the three possible reading frames) so that transcription and translation of the reporter gene may proceed under the control of the CalDAG-GEF or cAMP-GEF regulatory elements. The recombinant construct may then be introduced into any appropriate cell type, although mammalian cells are preferred, and human cells are most preferred. The transformed cells may be grown in culture and, after establishing the baseline level of expression of the reporter gene, test compounds may be added to the medium. The ease of detection of the expression of the reporter gene provides for a rapid, high through-put assay for the identification of inducers and repressors of the CalDAG-GEF or cAMP-GEF gene.

Compounds identified by this method will have potential utility in modifying the expression of the CalDAG-GEF, cAMP-GEF or other CalDAG-GEF or cAMP-GEF-related genes in vivo. These compounds may be further tested in the animal models disclosed and enabled herein to identify those compounds having the most potent in vivo effects. In addition, as described herein with respect to small molecules having CalDAG-GEF or cAMP-GEF-binding activity, these molecules may serve as "lead compounds" for the further development of pharmaceuticals by, for example, subjecting the compounds to sequential modifications, molecular modeling, and other routine procedures employed in rational drug design.

7. Identification of Compounds with CalDAG-GEF and/or cAMP-GEF Binding Capacity

In light of the present disclosure, one of ordinary skill in the art is enabled to practice new screening methodologies which will be useful in the identification of proteins and other compounds which bind to, or otherwise directly interact with, the CalDAG-GEFs or cAMP-GEFs. The proteins and compounds will include endogenous cellular components which interact with the CalDAG-GEFs or cAMP-GEFs in vivo and which, therefore, provide new targets for pharmaceutical and therapeutic interventions, as well as recombinant, synthetic and otherwise exogenous compounds which may have CalDAG-GEF or cAMP-GEF binding capacity and, therefore, may be candidates for pharmaceutical agents. Thus, in one series of embodiments, cell lysates or tissue homogenates (e.g., human brain homogenates, leukocyte lysates) may be screened for proteins or other compounds which bind to one of the normal or mutant CalDAG-GEFs and/or cAMP-GEFs. Alternatively, any of a variety of exogenous compounds, both naturally occurring and/or synthetic (e.g., libraries of small molecules or peptides), may be screened for CalDAG-GEF or cAMP-GEF binding capacity. Small molecules are particularly preferred in this context because they are more readily absorbed after oral administration, have fewer potential antigenic determinants, and/or are more likely to cross the blood brain barrier than larger molecules such as nucleic acids or proteins. The methods of the present invention are particularly useful in that they may be used to identify molecules which selectively or preferentially bind to a mutant form of a CalDAG-GEF or cAMP-GEF protein (rather than a normal form) and, therefore, may have particular utility in treating the heterozygous victims of a CalDAG-GEF or cAMP-GEF associated disorder.

Compounds which bind to normal, mutant or both forms of the CalDAG-GEFs or cAMP-GEFs may have utility in treatments and diagnostics. Compounds which bind only to a normal CalDAG-GEF or cAMP-GEF may, for example, act as enhancers of its normal activity and thereby at least partially compensate for the lost or abnormal activity of mutant forms of the CalDAG-GEF or cAMP-GEF in victims suffering from CalDAG-GEF- or cAMP-GEF-associated disorders. Compounds which bind to both normal and mutant forms of a CalDAG-GEF or cAMP-GEF may have utility if they differentially affect the activities of the two forms so as to alleviate the overall departure from normal function. Alternatively, blocking the activity of both normal and mutant forms of either CalDAG-GEF or cAMP-GEF may have less severe physiological and clinical consequences than the normal progress of the disorder and, therefore, compounds which bind to and inhibit the activity of both normal and mutant forms of a CalDAG-GEF or cAMP-GEF may be therapeutically useful. Preferably, however, compounds are identified which have a higher affinity of binding to mutant CalDAG-GEF or cAMP-GEF than to normal CalDAG-GEF or cAMP-GEF, and which selectively or preferentially inhibit the activity of the mutant form. Such compounds may be identified by using any of the techniques described herein, and then comparing the binding affinities of the candidate compound(s) for the normal and mutant forms of CalDAG-GEF or cAMP-GEF.

The effect of agents which bind to the CalDAG-GEFs or cAMP-GEFs (normal or mutant forms of either) can be monitored either by direct monitoring of this binding (e.g., using the BIAcore assay, LKB Pharmacia, Sweden) or by indirect monitoring of binding by detecting, for example, a change in fluorescence, molecular weight, or concentration of either the binding agent or CalDAG-GEF or cAMP-GEF component, either in a soluble phase or in a substrate-bound phase.

Once identified by the methods described above, the candidate compounds may then be produced in quantities sufficient for pharmaceutical administration or testing (e.g., $\mu$g or mg or greater quantities), and formulated in a pharmaceutically acceptable carrier (see, e.g., REMINGTON'S PHARMACEUTICAL SCIENCES, Gennaro, A., ed., Mack Pub., (1990)). These candidate compounds may then be administered to the transformed cells of the invention, to the transgenic animal models of the invention, to cell lines derived from the animal models or from human patients, or to patients with CalDAG-GEF- or cAMP-GEF-associated disorders. The animal models described and enabled herein are of particular utility in further testing candidate compounds which bind to normal or mutant CalDAG-GEF or cAMP-GEF for their therapeutic efficacy.

In addition, once identified by the methods described above, the candidate compounds may also serve as "lead compounds" in the design and development of new pharmaceuticals. For example, as in well known in the art, sequential modification of small molecules (e.g., amino acid residue replacement for peptides; functional group replacement for peptide or non-peptide compounds) is a standard approach in the pharmaceutical industry for the development of new pharmaceuticals. Such development generally proceeds from a "lead compound" which is shown to have at least some of the activity (e.g., CalDAG-GEF or cAMP-GEF binding or blocking ability) of the desired pharmaceutical. In particular, when one or more compounds having at least some activity of interest (e.g., modulation of CalDAG-GEF or cAMP-GEF activity) are identified, structural comparison of the molecules can greatly inform the skilled practitioner by suggesting portions of the lead compounds which should be conserved and portions which may be varied in the design of new candidate compounds. Thus, the present invention also provides a means of identifying lead compounds which may be sequentially modified to produce new candidate compounds for use in the treatment or CalDAG-GEF- or cAMP-GEF-associated disorders. These new compounds then may be tested both for CalDAG-GEF or cAMP-GEF-binding or blocking (e.g., in the binding assays described above) and for therapeutic efficacy (e.g., in the animal models described herein). This procedure may be iterated until compounds having the desired therapeutic activity and/or efficacy are identified.

In each of the present series of embodiments, an assay is conducted to detect binding between a "CalDAG-GEF component" or a "cAMP-GEF component" and some other moiety. Of particular utility will be sequential assays in which compounds are tested for the ability to bind to only the normal or only the mutant forms of the CalDAG-GEF or cAMP-GEF functional domains using mutant and normal CalDAG-GEF or cAMP-GEF components in the binding assays. Such compounds are expected to have the greatest therapeutic utilities, as described more fully below. The "CalDAG-GEF component" or the "cAMP-GEF component" in these assays may be a complete normal or mutant form of a CalDAG-GEF or cAMP-GEF protein (e.g., an hCalDAG-GEF or hcAMP-GEF variant) but need not be, or a specific domain of a CalDAG-GEF or cAMP-GEF. Rather, particular functional domains of the CalDAG-GEFs or cAMP-GEFs, as described above, may be employed either as separate molecules or as part of a fusion protein. For example, to isolate proteins or compounds that interact with these functional domains, screening may be carried out using fusion constructs and/or synthetic peptides corresponding to these regions. Obviously, various combinations of fusion proteins and functional domains from CalDAG-GEF or cAMP-GEF are possible. In addition, the functional domains may be altered so as to aid in the assay by, for example, introducing into the functional domain a reactive group or amino acid residue (e.g., cysteine) which will facilitate immobilization of the domain on a substrate (e.g., using sulfhydryl reactions).

Methods for screening cellular lysates, tissue homogenates, or small molecule libraries for candidate CalDAG-GEF or cAMP-GEF-binding molecules are well known in the art and, in light of the present disclosure, may now be employed to identify compounds which bind to normal or mutant CalDAG-GEF or cAMP-GEF components or which modulate CalDAG-GEF or cAMP-GEF activity as defined by non-specific measures (e.g., changes in intracellular $Ca^{2+}$, GTP/GDP ratio) or by specific measures (e.g., changes in the expression of other downstream genes which can be monitored by differential display, 2D gel electrophoresis, differential hybridization, or SAGE methods). The preferred methods involve variations on the following techniques: (1) direct extraction by affinity chromatography; (2) co-isolation of CalDAG-GEF or cAMP-GEF components and bound proteins or other compounds by immunoprecipitation; (3) the Biomolecular Interaction Assay (BIAcore); and (4) the yeast two-hybrid systems. These and others are discussed separately below.

A. Affinity Chromatography

In light of the present disclosure, a variety of affinity binding techniques well known in the art may be employed to isolate proteins or other compounds which bind to the CalDAG-GEFs or cAMP-GEFs disclosed or otherwise enabled herein. In general, a CalDAG-GEF or cAMP-GEF component may be immobilized on a substrate (e.g., a column or filter) and a solution including the test compound(s) is contacted with the CalDAG-GEF or cAMP-GEF protein, fusion or fragment under conditions which are permissive for binding. The substrate is then washed with a solution to remove unbound or weakly bound molecules. A second wash may then elute those compounds which strongly bound to the immobilized normal or mutant CalDAG-GEF or cAMP-GEF component. Alternatively, the test compounds may be immobilized and a solution containing one or more CalDAG-GEF or cAMP-GEF components may be contacted with the column, filter, or other substrate. The ability of the CalDAG-GEF or cAMP-GEF component to bind to the test compounds may be determined as above or a labeled form of the CalDAG-GEF or cAMP-GEF component (e.g., a radio-labeled or chemiluminescent functional domain) may be used to more rapidly assess binding to the substrate-immobilized compound(s).

B. Co-Immunoprecipitation

Another well characterized technique for the isolation of the CalDAG-GEF or cAMP-GEF components and their associated proteins or other compounds is direct immunoprecipitation with antibodies. This procedure has been successfully used, for example, to isolate many of the synaptic vesicle associated proteins (Phizicky et al., 59 J. BIOL. CHEM. 94–123 (1994)). Thus, either normal or mutant CalDAG-GEF or cAMP-GEF components may be mixed in a solution with the candidate compound(s) under conditions which are permissive for binding, and the CalDAG-GEF or cAMP-GEF component may be immunoprecipitated. Proteins or other compounds which co-immunoprecipitate with the CalDAG-GEF or cAMP-GEF component may then be identified by standard techniques as described above. General techniques for immunoprecipitation may be found in, for example, Harlow et al., ANTIBODIES: A LABORATORY MANUAL (1988).

The antibodies employed in this assay, as described and enabled herein, may be polyclonal or monoclonal, and include the various antibody fragments as well as single chain antibodies, and the like.

C. The Biomolecular Interaction Assay

Another useful method for the detection and isolation of binding proteins is the Biomolecular Interaction Assay or "BIAcore" system developed by Pharmacia Biosensor and described in the manufacturer's protocol (LKB Pharmacia, Sweden). In light of the present disclosure, one of ordinary skill in the art is now enabled to employ this system, or a substantial equivalent, to identify proteins or other compounds having CalDAG-GEF or cAMP-GEF binding capacity. The BIAcore system uses an affinity purified anti-GST antibody to immobilize GST-fusion proteins onto a sensor chip. Obviously, other fusion proteins and corresponding antibodies may be substituted. The sensor utilizes surface plasmon resonance which is an optical phenomenon that detects changes in refractive indices. A homogenate of a tissue of interest is passed over the immobilized fusion protein and protein—protein interactions are registered as changes in the refractive index. This system can be used to determine the kinetics of binding and to assess whether any observed binding is of physiological relevance.

D. The Yeast Two-Hybrid System

The yeast "two-hybrid" system takes advantage of transcriptional factors that are composed of two physically separable, functional domains. One commonly used system employs the yeast GAL4 transcriptional activator, consisting of a DNA binding domain and a transcriptional activation domain. Two different cloning vectors are used to generate separate fusions of the GAL4 domains to genes encoding potential binding proteins. The fusion proteins are co-expressed, targeted to the nucleus and, if interactions occur, activation of a reporter gene (e.g., lacZ) produces a detectable phenotype.

E. Other Methods

The nucleotide sequences and protein products, including both mutant and normal forms of these nucleic acids and their corresponding proteins, can be used with the above techniques to isolate other interacting proteins, and to identify other genes whose expression is altered by the over-expression of normal CalDAG-GEF or cAMP-GEF sequences, by the under-expression of normal CalDAG-GEFs or cAMP-GEFs sequences, or by the expression of mutant CalDAG-GEF and/or cAMP-GEF sequences. Identification of these interacting proteins, as well as the identification of other genes whose expression levels are altered in the face of mutant CalDAG-GEF or cAMP-GEF sequences (for instance) will identify other gene targets which have direct relevance to the pathogenesis of this disease in its clinical or pathological forms. Specifically, these techniques rely on PCR-based and/or hybridization-based methods to identify genes which are differentially expressed between two conditions (a cell line expressing normal CalDAG-GEFs or cAMP-GEFs compared to the same cell type expressing a mutant CalDAG-GEF or cAMP-GEF sequence). These techniques include differential display, serial analysis of gene expression (SAGE), mass-spectrometry of protein, 2D-gels and subtractive hybridization (See, e.g., Nowak, 270 Sci. 368–371 (1995); Kahn, 270 Sci. 369–370 (1995)).

8. Methods of Identifying Compounds Modulating CalDAG-GEF and/or cAMP-GEF Activity In another series of embodiments, the present invention provides for methods of identifying compounds with the ability to modulate the activity of normal and mutant CalDAG-GEFs and/or cAMP-GEFs. As used with respect to this series of embodiments, the term "activity" broadly includes gene and protein expression, CalDAG-GEF and/or cAMP-GEF protein post-translation processing, trafficking and localization, and any functional activity (e.g., enzymatic, receptor-effector, binding, channel), as well as downstream affects of any of these. Using the transformed cells and transgenic animal models of the present invention, cells obtained from subjects bearing a mutant CalDAG-GEF and/or cAMP-GEF gene, or animals or human subjects bearing naturally occurring CalDAG-GEF and/or cAMP-GEF mutations, it is now possible to screen candidate pharmaceuticals and treatments for their therapeutic effects by detecting changes in one or more of the functional characteristics or phenotypic manifestations of normal or mutant CalDAG-GEF and/or cAMP-GEF expression.

Thus, the present invention provides methods for screening or assaying for proteins, small molecules or other compounds which modulate CalDAG-GEF and/or cAMP-GEF activity by contacting a cell in vivo or in vitro with a candidate compound and assaying for a change in a marker associated with normal or mutant CalDAG-GEF and/or cAMP-GEF activity. The marker associated with CalDAG-GEF and/or cAMP-GEF activity may be any measurable biochemical, physiological, histological and/or behavioral characteristic associated with CalDAG-GEF and/or cAMP-GEF expression. In particular, useful markers will include any measurable biochemical, physiological, histological and/or behavioral characteristic which distinguishes cells, tissues, animals or individuals bearing at least one mutant CalDAG-GEF and/or cAMP-GEF gene from their normal counterparts. In addition, the marker may be any specific or non-specific measure of CalDAG-GEF and/or cAMP-GEF activity, such as the GDP/GTP bound to Rap1/Ras. CalDAG-GEF and/or cAMP-GEF specific measures include measures of CalDAG-GEF and/or cAMP-GEF expression (e.g., CalDAG-GEF and/or cAMP-GEF mRNA or protein levels) which may employ the nucleic acid probes or antibodies of the present invention. Non-specific measures include changes in cell physiology such as pH, intracellular calcium, cAMP levels, overall GTP/GDP ratios, phosphatidylinositol activity, protein phosphorylation, etc., which can be monitored by known methods. The activation or inhibition of CalDAG-GEF or cAMP-GEF activity in its mutant or normal form can also be monitored by examining changes in the expression of other genes which are specific to the CalDAG-GEF and/or cAMP-GEF pathway. These can be assayed by such techniques as differential display, differential hybridization, and SAGE, as well as by 2-D gel electrophoresis of cellular lysates. In each case, the differentially-expressed genes can be ascertained by inspection of identical studies before and after application of the candidate compound. Furthermore, as noted elsewhere, the particular genes whose expression is modulated by the administration of the candidate compound can be ascertained by cloning, nucleotide sequencing, amino acid sequencing, or mass spectrometry.

In general, a cell may be contacted with a candidate compound and, after an appropriate period (e.g., 0–72 hours for most biochemical measures of cultured cells), the marker of CalDAG-GEF or cAMP-GEF activity may be assayed and compared to a baseline measurement. The baseline measurement may be made prior to contacting the cell with the candidate compound or may be an external baseline established by other experiments or known in the art. The cell may be a transformed cell of the present invention or an explant from an animal or individual. In particular, the cell may be an explant from a carrier of a CalDAG-GEF or cAMP-GEF mutation or an animal model of the invention (e.g., a transgenic nematode or mouse bearing a mutant CalDAG-GEF or cAMP-GEF gene). Preferred cells include those from neurological tissues such as neuronal, glial or mixed cell cultures; and cultured fibroblasts, liver, kidney, spleen, or bone marrow. The cells may be contacted with the candidate compounds in a culture in vitro or may be administered in vivo to a live animal or human subject. For live animals or human subjects, the test compound may be administered orally or by any parenteral route suitable to the compound. For clinical trials of human subjects, measurements may be conducted periodically (e.g., daily, weekly or monthly) for several months or years.

In light of the identification, characterization, and disclosure herein of the CalDAG-GEF or cAMP-GEF genes and proteins, the CalDAG-GEF or cAMP-GEF nucleic acid probes and antibodies, and the CalDAG-GEF or cAMP-GEF transformed cells and transgenic animals of the invention, one of ordinary skill in the art is now enabled by perform a great variety of assays which will detect the modulation of CalDAG-GEF or cAMP-GEF activity by candidate compounds. Particularly preferred and contemplated embodiments are discussed in some detail below.

A. CalDAG-GEF and/or cAMP-GEF Expression

In one series of embodiments, specific measures of CalDAG-GEF or cAMP-GEF expression are employed to screen candidate compounds for their ability to affect CalDAG-GEF or cAMP-GEF activity. Thus, using the CalDAG-GEF or cAMP-GEF nucleic acids and antibodies disclosed and otherwise enabled herein, one may use mRNA levels or protein levels as a marker for the ability of a candidate compound to modulate CalDAG-GEF or cAMP-GEF activity. The use of such probes and antibodies to measure gene and protein expression is well known in the art and discussed elsewhere herein.

B. Intracellular Localization

In another series of embodiments, compounds may be screened for their ability to modulate the activity of the CalDAG-GEFs or cAMP-GEFs based upon their effects on the trafficking and intracellular localization of the CalDAG-GEFs or cAMP-GEFs. Differences in localization of mutant and normal CalDAG-GEFs and/or cAMP-GEFs may contribute to the etiology of CalDAG-GEF and/or cAMP-GEF-associated diseases. Compounds which can affect the localization of the CalDAG-GEFs and/or cAMP-GEFs may, therefore, be identified as potential therapeutics. Standard techniques known in the art may be employed to detect the localization of the CalDAG-GEFs and/or cAMP-GEFs. Generally, these techniques will employ the antibodies of the present invention, and in particular antibodies which selectively bind to one or more mutant CalDAG-GEFs or cAMP-GEFs but not to normal CalDAG-GEFs or cAMP-GEFs. As is well known in the art, such antibodies may be labeled by any of a variety of techniques (e.g., fluorescent or radioactive tags, labeled secondary antibodies, avidin-biotin, etc.) to aid in visualizing the intracellular location of the CalDAG-GEFs or cAMP-GEFs. The CalDAG-GEFs or cAMP-GEFs may be co-localized to particular structures, as is known in the art, using antibodies to markers of those structures (e.g., TGN38 for the Golgi, transferrin receptor for post-Golgi transport vesicles, LAMP2 for lysosomes). Western blots of purified fractions from cell lysates enriched for different intracellular membrane bound organelles (e.g., lysosomes, synaptosomes, Golgi) may also be employed. In addition, the relative orientation of different domains of the CalDAG-GEFs and/or cAMP-GEFs across cellular domains may be assayed using, for example, electron microscopy and antibodies raised to those domains.

9. Screening and Diagnostics for CalDAG-GEF- or cAMP-GEF-associated disorders

A. General Diagnostic Methods

The CalDAG-GEF or cAMP-GEF genes and gene products, as well as the CalDAG-GEF or cAMP-GEF-derived probes, primers and antibodies, disclosed or otherwise enabled herein, are useful in the screening for carriers of alleles associated with CalDAG-GEF- or cAMP-GEF-associated disorders. Individuals at risk for such a disorder or individuals not previously known to be at risk, may be routinely screened using probes to detect the presence of a mutant CalDAG-GEF or cAMP-GEF gene or protein by a variety of techniques. Diagnosis of inherited cases of these diseases can be accomplished by methods based upon the nucleic acids (including genomic and mRNA/cDNA sequences), proteins, and/or antibodies disclosed and enabled herein, including functional assays designed to detect increases or decreases of the normal CalDAG-GEF or cAMP-GEF activity and/or the presence of specific new activities conferred by the mutant CalDAG-GEFs or cAMP-GEFs. Preferably, the methods and products are based upon the human CalDAG-GEF or cAMP-GEF nucleic acids, proteins or antibodies, as disclosed or otherwise enabled herein. For brevity of exposition, but without limiting the scope of the invention, the following description will focus upon uses of the human homologues of CalDAG-GEF and cAMP-GEF. It will be understood, however, that homologous sequences from other species, including those disclosed herein, will be equivalent for many purposes.

B. Protein Based Screens and Diagnostics

When a diagnostic assay is to be based upon CalDAG-GEF or cAMP-GEF proteins, a variety of approaches are possible. For example, diagnosis can be achieved by monitoring differences in the electrophoretic mobility of normal and mutant proteins. Such an approach will be particularly useful in identifying mutants in which insertions, deletions or substitutions have resulted in a significant change in the electrophoretic migration of the resultant protein. Alternatively, diagnosis may be based upon differences in the proteolytic cleavage patterns of normal and mutant proteins, differences in molar ratios of the various amino acid residues, or by functional assays demonstrating altered function of the gene products.

C. Nucleic Acid Based Screens and Diagnostics

When the diagnostic assay is to be based upon nucleic acids from a sample, the assay may be based upon mRNA, cDNA or genomic DNA. Whether mRNA, cDNA, or genomic DNA is assayed, standard methods well known in the art may be used to detect the presence of a particular sequence either in situ or in vitro (See, e.g., Sambrook et al., MOLECULAR CLONING: A LABORATORY MANUAL, 2nd ed. (1989)).

(1) Appropriate Probes and Primers

Whether for hybridization, RNase protection, ligase-mediated detection, PCR amplification or any other standards methods described herein and well known in the art, a variety of subsequences of the CalDAG-GEF and/or cAMP-GEF sequences disclosed or otherwise enabled herein will be useful as probes and/or primers. These sequences or subsequences will include both normal CalDAG-GEF or cAMP-GEF sequences and deleterious mutant sequences. In general, useful sequences will include at least 8–10, more preferably 10–15, and most preferably 15–25 consecutive nucleotides from the CalDAG-GEF or cAMP-GEF introns, exons or intron/exon boundaries. Useful sequences will also include at least 25–500 consecutive nucleotides from the CalDAG-GEF or cAMP-GEF introns, exons or intron/exon boundaries. Depending upon the target sequence, the specificity required, and future technological developments, shorter sequences may also have utility. Therefore, any CalDAG-GEF or cAMP-GEF derived sequence which is employed to isolate, clone, amplify, identify or otherwise manipulate a CalDAG-GEF or cAMP-GEF sequence may be regarded as an appropriate probe or primer.

(2) Hybridization Screening

For in situ detection of a normal or mutant CalDAG-GEF, cAMP-GEF or other CalDAG-GEF and/or cAMP-GEF-associated nucleic acid sequence, a sample of tissue may be prepared by standard techniques and then contacted with one or more of the above-described probes, preferably one which is labeled to facilitate detection, and an assay for nucleic acid hybridization is conducted under stringent conditions which permit hybridization only between the probe and highly or perfectly complementary sequences.

(3) Restriction Mapping

Sequence alterations may also create or destroy fortuitous restriction enzyme recognition sites which are revealed by the use of appropriate enzyme digestion followed by electrophoresis and visualization. DNA fragments carrying the site (normal or mutant) are detected by their increase or reduction in size, or by the increase or decrease of corresponding restriction fragment numbers. Such restriction fragment length polymorphism analysis (RFLP), or restriction mapping, may be employed with genomic DNA, mRNA or cDNA. The CalDAG-GEF or cAMP-GEF sequences may be amplified by PCR using the above-described primers prior to restriction, in which case the lengths of the PCR products may indicate the presence or absence of particular restriction sites, and/or may be subjected to restriction after amplification. The CalDAG-GEF or cAMP-GEF fragments may be visualized by any convenient means (e.g., under UV light in the presence of ethidium bromide).

(4) PCR Mapping

In another series of embodiments, a single base substitution mutation may be detected based on differential PCR product length or production in PCR. Thus, primers which span mutant sites or which, preferably, have 3' termini at mutation sites, may be employed to amplify a sample of genomic DNA, mRNA or cDNA from a subject. A mismatch at a mutational site may be expected to alter the ability of the normal or mutant primers to promote the polymerase reaction and, thereby, result in product profiles which differ between normal subjects and heterozygous and/or homozygous CalDAG-GEF or cAMP-GEF mutants.

(5) Electrophoretic Mobility

Genetic testing based on DNA sequence differences also may be achieved by detection of alterations in electrophoretic mobility of DNA, mRNA or cDNA fragments in gels. Small sequence deletions and insertions, for example, can be visualized by high resolution gel electrophoresis of single or double stranded DNA, or as changes in the migration pattern of DNA heteroduplexes in non-denaturing gel electrophoresis.

(6) Chemical Cleavage of Mismatches

Mutations in the CalDAG-GEFs or cAMP-GEFs may also be detected by employing the chemical cleavage of mismatch (CCM) method (See, e.g., Saleeba et al., METHODS IN ENZYMOLOGY, 217: 286–295 (1993)). In this technique, probes (up to ~1 kb) may be mixed with a sample of genomic DNA, cDNA or mRNA obtained from a subject. The sample and probes are mixed and subjected to conditions which allow for heteroduplex formation (if any). Preferably, both the probe and sample nucleic acids are double-stranded, or the probe and sample may be PCR amplified together, to ensure creation of all possible mismatch heteroduplexes. Mismatched T residues are reactive to osmium tetroxide and mismatched C residues are reactive to hydroxylamine. Because each mismatched A will be accompanied by a mismatched T, and each mismatched G will be accompanied by a mismatched C, any nucleotide differences between the probe and sample (including small insertions or deletions) will lead to the formation of at least one reactive heteroduplex. After treatment with osmium tetroxide and/or hydroxylamine to modify any mismatch sites, the mixture is subjected to chemical cleavage at any modified mismatch sites by, for example, reaction with piperidine. The mixture may then be analyzed by standard techniques such as gel electrophoresis to detect cleavage products which would indicate mismatches between the probe and sample.

(7) Other Methods

Various other methods of detecting CalDAG-GEF or cAMP-GEF mutations, based upon the CalDAG-GEF or cAMP-GEF sequences disclosed and otherwise enabled herein, will be apparent to those of ordinary skill in the art. Any of these may be employed in accordance with the present invention. These include, but are not limited to, nuclease protection assays (S 1 or ligase-mediated), ligated PCR, denaturing gradient gel electrophoresis (DGGE; see, e.g., Fischer et al., 80 PROC. NAT'L ACAD. SCI (USA), 1578–83 (1983)), restriction endonuclease fingerprinting combined with SSCP (REF-SSCP; see, e.g., Liu et al., 18 BIOTECHNIQUES 470–79 (1995)), and the like.

D. Other Screens and Diagnostics

Diagnosis also can be made by observation of alterations in CalDAG-GEF or cAMP-GEF transcription, translation, and post-translational modification and processing as well as alterations in the intracellular and extracellular trafficking of CalDAG-GEF or cAMP-GEF gene products in the brain and peripheral cells. Such changes will include alterations in the amount of CalDAG-GEF or cAMP-GEF messenger RNA and/or protein, alteration in phosphorylation state, abnormal intracellular location/distribution, abnormal extracellular distribution, etc. Such assays will include: Northern Blots (with CalDAG-GEF or cAMP-GEF-specific and non-specific nucleotide probes), Western blots and enzyme-linked immunosorbent assays (ELISA) (with antibodies raised specifically to a CalDAG-GEF or a cAMP-GEF functional domain, including various post-translational modification states).

E. Screening and Diagnostic Kits

In accordance with the present invention, diagnostic kits are also provided which will include the reagents necessary for the above-described diagnostic screens. For example, kits may be provided which include antibodies or sets of antibodies which are specific to one or more mutant epitopes. These antibodies may, in particular, be labeled by any of the standard means which facilitate visualization of binding. Alternatively, kits may be provided in which oligonucleotide probes or PCR primers, as described above, are present for the detection and/or amplification of mutant CalDAG-GEF, cAMP-GEF or other CalDAG-GEF and/or cAMP-GEF-associated nucleotide sequences. Again, such probes may be labeled for easier detection of specific hybridization. As appropriate to the various diagnostic embodiments described above, the oligonucleotide probes or antibodies in such kits may be immobilized to substrates and appropriate controls may be provided.

10. Methods of Treatment

The present invention now provides a basis for therapeutic intervention in diseases which are associated to the CalDAG-GEFs or cAMP-GEFs in that they are caused, prevented, exacerbated, or alleviated, or which may be caused, prevented, exacerbated, or alleviated, by the either normal or mutant CalDAG-GEFs or cAMP-GEFs. In considering the various therapies described below, it is understood that such therapies may be targeted at tissue other than the brain where CalDAG-GEF or cAMP-GEF are also expressed.

Therapies to treat CalDAG-GEF and/or cAMP-GEF-associated diseases may be based upon (1) administration of normal CalDAG-GEF or cAMP-GEF proteins, (2) gene therapy with normal CalDAG-GEF or cAMP-GEF genes to compensate for or replace the mutant genes, (3) gene therapy based upon antisense sequences to mutant CalDAG-GEF or cAMP-GEF genes or which "knock-out" the mutant genes, (4) gene therapy based upon sequences which encode a protein which blocks or corrects the deleterious effects of CalDAG-GEF or cAMP-GEF mutants, (5) immunotherapy based upon antibodies to normal and/or mutant CalDAG-GEF or cAMP-GEF proteins, or (6) small molecules (drugs) which alter CalDAG-GEF or cAMP-GEF expression, block abnormal interactions between mutant forms of CalDAG-GEF or cAMP-GEF and other proteins or ligands, or which otherwise block the aberrant function of mutant CalDAG-GEF or cAMP-GEF proteins by altering the structure of the mutant proteins, by enhancing their metabolic clearance, or by inhibiting their function.

A. Protein Therapy

Treatment of CalDAG-GEF and/or cAMP-GEF-associated disorders, or disorders resulting from CalDAG-GEF and/or cAMP-GEF mutations, may be performed by providing an excess of inactive mutant protein to decrease the effect of the normal function of the protein, or by providing an excess of normal protein to reduce the effect of any aberrant function of the mutant protein, by replacing a mutant protein with normal protein, or by modulating the function of the mutant protein.

B. Gene Therapy

In one series of embodiments, gene therapy may be employed in which normal or mutant copies of the CalDAG-GEF gene or the cAMP-GEF gene are introduced into patients to code successfully for normal or mutant protein in one or more different affected cell types. The gene must be delivered to those cells in a form in which it can be taken up and code for sufficient protein to provide effective function. Thus, it is preferred that the recombinant gene be operably joined to a strong promoter so as to provide a high level of expression which will compensate for, or out-compete, the naturally-occurring proteins. As noted above, the recombinant construct may contain endogenous or exogenous regulatory elements, inducible or repressible regulatory elements, or tissue-specific regulatory elements.

In another series of embodiments, gene therapy may be employed to replace the naturally-occurring gene by homologous recombination with a recombinant construct. The recombinant construct may contain a normal or a mutant copy of the targeted CalDAG-GEF and/or cAMP-GEF gene, in which case the defect is corrected in situ, or may contain a "knock-out" construct which introduces a stop codon, missense mutation, or deletion which abolished function of the mutant gene. It should be noted in this respect that such a construct may knock-out both the normal and mutant copies of the targeted CalDAG-GEF and/or cAMP-GEF gene in a heterozygous individual, but the total loss of CalDAG-GEF and/or cAMP-GEF gene function may be less deleterious to the individual than continued progression of the disease state.

In another series of embodiments, antisense gene therapy may be employed. The antisense therapy is based on the fact that sequence-specific suppression of gene expression can be achieved by intracellular hybridization between mRNA or DNA and a complementary antisense species. The formation of a hybrid duplex may then interfere with the transcription of the gene and/or the processing, transport, translation and/or stability of the target CalDAG-GEF and/or cAMP-GEF mRNA. Antisense strategies may use a variety of approaches including the administration of antisense oligonucleotides or antisense oligonucleotide analogs (e.g., analogs with phosphorothioate backbones) or transfection with antisense RNA expression vectors. Again, such vectors may include exogenous or endogenous regulatory regions, inducible or repressible regulatory elements, or tissue-specific regulatory elements.

In another series of embodiments, gene therapy may be used to introduce a recombinant construct encoding a protein or peptide which blocks or otherwise corrects the aberrant function caused by a naturally-occurring CalDAG-GEF and/or cAMP-GEF gene. In one embodiment, the recombinant gene may encode a peptide which corresponds to a mutant domain of a CalDAG-GEF and/or cAMP-GEF which has been found to abnormally interact with another cell protein or other cell ligand. Alternatively, the portion of a protein which interacts with a mutant, but not a normal, CalDAG-GEF and/or cAMP-GEF may be encoded and expressed by a recombinant construct in order to compete with, and thereby inhibit or block, the aberrant interaction.

Retroviral vectors can be used for somatic cell gene therapy especially because of their high efficiency of infection and stable integration and expression. The targeted cells however must be able to divide and the expression of the levels of normal protein should be high. The full length CalDAG-GEF or cAMP-GEF genes, subsequences encoding functional domains of the CalDAG-GEFs or cAMP-GEFs, or any of the other therapeutic peptides described above, can be cloned into a retroviral vector and driven from its endogenous promoter, from the retroviral long terminal repeat, or from a promoter specific for the target cell type of interest. Other viral vectors which can be used include adeno-associated virus, vaccinia virus, bovine papilloma virus, or a herpes virus such as Epstein-Barr virus.

C. Immunotherapy

Antibodies may be raised to a mutant CalDAG-GEF or cAMP-GEF protein (or a portion thereof) and be administered to a patient to bind or block the mutant protein and prevent its deleterious effects. Alternatively, antibodies may be raised to specific complexes between mutant or wild-type CalDAG-GEF or cAMP-GEF and their interaction partners.

A further approach is to stimulate endogenous antibody production to the desired antigen. An immunogenic composition may be prepared as injectables, as liquid solutions or emulsions. The CalDAG-GEF or cAMP-GEF protein or other antigen may be mixed with pharmaceutically acceptable excipients compatible with the protein. Such excipients may include water, saline, dextrose, glycerol, ethanol and combinations thereof. The immunogenic composition and vaccine may further contain auxiliary substances such as emulsifying agents or adjuvants to enhance effectiveness. Immunogenic compositions and vaccines may be administered parenterally by injection subcutaneously or intramuscularly.

The immunogenic preparations and vaccines are administered in such amount as will be therapeutically effective, protective and immunogenic. Dosage depends on the route of administration and will vary according to the size of the host.

D. Small Molecule Therapeutics

As described and enabled herein, the present invention provides for a number of methods of identifying small molecules or other compounds which may be useful in the treatment of CalDAG-GEF- or cAMP-GEF-associated disorders. Thus, for example, the present invention provides for methods of identifying CalDAG-GEF or cAMP-GEF binding proteins and, in particular, methods for identifying proteins or other cell components which bind to or otherwise interact with mutant CalDAG-GEFs or cAMP-GEFs but not with the normal CalDAG-GEFs or cAMP-GEFs. The invention also provides for methods of identifying small molecules which can be used to disrupt undesired interactions between CalDAG-GEFs or cAMP-GEFs and other proteins or other cell components.

By identifying these proteins and analyzing these interactions, it is possible to screen for or design compounds which counteract or prevent the interaction, thereby, providing treatment for abnormal interactions. Therapies can be designed to modulate these interactions and thereby, to modulate CalDAG-GEF- or cAMP-GEF-associated disorders. The potential efficacy of these therapies can be tested by analyzing the affinity and function of these interactions after exposure to the therapeutic agent by standard pharmacokinetic measurements of affinity (e.g., Kd, Vmax) using synthetic peptides or recombinant proteins corresponding to functional domains of the CalDAG-GEF gene, the cAMP-GEF gene or other CalDAG-GEF and/or cAMP-GEF homologues. Another method for assaying the effect of any interactions involving functional domains is to monitor changes in the intracellular trafficking and post-translational modification of the relevant genes by in situ hybridization, immunohistochemistry, Western blotting and metabolic pulse-chase labeling studies in the presence of, and in the absence of, the therapeutic agents. A further method is to monitor the effects of "downstream" events including changes in second messenger events, e.g., cAMP, intracellular $Ca^{2+}$, protein kinase activities, etc.

The effect of potential therapeutic agents in cell lines and whole animals can be monitored by monitoring transcription, translation, and post-translational modification of the CalDAG-GEF and/or cAMP-GEF proteins. Methods for these studies include Western and Northern blots, immunoprecipitation after metabolic labelling (pulse-chase) with radio-labelled methionine and ATP, and immunohistochemistry. The effect of these agents can also be monitored using studies which examine the relative binding affinities and relative amounts of CalDAG-GEF or cAMP-GEF proteins involved in interactions with Rap1A, using either standard binding affinity assays or co-precipitation and Western blots using antibodies to Rap1A, CalDAG-GEF, cAMP-GEF, or other CalDAG-GEF and/or cAMP-GEF homologues.

Therapy using antisense oligonucleotides to block the expression of the mutant CalDAG-GEF gene or the mutant cAMP-GEF gene, co-ordinated with gene replacement with normal CalDAG-GEF or cAMP-GEF gene can also be applied using standard techniques of either gene therapy or protein replacement therapy.

V. EXAMPLES

Example 1

Isolation and characterization of CalDAG-GEF

Human full-length CalDAG-GEFI cDNAs were isolated from a human frontal cortex λZAPII cDNA library (Stratagene) and a U937 λZAPII cDNA library. Mouse full-length CalDAG-GEFI was identified in the mouse EST database (GenBank accession number: W71787). Rat full-length CalDAG-GEFII cDNA was isolated from a rat whole brain λZAPII cDNA library by using human CalDAG-GEFII as a probe. Mouse ESTs identified through BLAST searches were purchased from Genome Systems Inc. (St. Louis, Mo.).

CalDAG-GEFI encodes an approximately 69-kD protein (FIG. 2D) that displays in its amino terminal region a GEF domain that is highly homologous to Ras-superfamily GEFs (FIGS. 2A–2D). Multiple alignment analysis shows that genes of the CalDAG-GEF family form a cluster within the Ras-GEF superfamily distinct from Ras GEFs such as Sos1 and rRas-GEF (FIG. 2B). The region downstream of the GEF domain contains two tandem repeats of EF-hand $Ca^{2+}$ binding motifs (FIGS. 2A, 2E). The carboxy-terminal region displays a typical diacylglycerol/phorbol ester-binding domain, which is present in most PKC family proteins (FIG. 2A, 2F). Multiple sequence alignments and phylogenetic tree analysis were carried out with the LASERGENE Software Package (DNASTAR Inc.). Abbreviations and GenBank accession numbers of the protein sequences used in FIG. 2 are as follows: C3G: 474982, mCdc25: 882120, rRas-GRF: 57665, hSos1(human son-of-sevenless 1): 476780, BUD5: 171141, hCalmodulin: 115512, hCalbindin D28k: 227666, hCalcineurin B: 105504, hParvalbumin a: 131100, hTroponin C: 136043, hPKCa: 125549, hPKCb1: 125538, hPKCg: 462455.

To determine the small G protein target of CalDAG-GEFI, guanine nucleotide exchange activity in vivo was analyzed using intact 293T cells cotransfected with a eukaryotic expression construct of mouse CalDAG-GEFI and GST-tagged Ras family proteins. Full-length mouse CalDAG-GEFI cDNA inserted into a pCMV-SPORT expression vector with a carboxy-terminal FLAG epitope was used for transfection. A PCR-amplified fragment of rat CalDAG-GEFII was subcloned into a pCAGGS expression vector with the addition of $His_6$-tag at its amino-terminus, resulting in pCAGGS-His-CalDAGII. pEBG-Krev1 that expresses Rap1A was used as a fusion protein to glutathione S-transferase (GST) in mammalian cells, as described in Gotoh et al., 15 Mol. Cell Biol. 6746–53 (1995), pEBG-R-Ras, other vectors for Ras-family proteins obtained by inserting PCR-amplified cDNAs into pEBG expression vector, pCAGGS-C3G and pCAGGS-MSos 1, and pCEV-H-RasVl2. CalDAG-GEFI transfection produced a dramatic increase in GTP-bound Rap1A compared to the control but showed no or minimal activation of H-Ras, R-Ras, or Ral A. The increase in GTP-bound Rap1A was augmented in the presence of either the $Ca^{2+}$ ionophore, A23187, or the phorbol ester, phorbol-12-myristate-13-acetate (TPA). Further, A23187 and TPA had additive effects when administered together.

To determine the effect of CalDAG-GEFI on the Erk/MAP kinase cascade, Elk1 activation was measured in 293T cells transfected with CalDAG-GEFI or constitutively active H-Ras (RasV12), or both. 293T cells were transfected by SuperFect (Qiagen) as described in Gotoh, supra, with expression vectors for GST-tagged Ras family proteins and with those for various GEFs. Cells were labeled 24 hours after transfection with $^{32}P_i$ for 2 hr. In some experiments, cells were stimulated with either 10 μM A23187 or 1 μM phorbol-12-myristate-13-acetate (TPA) for 3 min. GST-tagged Ras family proteins were collected from cell lysates with glutathione Sepharose. Guanine nucleotides bound to Ras family proteins were separated by thin layer chromatography (TLC). Activation of Elk1 was examined by the PathDetect Elk1 transreporting system (Stratagene). 293T cells were transfected with pFR-Luc and pFA-Elk1 with various expression vectors, and light output was detected and analyzed by the use of LAS1000 film. CalDAG-GEFI reduced RasV12 activation of Elk1 by approximately 4-fold and did not itself activate Elk1. Thus, CalDAG-GEFI strongly inhibits Ras-dependent stimulation of the Erk/MAP kinase cascade.

Northern analysis showed that human CalDAG-GEFI is expressed strongly in the brain and that CalDAG-GEFI mRNA is strikingly enriched in the striatum. Probes used included human CalDAG-GEFI: 729-bp EcoRI fragment, human CalDAG-GEFII: 584-bp SacI and HindIII fragment, rat CalDAG-GEFI: 439-bp fragment of EST clone RBC565 (GenBank accession number: CO6861, and rat CalDAG-GEFII: 508-bp PCR amplified and subcloned fragment (nucleic acids 2541 to 3048 of SEQ ID NO:5). In situ hybridization of sections from the adult rat brain confirmed these restricted distribution patterns. Intense signal was present in the striatum (caudoputamen) and the ventral striatum (nucleus accumbens, olfactory tubercle). There was weaker signal in the olfactory bulb.

A series of monoclonal antibodies against the carboxy-terminal half of mouse CalDAG-GEFI were raised. $His_6$-tagged mouse CalDAG-GEFI polypeptide (amino acids 349 to 608 of SEQ ID NO: 1) was expressed in bacteria, purified over $Ni^{2+}$-nitrilotriacetic acid-agarose resin, and then used to immunize BALB/c mice. The resultant polyclonal antiserum was monitored by ELISA, Western blot, immunoprecipitation, and immunofluorescence assays on CalDAG-GEFI-transfected COS-7 cells. Hybridomas were generated by PEG (polyethylene glycol)-mediated fusion of donor splenocytes to the SP2/O cell line. Positive hybridoma cell lines were identified by screening in the assays described above, and purified by limiting dilution and single-cell cloning. Three hybridoma cell lines against mouse CalDAG-GEFI (mAbs 18B 11, 2D9, and 18A7), in addition to the polyclonal fusion serum, were identified. Western analysis showed that mAbs 18B11 and 2D9 were specific for CalDAG-GEFI. Lightly post-fixed, cryostat-cut 10 μm thick sections were immunostained by the ABC (Vectastain kit) method for CalDAG-GEFI with mAbs 18B11 and 2D9 and the polyclonal fusion serum, for tyrosine hydroxylase (TH) with monoclonal antibodies from INCSTAR, and for μ opioid receptor with polyclonal antiserum. Immunohistochemistry with mAb 18B11 showed a striking basal ganglia-enriched distribution pattern in sections of adult rat brain, with significant but weaker activity elsewhere. CalDAG-GEFI immunoreactivity marked the entire pathway from the striatal matrix compartment to the pallidum and substantia nigra pars reticulata, where very intense CalDAG-GEFI staining was present. Thus, CalDAG-GEFI is synthesized in striatal projection neurons and is transported to striatopallidal and striatonigral terminals.

To confirm that CalDAG-GEFI is synthesized in striatal projection neurons and transported to striatopallidal and striatonigral terminals in rats, intrastriatal injections of ibotenic acid (20 μg/μl, 1.5 μl per site, 5 day survival) were made unilaterally at 2 sites in the mid-lateral caudoputamen, with contralateral vehicle control injections were made. In other rats, unilateral subthalamic knife-cuts were made at an anteroposterior level between the entopeduncular nucleus and substantia nigra to sever the striatonigral efferents (1 and 3 days survivals), with control contralateral thalamic knife-cuts. These procedures all reduced CalDAG-GEFI staining in the substantia nigra. In situ hybridization was performed according to Simmons et al, 12 J. Histotechnol. 169–181 (1989). A 439 bp rat EST clone RBC565 (98.4% identical to mouse CalDAG-GEFI nucleic acids 1777 to 2216 of SEQ ID NO:1) was isolated by BLAST search and used for making RNA probes with $^{32}$P-labeled UTP (2,000 Ci/mmol, NEN, 1 Ci=37 GBq) and T3 and T7 RNA polymerase. Brains were processed as above for CalDAG-GEFI and TH immunostaining. Thus, CalDAG-GEFI is a protein transported in striatal axons to their terminals. The terminal localization of CalDAG-GEFI was confirmed in subcellular fractionation experiments on dissected samples from the rat ventral midbrain, in which Western analysis showed the presence of CalDAG-GEFI in cytosol and in membrane fractions, including synaptosomes.

Because of the similarity of the GEF domains of CalDAG-GEFI and CalDAG-GEFII, the substrate specificity of CalDAG-GEFII with the same 293T cell assay system used for CalDAG-GEFI was examined. It was confirmed that CalDAG-GEFII activates Ras, and further shown that it activates H-Ras and R-Ras, but not Ral A or Rap1A. H-Ras activation was enhanced by A23187 and TPA. Moreover, CalDAG-GEFII, unlike CalDAG-GEFI, increased the transcriptional activity of Elk1 downstream to Erk/MAP kinase. Thus, in the 293T system, CalDAG-GEFI and CalDAG-GEFII target different Ras-superfamily small G proteins and have opposite effects on the MAP kinase cascade. Northern analysis further showed contrasting brain expression for CalDAG-GEFII, with highest expression being in the cerebellum, cerebral cortex, and amygdala, and low expression occurring in the striatum. Both genes are also expressed in hematopoietic organs in both human and rat.

Rap signaling is important in regulating basal ganglia output in response to $Ca^{2+}$ and DAG. Corticostriatal inputs can activate the MAP kinase cascade in striatal projection neurons (Sgambat et al., 18 J. Neurosci. 214–26 (1993)) and phosphoinositide (PI) signaling is strongly represented in these pathways (Fotuhi et al., 13 J. Neurosci. 3300–08 (1993)). Moreover, a number of receptor systems in the striatum and its striatonigral/striatopallidal pathways are linked to $Ca^{2+}$ and PI signaling, notably including NMDA and metabotropic glutamate receptors, $D_2$-class dopamine receptors, and tachykinin receptors (Fiorillo et al., 394 Nature 78–82 (1998)). A previously unrecognized signaling target for some of these systems is likely to be Rap1, via CalDAG-GEFI. In addition, CalDAG-GEFI has a synaptic function as demonstrated by the heavy accumulation of CalDAG-GEFI in the target nuclei of striatal outputs and the localization of Rap1 in synaptosomes and synaptic vesicles. The particular basal ganglia projection systems are enriched in CalDAG-GEFI and are differentially vulnerable to neurodegeneration in Huntington's disease.

Rap and Ras functions can be regulated coordinately or disjunctively by $Ca^{2+}$ and DAG in the brain and hematopoietic organs, depending on the relative expression of CalDAG-GEFI and CalDAG-GEFII. In neurons, Ras/MAP kinase signaling has been directly implicated in synaptic transmission and the neuroplasticity underlying learning and memory. Different CalDAG-GEFI and CalDAG-GEFII expression patterns in the brain influence region-specific neuroplasticity mediated by $Ca^{2+}$ and DAG signaling pathways. The presence of CalDAG-GEFI and CalDAG-GEFII in the hematopoietic system demonstrates the direct input of $Ca^{2+}$ and DAG to Ras/Rap regulation of normal growth and differentiation as well as malignant transformation.

Example 2

Isolation and characterization of cAMP-GEFs cAMP-GEFI and cAMP-GEFII have similar domain structures, with a cAMP binding domain at the amino terminus and a GEF domain at the carboxy terminus separated by a link region (LR) (FIG. 3A). These mammalian proteins show strong structural homology to a predicted open reading frame (T20G5.5) in C. elegans cAMP-GEF (cel cAMP-GEF) (FIG. 3A). The cAMP binding domains of the cAMP-GEF family proteins form a distinct group within the cyclic nucleotide-binding protein superfamily and show the closest similarity to the B domains of PKA regulatory subunits (FIG. 3B). A PR(A/T)AT motif in the cAMP binding pocket is also conserved in the cAMP-GEF proteins (FIG. 3E). The first alanine of this motif confers cAMP (alanine) as opposed to cGMP (threonine) binding specificity. All of the cAMP-GEF family members have alanine at this position, and therefore bind cAMP rather then cGMP.

The GEF domains of the cAMP-GEFs show high homology to those of Ras-GEF family proteins, but form an independent cluster distinct from Ras GEFs such as mCdc25, hSos1, and rRas-GRF (FIG. 3, C and D). The three structurally conserved regions specific to Ras-GEF family proteins (SCR1, SCR2, and SCR3) are present in all of the cAMP-GEF proteins (FIG. 3D). Multiple sequence alignments and phylogenetic tree analyses were carried out with LASERGENE (DNASTAR Inc.). Abbreviations and GenBank accession numbers of the protein sequences used in this figure: hPKARIα (human cAMP-dependent protein kinase regulatory subunit type I-alpha): 125193, hPKARIβ: 1346362, hPKARIIα: 125198, hPKARIIβ: 400115, hPKGIα (human cGMP-dependent protein kinase type I-alpha): 1255602, HPKGIβ: 125379, hPKGII: 1906312, hCalDAG-GEFI: U71870, hCalDAG-GEFII: AF081195, C3G: 474982, hSos1(human son-of-sevenless 1): 476780, mCdc25: 882120, rRas-GRF: 57665, BUD5: 171141.

In order to identify the small G protein substrate for cAMP-GEFI and II and the mode of cAMP regulation of GEF activity conferred by these proteins, the effects of cAMP-GEFI and cAMP-GEFII expression were analyzed in 293T cells on the ratio of GTP to GDP bound to different Ras family small G proteins in the presence or absence of forskolin and IBMX. Under basal conditions, in the absence of forskolin and IBMX, only Rap1 was activated significantly. In the presence of forskolin and IBMX, both cAMP-GEFI and II strongly and selectively activated Rap1A, but did not activate H-Ras, R-Ras or Ra1A. The effects of forskolin/IBMX treatment on cAMP-GEFI and II were dose-dependent with $EC_{50}$ values of 1.8 $\mu$M and 0.3 $\mu$M, respectively. Forskolin/IBMX treatment given alone had no effect.

A time-course analysis of the activation of Rap1A by forskolin/IBMX in cAMP-GEFI transfectants showed that the activation began within 10 sec, reached a maximum at 5 min, and continued for at least 60 min. Thus, cAMP-GEFI has a direct effect on Rap1A rather than secondary effects mediated by other Ras-superfamily GEFs. In addition, Sp-cAMPS, an analogue of cAMP, activated Rap1A at levels similar to those induced by forskolin/IBMX. Thus, cAMP has the capacity to activate the GEF domain of cAMP-GEFI.

Mutational analyses with cAMP-GEFI was performed to examine whether its cAMP-binding domain is required for the activation of Rap1A. In contrast to wild type cAMP-GEFI, a deletion mutant lacking a cAMP binding domain (pcDNA-rcAMP-GEFI:DcAMP(528) and (595)) did not activate Rap1A with or without forskolin/IBMX treatment. Mutants with a single amino acid substitution at the cAMP binding pocket (pcDNA-rcAMP-GEFI:R(279)K) responded minimally to forskolin/IBMX treatment. Thus, the cAMP binding domain of cAMP-GEFI is necessary for its cAMP-dependent activation of Rap 1A.

To assess further the cAMP binding capacity of cAMP-GEFI, a cAMP agarose affinity bead binding assay was performed. In vitro translated, radiolabeled cAMP-GEFI showed selective binding to the beads that was competed by excess amounts of either cAMP or 8-Br-cAMP. cAMP-GEF protein can bind cAMP and that this binding can activate Rap1A.

cAMP-dependent activation of Rap1 has previously been ascribed to the phosphorylation of Rap1A by PKA, which raises its affinity to smgGDS, a GEF with broad substrate specificity. However, at least in the 293T cell assay system, an increase of GTP-bound Rap1A in response to increasing cAMP levels with forskolin or treatment with the cAMP analogue, Sp-cAMPS was not detected in the absence of cAMP-GEFs. In addition, even in the presence of H-89, a potent and selective inhibitor of PKA, cAMP-GEFI and II could still activate Rap1A. The activation of Rap1A induced by cAMP-GEFI and II is independent of the PKA pathway.

Intracellular cAMP has been shown to interact directly with ion channels, but the vast majority of cAMP-mediated effects in eukaryotes have been considered as sequels to cAMP binding by the regulatory subunits of the PKA tetramer. The diversity of physiological effects produced by cAMP have been attributed to the fact that, as a kinase, PKA has a large range of molecular targets. Reported herein are novel cAMP binding proteins that directly link the cAMP second messenger system to Ras superfamily signaling pathways and that appear selectively to target Rap.

cAMP can exert profound cell-type specific effects on cell growth and differentiation and that cAMP is capable of inhibiting or stimulating the Ras/mitogen-activated protein (MAP) kinase/Erk pathway. The inhibition can occur at the initial translocation step by which Ras activates Raf, whereas activation of Rap1 is thought to occur through phosphorylation by PKA. Activation of Rap1 has been suggested to be part of a switch mechanism determining whether growth or differentiation occurs in response to nerve growth factor (NGF). cAMP-GEFs directly couple cAMP to Rap1, itself discovered as a negative regulator of Ras but suspected of having independent functions as well. Thus, different levels of cAMP-GEF expression confer cell-type specific regulation of Ras superfamily signaling systems.

The genes also exhibit developmentally regulated expression in the septum, medial thalamus and habenula, key structures in the limbic system variously linked to brain reward circuits, addiction and schizophrenia. Thus, cAMP-GEFs, in addition to PKA, underlie some of the neuronal functions of cAMP.

Example 3

Northern Hybridization Demonstrating the Expression of CalDAG-GEFI and CalDAG-GEFII Protein mRNAs in a Variety of Tissues Total cytoplasmic RNA was isolated from various human tissue samples including amygdala, cerebellum, corpus callosum, caudate nucleus, cortex, frontal lobe, hippocampus, kidney, liver, lung, medulla obongata, occipital pole, putamen, spinal cord, substantia nigra, subthalamic nucleus, thalamus, and temporal lobe, obtained from surgical pathology using standard procedures such as CsCl purification. The RNA was then electrophoresed on a formaldehyde gel to permit size fractionation. The nitrocellulose membrane was prepared and the RNA was then transferred onto the membrane. $^{32}$P-labeled cDNA probes were prepared and added to the membrane in order for hybridization between the probe the RNA to occur. After washing, the membrane was wrapped in plastic film and placed into imaging cassettes containing X-ray film. The autoradiographs were then allowed to develop for one to several days. Sizing was established by comparison to standard RNA markers. These northern blots demonstrated that the CalDAG-GEF genes are strongly expressed in the brain. Weaker hybridization was detectable elsewhere.

Example 4

Northern Hybridization Demonstrating the Expression of cAMP-GEFI and cAMP-GEFII Protein mRNAs in a Variety of Tissues Northern hybridization analysis was performed as in Example 3 to detect the expression of the cAMP-GEFI and cAMP-GEFII genes in a variety of human tissues. The tissues analyzed included adrenal gland, amygdala, bone marrow, cerebellum, corpus callosum, caudate nucleus, colon (mucosal lining), caudputamen, cortex, frontal lobe, hippocampus, habenula, heart, kidney, liver, lung, lymph node, medulla obongata, occipital pole, olfactory bulb, ovary, pons, pancreas, putamen, septum, small intestines, skeletal muscle, spinal cord, spleen, stomach, substantia nigra, subthalamic nucleus, testis, thalamus, temporal lobe, thymus, trachea, and thyroid.

A striking contrast in the expression patterns of human cAMP-GEFI and II was observed by Northern analysis. Human cAMP-GEFI is widely expressed, with highest levels appearing in kidney, spleen, thyroid, heart, and pancreas. Human cAMP-GEFII shows a remarkably selective enrichment in the brain and the adrenal glands. Both genes were developmentally regulated. The expression patterns of the two genes in the nervous system also differ, with cAMP-GEFI having a wider expression than cAMP-GEFII. These region-specific neuronal expression patterns were confirmed in in situ hybridization experiments. cAMP-GEFI mRNA is expressed broadly at low levels in the adult brain, but it is strongly and selectively expressed in parts of the neonatal brain, including the septum and the thalamus. By contrast, cAMP-GEFII is strongly expressed in the mature as well as the developing brain. Notable are the high levels of cAMP-GEFII mRNA in the cerebral cortex, the hippocampus (especially CA3 and dentate gyrus), the habenula and the cerebellum. Genes of the cAMP-GEF family have widespread influence on cAMP functions in bodily organs and also region-specific functions in the brain.

Example 5

Isolation of CalDAG-GEF or cAMP-GEF Binding Proteins by Yeast Two-Hybrid System

To identify proteins interacting with the CalDAG-GEF or cAMP-GEF proteins, a yeast expression plasmid vector (pAS2-1, Clontech) is generated by ligating an in-frame partial cDNA sequence encoding either residues of the CalDAG-GEF protein or residues of the cAMP-GEF protein into the EcoRI and BamHI sites of the vector. The resultant fusion protein contains the GAL4 DNA binding domain coupled in-frame either to residues of the CalDAG-GEF protein or to residues of the cAMP-GEF protein. These expression plasmids are co-transformed, along with purified plasmid DNA from the human brain cDNA:pACT library, into yeast using the protocols of the Clontech Matchmaker yeast-two-hybrid kit (Clontech). Yeast clones bearing human brain cDNAs which interact with the CalDAG-GEF or cAMP-GEF fragments are selected by HIS resistance and βgal+activation. The clones are further selected by cyclohexamide sensitivity and the inserts of the human brain cDNAs are isolated by PCR and sequenced.

Although preferred embodiments of the invention have been described herein in detail, it will be understood by those skilled in the art that variations may be made thereto without departing from the spirit of the invention or the scope of the following claims.

SEQUENCE LISTING

```
<160> NUMBER OF SEQ ID NOS: 67

<210> SEQ ID NO 1
<211> LENGTH: 2250
<212> TYPE: DNA
<213> ORGANISM: Mus musculus
<220> FEATURE:
<221> NAME/KEY: CDS
<222> LOCATION: (166)..(1989)

<400> SEQUENCE: 1
cgaaggatca gaggctgagc tggttcaagt gaacagaagg tctgggaggt gaactgcatt      60
cgggtttgca ttctgaagta aaggacttgg gacaggggta cgaatcgagc actgtgggag     120
gctctgagag tgtaacttgg gtctagccca ctggcaccgg cagcc atg gcg agc act     177
                                                 Met Ala Ser Thr
                                                   1 ctg gac ctg gac aag ggt tgc acc gtg gag gag ctg ctc cgt ggc tgt      225
Leu Asp Leu Asp Lys Gly Cys Thr Val Glu Glu Leu Leu Arg Gly Cys
 5              10                  15                  20 atc gaa gcc ttt gat gac tct gga aag gtg cga gat cca cag cta gtg      273
Ile Glu Ala Phe Asp Asp Ser Gly Lys Val Arg Asp Pro Gln Leu Val
                25                  30                  35 cgc atg ttt ctc atg atg cac ccc tgg tac ata cct tcc tct cag ctg      321
Arg Met Phe Leu Met Met His Pro Trp Tyr Ile Pro Ser Ser Gln Leu
            40                  45                  50 gct tcg aaa ctg ctc cac ttc tat cag caa tcc cgg aag gac aac tcc      369
Ala Ser Lys Leu Leu His Phe Tyr Gln Gln Ser Arg Lys Asp Asn Ser
        55                  60                  65 aat tcc cta cag gtg aaa acc tgt cac ctg gtc agg tac tgg gtc tca      417
Asn Ser Leu Gln Val Lys Thr Cys His Leu Val Arg Tyr Trp Val Ser
    70                  75                  80
```

```
                                                                    -continued gcc ttc cca gca gag ttc gac ttg aac cca gag ctg gct gaa ccg atc    465
Ala Phe Pro Ala Glu Phe Asp Leu Asn Pro Glu Leu Ala Glu Pro Ile
85              90                  95                  100 aag gag ctg aag gct ctg tta gac caa gaa gga aac cgc agg cac agc    513
Lys Glu Leu Lys Ala Leu Leu Asp Gln Glu Gly Asn Arg Arg His Ser
            105                 110                 115 agc ctc atc gac atc gag agt gtc ccc acc tac aag tgg aag cgg cag    561
Ser Leu Ile Asp Ile Glu Ser Val Pro Thr Tyr Lys Trp Lys Arg Gln
        120                 125                 130 gtg acc cag cgg aac cct gtg gaa cag aaa aag cgc aag atg tcc ctg    609
Val Thr Gln Arg Asn Pro Val Glu Gln Lys Lys Arg Lys Met Ser Leu
    135                 140                 145 ttg ttt gat cac ttg gag cct atg gaa ctg gca gaa cat ctc acc tac    657
Leu Phe Asp His Leu Glu Pro Met Glu Leu Ala Glu His Leu Thr Tyr
150                 155                 160 ttg gag tat cgg tcc ttc tgc aag atc ctg ttc cag gac tat cac agc    705
Leu Glu Tyr Arg Ser Phe Cys Lys Ile Leu Phe Gln Asp Tyr His Ser
165             170                 175                 180 ttt gtg act cat ggc tgc act gta gac aat ccg gtc ctg gag cga ttc    753
Phe Val Thr His Gly Cys Thr Val Asp Asn Pro Val Leu Glu Arg Phe
                185                 190                 195 atc tcc ctc ttc aac agt gtc tct cag tgg gtc caa ctc atg atc ctc    801
Ile Ser Leu Phe Asn Ser Val Ser Gln Trp Val Gln Leu Met Ile Leu
            200                 205                 210 agc aag ccc aca gcc acg cag cgg gcg ctg gtc atc aca cat ttc gtg    849
Ser Lys Pro Thr Ala Thr Gln Arg Ala Leu Val Ile Thr His Phe Val
        215                 220                 225 cat gtg gca gag aag ctg ctg cag ctg cag aac ttc aac acg ttg atg    897
His Val Ala Glu Lys Leu Leu Gln Leu Gln Asn Phe Asn Thr Leu Met
    230                 235                 240 gcc gtc gtg gga ggc ctg agc cac agc tcc atc tca cgc ctc aag gag    945
Ala Val Val Gly Gly Leu Ser His Ser Ser Ile Ser Arg Leu Lys Glu
245                 250                 255                 260 acc cac agc cat gtc agc cct gac acc atc aag ctc tgg gaa ggt ctg    993
Thr His Ser His Val Ser Pro Asp Thr Ile Lys Leu Trp Glu Gly Leu
                265                 270                 275 aca gaa cta gtg aca gct act ggc aac tac agc aac tac cgg cga agg    1041
Thr Glu Leu Val Thr Ala Thr Gly Asn Tyr Ser Asn Tyr Arg Arg Arg
            280                 285                 290 ctg gcg gcc tgc gtg ggc ttc cgc ttt cct atc ctg ggt gtg cac ctc    1089
Leu Ala Ala Cys Val Gly Phe Arg Phe Pro Ile Leu Gly Val His Leu
        295                 300                 305 aag gat cta gtg gct ctg cag ctg gct ctg cct gac tgg ctg gac cca    1137
Lys Asp Leu Val Ala Leu Gln Leu Ala Leu Pro Asp Trp Leu Asp Pro
310                 315                 320 ggt cgg acc cgg ctc aat gga gcc aag atg agg cag ctt ttc agc att    1185
Gly Arg Thr Arg Leu Asn Gly Ala Lys Met Arg Gln Leu Phe Ser Ile
325                 330                 335                 340 ctg gag gag ttg gct atg gtg acc agt ctt cga cca cca gtg caa gcc    1233
Leu Glu Glu Leu Ala Met Val Thr Ser Leu Arg Pro Pro Val Gln Ala
                345                 350                 355 aac ccc gac ctg ctg agt ctg ctc acg gtg tcc ctg gac cag tat cag    1281
Asn Pro Asp Leu Leu Ser Leu Leu Thr Val Ser Leu Asp Gln Tyr Gln
            360                 365                 370 acg gag gat gag ctg tat cag ctc tct ctg cag cga gag cca cgt tcc    1329
Thr Glu Asp Glu Leu Tyr Gln Leu Ser Leu Gln Arg Glu Pro Arg Ser
        375                 380                 385 aag tca tcg ccc acc agc ccc acc agc tgc acc ccg cct ccc cgg ccg    1377
Lys Ser Ser Pro Thr Ser Pro Thr Ser Cys Thr Pro Pro Pro Arg Pro
390                 395                 400
```

-continued

| | | |
|---|---|---|
| cct gtg ctg gaa gag tgg acc tca gtt gcc aag cct aag ctg gac caa<br>Pro Val Leu Glu Glu Trp Thr Ser Val Ala Lys Pro Lys Leu Asp Gln<br>405                      410                      415                      420 | 1425 |
| gcc ttg gtg gcc gag cac att gag aag atg gtg gag tct gtg ttc cgg<br>Ala Leu Val Ala Glu His Ile Glu Lys Met Val Glu Ser Val Phe Arg<br>                      425                      430                      435 | 1473 |
| aac ttt gac gtt gat ggg gac ggt cac atc tcc cag gag gag ttc cag<br>Asn Phe Asp Val Asp Gly Asp Gly His Ile Ser Gln Glu Glu Phe Gln<br>440                      445                      450 | 1521 |
| atc atc cgg ggc aac ttc cct tat ctc agc gcc ttt ggg gac ttg gac<br>Ile Ile Arg Gly Asn Phe Pro Tyr Leu Ser Ala Phe Gly Asp Leu Asp<br>              455                      460                      465 | 1569 |
| cag aac cag gat ggc tgc atc agc cgg gag gag atg att tcc tac ttc<br>Gln Asn Gln Asp Gly Cys Ile Ser Arg Glu Glu Met Ile Ser Tyr Phe<br>470                      475                      480 | 1617 |
| ctg cgc tcc agc tcc gtg ctg gga ggc cgc atg ggc ttc gta cac aac<br>Leu Arg Ser Ser Ser Val Leu Gly Gly Arg Met Gly Phe Val His Asn<br>485                      490                      495                      500 | 1665 |
| ttc cag gag agt aac tcg cta agg ccg gtc gcc tgc cga cac tgc aaa<br>Phe Gln Glu Ser Asn Ser Leu Arg Pro Val Ala Cys Arg His Cys Lys<br>                      505                      510                      515 | 1713 |
| gct ctg atc ctg ggc atc tac aag cag ggc ctc aaa tgt aga gct tgt<br>Ala Leu Ile Leu Gly Ile Tyr Lys Gln Gly Leu Lys Cys Arg Ala Cys<br>520                      525                      530 | 1761 |
| ggt gtg aac tgc cac aag cag tgc aaa gac cga ctg tca gtg gaa tgt<br>Gly Val Asn Cys His Lys Gln Cys Lys Asp Arg Leu Ser Val Glu Cys<br>                      535                      540                      545 | 1809 |
| cgc cgc cgc gcc cag agt gtg agc ctg gag ggc tct gca ccc tct ccc<br>Arg Arg Arg Ala Gln Ser Val Ser Leu Glu Gly Ser Ala Pro Ser Pro<br>550                      555                      560 | 1857 |
| tca ccc aca cat acc cac cat cgg gcc ttc agc ttc tcc ctg cct cgc<br>Ser Pro Thr His Thr His His Arg Ala Phe Ser Phe Ser Leu Pro Arg<br>565                      570                      575                      580 | 1905 |
| cca ggc agg cgc agc tct cgg cct cca gag atc cgt gaa gag gag gtg<br>Pro Gly Arg Arg Ser Ser Arg Pro Pro Glu Ile Arg Glu Glu Glu Val<br>                      585                      590                      595 | 1953 |
| cag act gtg gaa gat ggt gtg ttc gac atc cac tta taagacgctg<br>Gln Thr Val Glu Asp Gly Val Phe Asp Ile His Leu<br>600                      605 | 1999 |
| tgactatcaa ggactcattc ctgccttgga gaaaagactt ggagcagagc agggagccag | 2059 |
| ggattctggg gcaggaggtt ggggctgaag gtgggggaag ttgaaggtgg catgcactga | 2119 |
| aaaaaaggcc agggctggtg tccctaaggt tgtacagact tctgtgaata tttgtatttt | 2179 |
| ccagatggaa taaaaggcc cgaataatta acctcgaaaa aaaaaaaaaa aaaaaaaaaa | 2239 |
| aaaaaaaaaa a | 2250 |

<210> SEQ ID NO 2
<211> LENGTH: 608
<212> TYPE: PRT
<213> ORGANISM: Mus musculus

<400> SEQUENCE: 2

Met Ala Ser Thr Leu Asp Leu Asp Lys Gly Cys Thr Val Glu Glu Leu
1                 5                    10                 15

Leu Arg Gly Cys Ile Glu Ala Phe Asp Asp Ser Gly Lys Val Arg Asp
                  20                    25                    30

Pro Gln Leu Val Arg Met Phe Leu Met Met His Pro Trp Tyr Ile Pro
              35                    40                    45

-continued

```
Ser Ser Gln Leu Ala Ser Lys Leu Leu His Phe Tyr Gln Gln Ser Arg
    50                  55                  60
Lys Asp Asn Ser Asn Ser Leu Gln Val Lys Thr Cys His Leu Val Arg
 65                  70                  75                  80
Tyr Trp Val Ser Ala Phe Pro Ala Glu Phe Asp Leu Asn Pro Glu Leu
                 85                  90                  95
Ala Glu Pro Ile Lys Glu Leu Lys Ala Leu Leu Asp Gln Glu Gly Asn
            100                 105                 110
Arg Arg His Ser Ser Leu Ile Asp Ile Glu Ser Val Pro Thr Tyr Lys
            115                 120                 125
Trp Lys Arg Gln Val Thr Gln Arg Asn Pro Val Glu Gln Lys Lys Arg
130                 135                 140
Lys Met Ser Leu Leu Phe Asp His Leu Glu Pro Met Glu Leu Ala Glu
145                 150                 155                 160
His Leu Thr Tyr Leu Glu Tyr Arg Ser Phe Cys Lys Ile Leu Phe Gln
                165                 170                 175
Asp Tyr His Ser Phe Val Thr His Gly Cys Thr Val Asp Asn Pro Val
            180                 185                 190
Leu Glu Arg Phe Ile Ser Leu Phe Asn Ser Val Ser Gln Trp Val Gln
            195                 200                 205
Leu Met Ile Leu Ser Lys Pro Thr Ala Thr Gln Arg Ala Leu Val Ile
210                 215                 220
Thr His Phe Val His Val Ala Glu Lys Leu Leu Gln Leu Gln Asn Phe
225                 230                 235                 240
Asn Thr Leu Met Ala Val Val Gly Gly Leu Ser His Ser Ser Ile Ser
                245                 250                 255
Arg Leu Lys Glu Thr His Ser His Val Ser Pro Asp Thr Ile Lys Leu
            260                 265                 270
Trp Glu Gly Leu Thr Glu Leu Val Thr Ala Thr Gly Asn Tyr Ser Asn
            275                 280                 285
Tyr Arg Arg Arg Leu Ala Ala Cys Val Gly Phe Arg Phe Pro Ile Leu
            290                 295                 300
Gly Val His Leu Lys Asp Leu Val Ala Leu Gln Leu Ala Leu Pro Asp
305                 310                 315                 320
Trp Leu Asp Pro Gly Arg Thr Arg Leu Asn Gly Ala Lys Met Arg Gln
                325                 330                 335
Leu Phe Ser Ile Leu Glu Glu Leu Ala Met Val Thr Ser Leu Arg Pro
            340                 345                 350
Pro Val Gln Ala Asn Pro Asp Leu Leu Ser Leu Leu Thr Val Ser Leu
            355                 360                 365
Asp Gln Tyr Gln Thr Glu Asp Glu Leu Tyr Gln Leu Ser Leu Gln Arg
    370                 375                 380
Glu Pro Arg Ser Lys Ser Ser Pro Thr Ser Pro Thr Ser Cys Thr Pro
385                 390                 395                 400
Pro Pro Arg Pro Pro Val Leu Glu Glu Trp Thr Ser Val Ala Lys Pro
                405                 410                 415
Lys Leu Asp Gln Ala Leu Val Ala Glu His Ile Glu Lys Met Val Glu
            420                 425                 430
Ser Val Phe Arg Asn Phe Asp Val Asp Gly Asp Gly His Ile Ser Gln
            435                 440                 445
Glu Glu Phe Gln Ile Ile Arg Gly Asn Phe Pro Tyr Leu Ser Ala Phe
    450                 455                 460
```

| | | | | | | | | | | | | |
|---|---|---|---|---|---|---|---|---|---|---|---|---|
|Gly|Asp|Leu|Asp|Gln|Asn|Gln|Asp|Gly|Cys|Ile|Ser|Arg|Glu|Glu|Met|
|465| | | |470| | | |475| | | |480|

| | | | | | | | | | | | |
|---|---|---|---|---|---|---|---|---|---|---|---|
|Ile|Ser|Tyr|Phe|Leu|Arg|Ser|Ser|Val|Leu|Gly|Gly|Arg|Met|Gly|
| | | | |485| | | |490| | | |495|

| | | | | | | | | | | | |
|---|---|---|---|---|---|---|---|---|---|---|---|
|Phe|Val|His|Asn|Phe|Gln|Glu|Ser|Asn|Ser|Leu|Arg|Pro|Val|Ala|Cys|
| | | |500| | | |505| | | |510|

| | | | | | | | | | | | |
|---|---|---|---|---|---|---|---|---|---|---|---|
|Arg|His|Cys|Lys|Ala|Leu|Ile|Leu|Gly|Ile|Tyr|Lys|Gln|Gly|Leu|Lys|
| | |515| | | |520| | | |525|

| | | | | | | | | | | | |
|---|---|---|---|---|---|---|---|---|---|---|---|
|Cys|Arg|Ala|Cys|Gly|Val|Asn|Cys|His|Lys|Gln|Cys|Lys|Asp|Arg|Leu|
| |530| | | |535| | | |540|

| | | | | | | | | | | | |
|---|---|---|---|---|---|---|---|---|---|---|---|
|Ser|Val|Glu|Cys|Arg|Arg|Arg|Ala|Gln|Ser|Val|Ser|Leu|Glu|Gly|Ser|
|545| | | |550| | | |555| | | |560|

| | | | | | | | | | | | |
|---|---|---|---|---|---|---|---|---|---|---|---|
|Ala|Pro|Ser|Pro|Ser|Pro|Thr|His|Thr|His|His|Arg|Ala|Phe|Ser|Phe|
| | | |565| | | |570| | | |575|

| | | | | | | | | | | | |
|---|---|---|---|---|---|---|---|---|---|---|---|
|Ser|Leu|Pro|Arg|Pro|Gly|Arg|Arg|Ser|Ser|Arg|Pro|Pro|Glu|Ile|Arg|
| | |580| | | |585| | | |590|

| | | | | | | | | | | | |
|---|---|---|---|---|---|---|---|---|---|---|---|
|Glu|Glu|Glu|Val|Gln|Thr|Val|Glu|Asp|Gly|Val|Phe|Asp|Ile|His|Leu|
| |595| | | |600| | | |605|

```
<210> SEQ ID NO 3
<211> LENGTH: 2236
<212> TYPE: DNA
<213> ORGANISM: Homo sapiens
<220> FEATURE:
<221> NAME/KEY: CDS
<222> LOCATION: (161)..(1987)

<400> SEQUENCE: 3
ggggactcaa ggctggcctg gctcaagtga acagcacgtc caggaggcga cctcgtccgc      60
gggtttgcat tctggggtgg acgagctggg ggttcggtcc gagcccggtg ggaggctccc     120
ggagcgcagc ctgggcccag cccaccccgc gccggcggcc atg gca ggc acc ctg      175
                                              Met Ala Gly Thr Leu
                                                1               5 gac ctg gac aag ggc tgc acg gtg gag gag ctg ctc cgc ggg tgc atc      223
Asp Leu Asp Lys Gly Cys Thr Val Glu Glu Leu Leu Arg Gly Cys Ile
             10                  15                  20 gaa gcc ttc gat gac tcc ggg aag gtg cgg gac ccg cag ctg gtg cgc      271
Glu Ala Phe Asp Asp Ser Gly Lys Val Arg Asp Pro Gln Leu Val Arg
         25                  30                  35 atg ttc ctc atg atg cac ccc tgg tac atc ccc tcc tct cag ctg gcg      319
Met Phe Leu Met Met His Pro Trp Tyr Ile Pro Ser Ser Gln Leu Ala
     40                  45                  50 gcc aag ctg ctc cac atc tac caa caa tcc cgg aag gac aac tcc aat      367
Ala Lys Leu Leu His Ile Tyr Gln Gln Ser Arg Lys Asp Asn Ser Asn
 55                  60                  65 tcc ctg cag gtg aaa acg tgc cac ctg gtc agg tac tgg atc tcc gcc      415
Ser Leu Gln Val Lys Thr Cys His Leu Val Arg Tyr Trp Ile Ser Ala
 70                  75                  80                  85 ttc cca gcg gag ttt gac ttg aac ccg gag ttg gct gag cag atc aag      463
Phe Pro Ala Glu Phe Asp Leu Asn Pro Glu Leu Ala Glu Gln Ile Lys
             90                  95                 100 gag ctg aag gct ctg cta gac caa gaa ggg aac cga cgg cac agc agc      511
Glu Leu Lys Ala Leu Leu Asp Gln Glu Gly Asn Arg Arg His Ser Ser
            105                 110                 115 cta atc gac ata gac agc gtc cct acc tac aag tgg aag cgg cag gtg      559
Leu Ile Asp Ile Asp Ser Val Pro Thr Tyr Lys Trp Lys Arg Gln Val
        120                 125                 130 act cag cgg aac cct gtg gga cag aaa aag cgc aag atg tcc ctg ttg      607
```

-continued

```
Thr Gln Arg Asn Pro Val Gly Gln Lys Lys Arg Lys Met Ser Leu Leu
    135                 140                 145 ttt gac cac ctg gag ccc atg gag ctg gcg gag cat ctc acc tac ttg        655
Phe Asp His Leu Glu Pro Met Glu Leu Ala Glu His Leu Thr Tyr Leu
150                 155                 160                 165 gag tat cgc tcc ttc tgc aag atc ctg ttt cag gac tat cac agt ttc        703
Glu Tyr Arg Ser Phe Cys Lys Ile Leu Phe Gln Asp Tyr His Ser Phe
                170                 175                 180 gtg act cat ggc tgc act gtg gac aac ccc gtc ctg gag cgg ttc atc        751
Val Thr His Gly Cys Thr Val Asp Asn Pro Val Leu Glu Arg Phe Ile
            185                 190                 195 tcc ctc ttc aac agc gtc tca cag tgg gtg cag ctg atg atc ctc agc        799
Ser Leu Phe Asn Ser Val Ser Gln Trp Val Gln Leu Met Ile Leu Ser
        200                 205                 210 aaa ccc aca gcc ccg cag cgg gcc ctg gtc atc aca cac ttt gtc cac        847
Lys Pro Thr Ala Pro Gln Arg Ala Leu Val Ile Thr His Phe Val His
    215                 220                 225 gtg gcg gag aag ctg cta cag ctg cag aac ttc aac acg ctg atg gca        895
Val Ala Glu Lys Leu Leu Gln Leu Gln Asn Phe Asn Thr Leu Met Ala
230                 235                 240                 245 gtc gtc ggg ggc ctg agc cac agc tcc atc tcc cgc ctc aag gag acc        943
Val Val Gly Gly Leu Ser His Ser Ser Ile Ser Arg Leu Lys Glu Thr
                250                 255                 260 cac agc cac gtt agc cct gag acc atc aag ctc tgg gag ggt ctc acg        991
His Ser His Val Ser Pro Glu Thr Ile Lys Leu Trp Glu Gly Leu Thr
            265                 270                 275 gaa cta gtg acg gcg aca ggc aac tat ggc aac tac cgg cgt cgg ctg       1039
Glu Leu Val Thr Ala Thr Gly Asn Tyr Gly Asn Tyr Arg Arg Arg Leu
        280                 285                 290 gca gcc tgt gtg ggc ttc cgc ttc ccg atc ctg ggt gtg cac ctc aag       1087
Ala Ala Cys Val Gly Phe Arg Phe Pro Ile Leu Gly Val His Leu Lys
    295                 300                 305 gac ctg gtg gcc ctg cag ctg gca ctg cct gac tgg ctg gac cca gcc       1135
Asp Leu Val Ala Leu Gln Leu Ala Leu Pro Asp Trp Leu Asp Pro Ala
310                 315                 320                 325 cgg acc cgg ctc aac ggg gcc aag atg aag cag ctc ttt agc atc ctg       1183
Arg Thr Arg Leu Asn Gly Ala Lys Met Lys Gln Leu Phe Ser Ile Leu
                330                 335                 340 gag gag ctg gcc atg gtg acc agc ctg cgg cca cca gta cag gcc aac       1231
Glu Glu Leu Ala Met Val Thr Ser Leu Arg Pro Pro Val Gln Ala Asn
            345                 350                 355 ccc gac ctg ctg agc ctg ctc acg gtg tct ctg gat cag tat cag acg       1279
Pro Asp Leu Leu Ser Leu Leu Thr Val Ser Leu Asp Gln Tyr Gln Thr
        360                 365                 370 gag gat gag ctg tac cag ctg tcc ctg cag cgg gag ccg cgc tcc aag       1327
Glu Asp Glu Leu Tyr Gln Leu Ser Leu Gln Arg Glu Pro Arg Ser Lys
    375                 380                 385 tct tcg cca acc agc ccc acg agt tgc acc cca cca ccc cgg ccc ccg       1375
Ser Ser Pro Thr Ser Pro Thr Ser Cys Thr Pro Pro Pro Arg Pro Pro
390                 395                 400                 405 gta ttg gag gag tgg acc tcg gct gcc aaa ccc aag ctg gat cag gcc       1423
Val Leu Glu Glu Trp Thr Ser Ala Ala Lys Pro Lys Leu Asp Gln Ala
                410                 415                 420 ctc gtg gtg gag cac atc gag aag atg gtg gag tct gtg ttc cgg aac       1471
Leu Val Val Glu His Ile Glu Lys Met Val Glu Ser Val Phe Arg Asn
            425                 430                 435 ttt gac gtc gat ggg gat ggc cac atc tca cag gaa gaa ttc cag atc       1519
Phe Asp Val Asp Gly Asp Gly His Ile Ser Gln Glu Glu Phe Gln Ile
        440                 445                 450
```

-continued

| | |
|---|---|
| atc cgt ggg aac ttc cct tac ctc agc gcc ttt ggg gac ctc gac cag<br>Ile Arg Gly Asn Phe Pro Tyr Leu Ser Ala Phe Gly Asp Leu Asp Gln<br>455                               460                        465 | 1567 |
| aac cag gat ggc tgc atc agc agg gag gag atg gtt tcc tat ttc ctg<br>Asn Gln Asp Gly Cys Ile Ser Arg Glu Glu Met Val Ser Tyr Phe Leu<br>470                               475                     480                     485 | 1615 |
| cgc tcc agc tct gtg ttg ggg ggc cgc atg ggc ttc gta cac aac ttc<br>Arg Ser Ser Ser Val Leu Gly Gly Arg Met Gly Phe Val His Asn Phe<br>                         490                             495                     500 | 1663 |
| cag gag agc aac tcc ttg cgc ccc gtc gcc tgc cgc cac tgc aaa gcc<br>Gln Glu Ser Asn Ser Leu Arg Pro Val Ala Cys Arg His Cys Lys Ala<br>                       505                     510                         515 | 1711 |
| ctg atc ctg ggc atc tac aag cag ggc ctc aaa tgc gga gcc tgt gga<br>Leu Ile Leu Gly Ile Tyr Lys Gln Gly Leu Lys Cys Arg Ala Cys Gly<br>                  520                       525                     530 | 1759 |
| gtg aac tgc cac aag cag tgc aag gat cgc ctg tca gtt gag tgt cgg<br>Val Asn Cys His Lys Gln Cys Lys Asp Arg Leu Ser Val Glu Cys Arg<br>535                             540                     545 | 1807 |
| cgc agg gcc cag agt gtg agc ctg gag ggg tct gca ccc tca ccc tca<br>Arg Arg Ala Gln Ser Val Ser Leu Glu Gly Ser Ala Pro Ser Pro Ser<br>550                             555                     560                 565 | 1855 |
| ccc atg cac agc cac cat cac cgc gcc ttc agc ttc tct ctg ccc cgc<br>Pro Met His Ser His His His Arg Ala Phe Ser Phe Ser Leu Pro Arg<br>                  570                       575                     580 | 1903 |
| cct ggc agg cga ggc tcc agg cct cca gag atc cgt gag gag gag gta<br>Pro Gly Arg Arg Gly Ser Arg Pro Pro Glu Ile Arg Glu Glu Glu Val<br>                       585                       590                        595 | 1951 |
| cag acg gtg gag gat ggg gtg ttt gac atc cac ttg taatagatgc<br>Gln Thr Val Glu Asp Gly Val Phe Asp Ile His Leu<br>                 600                       605 | 1997 |
| tgtggttgga tcaaggactc attcctgcct tggagaaaat acttcaacca gagcagggag | 2057 |
| cctgggggtg tcggggcagg aggctgggga tggggtggg atatgagggt ggcatgcagc | 2117 |
| tgagggcagg gccagggctg gtgtccctaa ggttgtacag actcttgtga atatttgtat | 2177 |
| tttccagatg gaataaaaag gcccgtgtaa ttaaccttca aaaaaaaaaa aaaaaaaa | 2236 |

<210> SEQ ID NO 4
<211> LENGTH: 609
<212> TYPE: PRT
<213> ORGANISM: Homo sapiens

<400> SEQUENCE: 4

Met Ala Gly Thr Leu Asp Leu Asp Lys Gly Cys Thr Val Glu Glu Leu
1               5                   10                  15

Leu Arg Gly Cys Ile Glu Ala Phe Asp Asp Ser Gly Lys Val Arg Asp
                20                  25                  30

Pro Gln Leu Val Arg Met Phe Leu Met Met His Pro Trp Tyr Ile Pro
            35                  40                  45

Ser Ser Gln Leu Ala Ala Lys Leu Leu His Ile Tyr Gln Gln Ser Arg
        50                  55                  60

Lys Asp Asn Ser Asn Ser Leu Gln Val Lys Thr Cys His Leu Val Arg
65                  70                  75                  80

Tyr Trp Ile Ser Ala Phe Pro Ala Glu Phe Asp Leu Asn Pro Glu Leu
                85                  90                  95

Ala Glu Gln Ile Lys Glu Leu Lys Ala Leu Leu Asp Gln Glu Gly Asn
            100                 105                 110

Arg Arg His Ser Ser Leu Ile Asp Ile Asp Ser Val Pro Thr Tyr Lys
        115                 120                 125

```
Trp Lys Arg Gln Val Thr Gln Arg Asn Pro Val Gly Gln Lys Lys Arg
130                 135                 140
Lys Met Ser Leu Leu Phe Asp His Leu Glu Pro Met Glu Leu Ala Glu
145                 150                 155                 160
His Leu Thr Tyr Leu Glu Tyr Arg Ser Phe Cys Lys Ile Leu Phe Gln
                165                 170                 175
Asp Tyr His Ser Phe Val Thr His Gly Cys Thr Val Asp Asn Pro Val
            180                 185                 190
Leu Glu Arg Phe Ile Ser Leu Phe Asn Ser Val Ser Gln Trp Val Gln
        195                 200                 205
Leu Met Ile Leu Ser Lys Pro Thr Ala Pro Gln Arg Ala Leu Val Ile
    210                 215                 220
Thr His Phe Val His Val Ala Glu Lys Leu Leu Gln Leu Gln Asn Phe
225                 230                 235                 240
Asn Thr Leu Met Ala Val Val Gly Gly Leu Ser His Ser Ser Ile Ser
                245                 250                 255
Arg Leu Lys Glu Thr His Ser His Val Ser Pro Glu Thr Ile Lys Leu
            260                 265                 270
Trp Glu Gly Leu Thr Glu Leu Val Thr Ala Thr Gly Asn Tyr Gly Asn
        275                 280                 285
Tyr Arg Arg Arg Leu Ala Ala Cys Val Gly Phe Arg Phe Pro Ile Leu
    290                 295                 300
Gly Val His Leu Lys Asp Leu Val Ala Leu Gln Leu Ala Leu Pro Asp
305                 310                 315                 320
Trp Leu Asp Pro Ala Arg Thr Arg Leu Asn Gly Ala Lys Met Lys Gln
                325                 330                 335
Leu Phe Ser Ile Leu Glu Glu Leu Ala Met Val Thr Ser Leu Arg Pro
            340                 345                 350
Pro Val Gln Ala Asn Pro Asp Leu Leu Ser Leu Leu Thr Val Ser Leu
        355                 360                 365
Asp Gln Tyr Gln Thr Glu Asp Glu Leu Tyr Gln Leu Ser Leu Gln Arg
370                 375                 380
Glu Pro Arg Ser Lys Ser Pro Thr Ser Pro Thr Ser Cys Thr Pro
385                 390                 395                 400
Pro Pro Arg Pro Val Leu Glu Glu Trp Thr Ser Ala Ala Lys Pro
                405                 410                 415
Lys Leu Asp Gln Ala Leu Val Val Glu His Ile Glu Lys Met Val Glu
            420                 425                 430
Ser Val Phe Arg Asn Phe Asp Val Asp Gly Asp Gly His Ile Ser Gln
        435                 440                 445
Glu Glu Phe Gln Ile Ile Arg Gly Asn Phe Pro Tyr Leu Ser Ala Phe
    450                 455                 460
Gly Asp Leu Asp Gln Asn Gln Asp Gly Cys Ile Ser Arg Glu Glu Met
465                 470                 475                 480
Val Ser Tyr Phe Leu Arg Ser Ser Val Leu Gly Gly Arg Met Gly
                485                 490                 495
Phe Val His Asn Phe Gln Glu Ser Asn Ser Leu Arg Pro Val Ala Cys
            500                 505                 510
Arg His Cys Lys Ala Leu Ile Leu Gly Ile Tyr Lys Gln Gly Leu Lys
        515                 520                 525
Cys Arg Ala Cys Gly Val Asn Cys His Lys Gln Cys Lys Asp Arg Leu
530                 535                 540
```

-continued

| | | | | | | | | | | | | | | | |
|---|---|---|---|---|---|---|---|---|---|---|---|---|---|---|---|
|Ser|Val|Glu|Cys|Arg|Arg|Arg|Ala|Gln|Ser|Val|Ser|Leu|Glu|Gly|Ser|
|545| | | |550| | | |555| | | |560| | | |

| | | | | | | | | | | | |
|---|---|---|---|---|---|---|---|---|---|---|---|
|Ala|Pro|Ser|Pro|Ser|Pro|Met|His|Ser|His|His|Arg|Ala|Phe|Ser|
| | | | |565| | | |570| | | |575| | |

Phe Ser Leu Pro Arg Pro Gly Arg Arg Gly Ser Arg Pro Glu Ile
            580              585              590

Arg Glu Glu Val Gln Thr Val Glu Asp Gly Val Phe Asp Ile His
        595              600              605

Leu

<210> SEQ ID NO 5
<211> LENGTH: 3624
<212> TYPE: DNA
<213> ORGANISM: Rattus norvegicus
<220> FEATURE:
<221> NAME/KEY: CDS
<222> LOCATION: (145)..(2529)

<400> SEQUENCE: 5

```
gcgcctgggt cggctcgccg ggctccgaga gtggccggct ccgggctgcg agggccggcg      60
gcggccgagg gatgcgccgc tcccggccga gccgatccca ccgctccagg tgagacggct     120 ccagggcgc agagagccgc ggcc atg gga acc ctg ggc aag gcg aga gag         171
                          Met Gly Thr Leu Gly Lys Ala Arg Glu
                           1               5 gct ccg cgg aaa cct tgc cat ggc tcc aga gct ggc ccc aaa gga aga        219
Ala Pro Arg Lys Pro Cys His Gly Ser Arg Ala Gly Pro Lys Gly Arg
 10              15                  20                  25 cta gag gcc aaa tca acc aac agt cct ctc cct gcc cag ccc agc ttg        267
Leu Glu Ala Lys Ser Thr Asn Ser Pro Leu Pro Ala Gln Pro Ser Leu
                 30                  35                  40 gcc cag atc acc cag ttc cga atg atg gtg tcc ctg gga cat ctg gcc        315
Ala Gln Ile Thr Gln Phe Arg Met Met Val Ser Leu Gly His Leu Ala
             45                  50                  55 aaa gga gcc agc ctg gat gat ctt att gac agc tgc att caa tct ttc        363
Lys Gly Ala Ser Leu Asp Asp Leu Ile Asp Ser Cys Ile Gln Ser Phe
         60                  65                  70 gat gca gat gga aac ctg tgt cga agt aac cag ctg tta caa gtc atg        411
Asp Ala Asp Gly Asn Leu Cys Arg Ser Asn Gln Leu Leu Gln Val Met
     75                  80                  85 cta acc atg cac cga atc atc atc tcc tcg gcc gag ctg ctg caa aaa        459
Leu Thr Met His Arg Ile Ile Ile Ser Ser Ala Glu Leu Leu Gln Lys
 90                  95                 100                 105 ctc atg aat cta tat aag gac gcc ctg gaa aag aat tct cca gga att        507
Leu Met Asn Leu Tyr Lys Asp Ala Leu Glu Lys Asn Ser Pro Gly Ile
                110                 115                 120 tgc ttg aag atc tgc tat ttt gtc agg tat tgg ata aca gaa ttc tgg        555
Cys Leu Lys Ile Cys Tyr Phe Val Arg Tyr Trp Ile Thr Glu Phe Trp
            125                 130                 135 atc atg ttc aaa atg gat gcc agc ttg acc agc acc atg gaa gag ttt        603
Ile Met Phe Lys Met Asp Ala Ser Leu Thr Ser Thr Met Glu Glu Phe
        140                 145                 150 cag gac ctg gtg aaa gcc aat ggt gag gag tcc cac tgc cac ctc atc        651
Gln Asp Leu Val Lys Ala Asn Gly Glu Glu Ser His Cys His Leu Ile
    155                 160                 165 gac aca aca caa att aat tct cga gac tgg tcc agg aaa ctg act cag        699
Asp Thr Thr Gln Ile Asn Ser Arg Asp Trp Ser Arg Lys Leu Thr Gln
170                 175                 180                 185 agg ata aaa tca aat acc agc aag aag cgg aaa gtg tcc ctg ctg ttt        747
Arg Ile Lys Ser Asn Thr Ser Lys Lys Arg Lys Val Ser Leu Leu Phe
```

-continued

|     |     |     | 190 |     |     |     |     | 195 |     |     |     |     | 200 |     |     |      |
|-----|-----|-----|-----|-----|-----|-----|-----|-----|-----|-----|-----|-----|-----|-----|-----|------|
| gac | cat | ctt | gaa | cct | gaa | gaa | ctg | tct | gaa | cac | ctc | acc | tac | ctt | gag | 795  |
| Asp | His | Leu | Glu | Pro | Glu | Glu | Leu | Ser | Glu | His | Leu | Thr | Tyr | Leu | Glu |      |
|     |     |     | 205 |     |     |     | 210 |     |     |     |     | 215 |     |     |     |      |

| ttc | aag | tcc | ttc | cga | cgg | ata | tct | ttc | tct | gat | tat | cag | aat | tac | ctt | 843 |
| Phe | Lys | Ser | Phe | Arg | Arg | Ile | Ser | Phe | Ser | Asp | Tyr | Gln | Asn | Tyr | Leu |     |
|     |     |     | 220 |     |     |     | 225 |     |     |     |     | 230 |     |     |     |     |

| gta | aac | agc | tgc | gta | aag | gag | aac | ccc | acc | atg | gag | cgg | tcc | att | gcc | 891 |
| Val | Asn | Ser | Cys | Val | Lys | Glu | Asn | Pro | Thr | Met | Glu | Arg | Ser | Ile | Ala |     |
|     |     |     | 235 |     |     |     | 240 |     |     |     |     | 245 |     |     |     |     |

| ctg | tgc | aat | ggc | atc | tcc | cag | tgg | gta | caa | ctg | atg | gtt | ctc | agc | cgt | 939 |
| Leu | Cys | Asn | Gly | Ile | Ser | Gln | Trp | Val | Gln | Leu | Met | Val | Leu | Ser | Arg |     |
| 250 |     |     |     |     | 255 |     |     |     |     | 260 |     |     |     |     | 265 |     |

| ccc | acc | cca | cag | ctc | cgg | gca | gag | gtc | ttc | atc | aag | ttc | atc | cat | gtg | 987 |
| Pro | Thr | Pro | Gln | Leu | Arg | Ala | Glu | Val | Phe | Ile | Lys | Phe | Ile | His | Val |     |
|     |     |     |     | 270 |     |     |     |     | 275 |     |     |     |     | 280 |     |     |

| gct | cag | aag | ctc | cac | cag | cta | cag | aac | ttc | aac | acg | cta | atg | gct | gtg | 1035 |
| Ala | Gln | Lys | Leu | His | Gln | Leu | Gln | Asn | Phe | Asn | Thr | Leu | Met | Ala | Val |      |
|     |     |     |     | 285 |     |     |     |     | 290 |     |     |     |     | 295 |     |      |

| atc | ggg | gga | ctg | tgt | cac | agc | tcc | atc | tcc | agg | ctc | aag | gag | aca | agt | 1083 |
| Ile | Gly | Gly | Leu | Cys | His | Ser | Ser | Ile | Ser | Arg | Leu | Lys | Glu | Thr | Ser |      |
|     |     |     | 300 |     |     |     |     | 305 |     |     |     |     | 310 |     |     |      |

| tca | cat | gtc | cca | cat | gag | atc | aat | aag | gtt | ctg | ggt | gag | atg | act | gaa | 1131 |
| Ser | His | Val | Pro | His | Glu | Ile | Asn | Lys | Val | Leu | Gly | Glu | Met | Thr | Glu |      |
|     | 315 |     |     |     |     | 320 |     |     |     |     | 325 |     |     |     |     |      |

| ctg | ctg | tcc | tcc | tgc | aga | aac | tat | gac | aac | tac | agg | cga | gcc | tat | ggt | 1179 |
| Leu | Leu | Ser | Ser | Cys | Arg | Asn | Tyr | Asp | Asn | Tyr | Arg | Arg | Ala | Tyr | Gly |      |
| 330 |     |     |     |     | 335 |     |     |     |     | 340 |     |     |     |     | 345 |      |

| gag | tgc | acc | cac | ttc | aaa | atc | ccc | ata | ctg | ggt | gtg | cac | ctc | aag | gac | 1227 |
| Glu | Cys | Thr | His | Phe | Lys | Ile | Pro | Ile | Leu | Gly | Val | His | Leu | Lys | Asp |      |
|     |     |     |     | 350 |     |     |     |     | 355 |     |     |     |     | 360 |     |      |

| ctc | ata | tcc | cta | tat | gaa | gcc | atg | cct | gac | tac | ctg | gaa | gac | ggg | aag | 1275 |
| Leu | Ile | Ser | Leu | Tyr | Glu | Ala | Met | Pro | Asp | Tyr | Leu | Glu | Asp | Gly | Lys |      |
|     |     |     | 365 |     |     |     |     | 370 |     |     |     |     | 375 |     |     |      |

| gtg | aat | gtc | caa | aag | ctc | ctg | gcc | ctt | tac | aat | cac | atc | aat | gag | ttg | 1323 |
| Val | Asn | Val | Gln | Lys | Leu | Leu | Ala | Leu | Tyr | Asn | His | Ile | Asn | Glu | Leu |      |
|     |     |     | 380 |     |     |     |     | 385 |     |     |     |     | 390 |     |     |      |

| gtc | cag | ctg | cag | gac | gtg | gcc | cca | cca | ttg | gat | gcc | aac | aag | gac | ctg | 1371 |
| Val | Gln | Leu | Gln | Asp | Val | Ala | Pro | Pro | Leu | Asp | Ala | Asn | Lys | Asp | Leu |      |
|     |     |     | 395 |     |     |     |     | 400 |     |     |     |     | 405 |     |     |      |

| gtg | cac | ctg | ctg | acg | tta | tcc | ctg | gat | cta | tac | tac | acc | gaa | gat | gaa | 1419 |
| Val | His | Leu | Leu | Thr | Leu | Ser | Leu | Asp | Leu | Tyr | Tyr | Thr | Glu | Asp | Glu |      |
| 410 |     |     |     |     | 415 |     |     |     |     | 420 |     |     |     |     | 425 |      |

| atc | tat | gag | ctt | tcc | tac | gcc | cgt | gaa | cca | agg | aac | cac | agg | gcc | ccg | 1467 |
| Ile | Tyr | Glu | Leu | Ser | Tyr | Ala | Arg | Glu | Pro | Arg | Asn | His | Arg | Ala | Pro |      |
|     |     |     |     | 430 |     |     |     |     | 435 |     |     |     |     | 440 |     |      |

| cca | ctg | aca | cct | tcg | aag | cca | cca | gtt | gta | gtg | gac | tgg | gcc | tct | gga | 1515 |
| Pro | Leu | Thr | Pro | Ser | Lys | Pro | Pro | Val | Val | Val | Asp | Trp | Ala | Ser | Gly |      |
|     |     |     |     | 445 |     |     |     |     | 450 |     |     |     |     | 455 |     |      |

| gtg | tct | ccc | aaa | cct | gac | ccg | aag | acc | atc | agc | aaa | cac | gtc | caa | agg | 1563 |
| Val | Ser | Pro | Lys | Pro | Asp | Pro | Lys | Thr | Ile | Ser | Lys | His | Val | Gln | Arg |      |
|     |     |     | 460 |     |     |     |     | 465 |     |     |     |     | 470 |     |     |      |

| atg | gtg | gat | tct | gtc | ttt | aag | aac | tat | gat | ctc | gac | cag | gat | gga | tat | 1611 |
| Met | Val | Asp | Ser | Val | Phe | Lys | Asn | Tyr | Asp | Leu | Asp | Gln | Asp | Gly | Tyr |      |
|     | 475 |     |     |     |     | 480 |     |     |     |     | 485 |     |     |     |     |      |

| atc | tct | cag | gag | gag | ttt | gaa | aag | att | gct | gcg | agc | ttt | cca | ttt | tcc | 1659 |
| Ile | Ser | Gln | Glu | Glu | Phe | Glu | Lys | Ile | Ala | Ala | Ser | Phe | Pro | Phe | Ser |      |
| 490 |     |     |     |     | 495 |     |     |     |     | 500 |     |     |     |     | 505 |      |

| ttc | tgt | gtg | atg | gac | aaa | gat | agg | gag | ggc | ctc | atc | agc | aga | gac | gag | 1707 |

-continued

```
                Phe Cys Val Met Asp Lys Asp Arg Glu Gly Leu Ile Ser Arg Asp Glu
                                510                 515                 520 atc aca gcc tac ttc atg agg gcc agc tcc atc tat tcc aag ctg ggc              1755
Ile Thr Ala Tyr Phe Met Arg Ala Ser Ser Ile Tyr Ser Lys Leu Gly
            525                 530                 535 cta ggc ttt cca cac aac ttt caa gag acc act tac ctg aag ccc acc              1803
Leu Gly Phe Pro His Asn Phe Gln Glu Thr Thr Tyr Leu Lys Pro Thr
        540                 545                 550 ttc tgt gac aac tgt gct ggc ttt ctc tgg ggt gtg atc aag caa ggc              1851
Phe Cys Asp Asn Cys Ala Gly Phe Leu Trp Gly Val Ile Lys Gln Gly
    555                 560                 565 tat cgc tgt aaa gac tgt ggg atg aac tgc cac aaa cag tgc aaa gac              1899
Tyr Arg Cys Lys Asp Cys Gly Met Asn Cys His Lys Gln Cys Lys Asp
570                 575                 580                 585 ctg gta gtg ttt gag tgc aag aaa cga tcc aag agc ccg gcg gta tcc              1947
Leu Val Val Phe Glu Cys Lys Lys Arg Ser Lys Ser Pro Ala Val Ser
                590                 595                 600 aca gaa aac atc agc tct gtg gtg cca atg tcc act ctt tgt cca ctg              1995
Thr Glu Asn Ile Ser Ser Val Val Pro Met Ser Thr Leu Cys Pro Leu
            605                 610                 615 gga acc aaa gat ctg ctc cat gca ccc gaa gaa gga tct ttc att ttc              2043
Gly Thr Lys Asp Leu Leu His Ala Pro Glu Glu Gly Ser Phe Ile Phe
        620                 625                 630 cag aat gga gag gtt gtg gac cac agt gag gag agc aag gat agg acc              2091
Gln Asn Gly Glu Val Val Asp His Ser Glu Glu Ser Lys Asp Arg Thr
    635                 640                 645 atc atg ctc ttg ggc gta tcc tca cag aaa att tca gtt cgg ctg aag              2139
Ile Met Leu Leu Gly Val Ser Ser Gln Lys Ile Ser Val Arg Leu Lys
650                 655                 660                 665 agg act gtt gcc cac aag acc acc cag aca gaa tca ttt cct tgg gtt              2187
Arg Thr Val Ala His Lys Thr Thr Gln Thr Glu Ser Phe Pro Trp Val
                670                 675                 680 ggc ggc gag atg ccc cct ggt cac ttt gtg ctg act tct cca aga aag              2235
Gly Gly Glu Met Pro Pro Gly His Phe Val Leu Thr Ser Pro Arg Lys
            685                 690                 695 tca gca caa ggg gct ctt tat gtg cac agt cca gca tct ccg tgc ccc              2283
Ser Ala Gln Gly Ala Leu Tyr Val His Ser Pro Ala Ser Pro Cys Pro
        700                 705                 710 agc cca gca ctg gtc cgg aag cgg gca ttc gtc aag tgg gag aac aaa              2331
Ser Pro Ala Leu Val Arg Lys Arg Ala Phe Val Lys Trp Glu Asn Lys
    715                 720                 725 gag tcc ctt atc aaa cca aaa cca gag ctt cac ctc agg ctc cgg acc              2379
Glu Ser Leu Ile Lys Pro Lys Pro Glu Leu His Leu Arg Leu Arg Thr
730                 735                 740                 745 tac caa gaa ctg gaa cag gag gta aat acc ctg agg gca gat aac gat              2427
Tyr Gln Glu Leu Glu Gln Glu Val Asn Thr Leu Arg Ala Asp Asn Asp
                750                 755                 760 gct ctg aag atc cag ctg aag tat gca cag aaa caa ata gaa tcc ctg              2475
Ala Leu Lys Ile Gln Leu Lys Tyr Ala Gln Lys Gln Ile Glu Ser Leu
            765                 770                 775 cag ctt ggc aaa agc aat cac gtc tta gca cag atg gac cac ggt gat              2523
Gln Leu Gly Lys Ser Asn His Val Leu Ala Gln Met Asp His Gly Asp
        780                 785                 790 ggt act taatccagaa attcaaggaa cagaatctgc agacgggttt actgggatct              2579
Gly Thr
    795 cacttcaaaa ctgattgcag aggttcagca actttagact gattgacttt taaagggcag           2639 agatagccac tgttattggt gtccttggtt ttttccctaa ctgtctttaa tgtgagtcgt           2699
```

-continued

```
gggttttcag tcagttgagt aaaagggaag aaaagttcca gcatgtaaaa cactgagcag      2759
tcatattcta acctttctt tcttttactg aaaccaatac caaacatgtg ctaaaataag       2819
agtatagttt cctgacagtg tctcaggcag cctgctttac tgattcgcac ttagataaag     2879
agcccctggt gaatcaattt gctgccttcc ccagggtttc tgcaaactgg gagttacttt     2939
gttctacccg aaaacctgct cataatggaa acaataccct aaaagtggtg actttgacat     2999
gcctgcattg tttgtgaagc tgatccctac cttattcact acctcagatc tcaagagcct     3059
ctttccctgt cctttacttg cccctatttt cctcccttgc ttgtaggcac atcagcatat     3119
ctacctagaa gtgacctcct agagatgtag cctgtgttta aatccagagc ttcttaattg     3179
aacttgacat tgtctgattg caggccaact tatagctcta ggtcttagtc attatgaaat     3239
acaaaataaa actacccata atcatcaatt accatgtcat acacagaact cattatctaa     3299
gtcaaacgac gtaaacacgc ctgtccagat agtctttctt tagtggatag aattaacaat     3359
ctgtgacctt ttaaaagaca tggtctgtga acagtgttta gttcttcacg ttctagtctc     3419
tctctctctc tctctctctc tctctctctc tctctcaagt aaactatcgt                 3479
aaggtcctct tttgaactga atctgtgctt aaaattgtct tcacttttat tatctacaaa     3539
taagctatgg gaggcgatgg ctttaacagc tgacagcatt tacctatgtg tagaatatgt     3599
gtatatagta tcaggcatgc atgga                                           3624
```

<210> SEQ ID NO 6
<211> LENGTH: 795
<212> TYPE: PRT
<213> ORGANISM: Rattus norvegicus

<400> SEQUENCE: 6

```
Met Gly Thr Leu Gly Lys Ala Arg Glu Ala Pro Arg Lys Pro Cys His
1               5                   10                  15

Gly Ser Arg Ala Gly Pro Lys Gly Arg Leu Glu Ala Lys Ser Thr Asn
            20                  25                  30

Ser Pro Leu Pro Ala Gln Pro Ser Leu Ala Gln Ile Thr Gln Phe Arg
        35                  40                  45

Met Met Val Ser Leu Gly His Leu Ala Lys Gly Ala Ser Leu Asp Asp
    50                  55                  60

Leu Ile Asp Ser Cys Ile Gln Ser Phe Asp Ala Asp Gly Asn Leu Cys
65                  70                  75                  80

Arg Ser Asn Gln Leu Leu Gln Val Met Leu Thr Met His Arg Ile Ile
                85                  90                  95

Ile Ser Ser Ala Glu Leu Leu Gln Lys Leu Met Asn Leu Tyr Lys Asp
            100                 105                 110

Ala Leu Glu Lys Asn Ser Pro Gly Ile Cys Leu Lys Ile Cys Tyr Phe
        115                 120                 125

Val Arg Tyr Trp Ile Thr Glu Phe Trp Ile Met Phe Lys Met Asp Ala
    130                 135                 140

Ser Leu Thr Ser Thr Met Glu Glu Phe Gln Asp Leu Val Lys Ala Asn
145                 150                 155                 160

Gly Glu Glu Ser His Cys His Leu Ile Asp Thr Thr Gln Ile Asn Ser
                165                 170                 175

Arg Asp Trp Ser Arg Lys Leu Thr Gln Arg Ile Lys Ser Asn Thr Ser
            180                 185                 190

Lys Lys Arg Lys Val Ser Leu Leu Phe Asp His Leu Glu Pro Glu Glu
        195                 200                 205
```

-continued

```
Leu Ser Glu His Leu Thr Tyr Leu Glu Phe Lys Ser Phe Arg Arg Ile
    210                 215                 220

Ser Phe Ser Asp Tyr Gln Asn Tyr Leu Val Asn Ser Cys Val Lys Glu
225                 230                 235                 240

Asn Pro Thr Met Glu Arg Ser Ile Ala Leu Cys Asn Gly Ile Ser Gln
                245                 250                 255

Trp Val Gln Leu Met Val Leu Ser Arg Pro Thr Pro Gln Leu Arg Ala
                260                 265                 270

Glu Val Phe Ile Lys Phe Ile His Val Ala Gln Lys Leu His Gln Leu
                275                 280                 285

Gln Asn Phe Asn Thr Leu Met Ala Val Ile Gly Gly Leu Cys His Ser
    290                 295                 300

Ser Ile Ser Arg Leu Lys Glu Thr Ser Ser His Val Pro His Glu Ile
305                 310                 315                 320

Asn Lys Val Leu Gly Glu Met Thr Glu Leu Leu Ser Ser Cys Arg Asn
                325                 330                 335

Tyr Asp Asn Tyr Arg Arg Ala Tyr Gly Glu Cys Thr His Phe Lys Ile
                340                 345                 350

Pro Ile Leu Gly Val His Leu Lys Asp Leu Ile Ser Leu Tyr Glu Ala
                355                 360                 365

Met Pro Asp Tyr Leu Glu Asp Gly Lys Val Asn Val Gln Lys Leu Leu
    370                 375                 380

Ala Leu Tyr Asn His Ile Asn Glu Leu Val Gln Leu Gln Asp Val Ala
385                 390                 395                 400

Pro Pro Leu Asp Ala Asn Lys Asp Leu Val His Leu Leu Thr Leu Ser
                405                 410                 415

Leu Asp Leu Tyr Tyr Thr Glu Asp Glu Ile Tyr Glu Leu Ser Tyr Ala
                420                 425                 430

Arg Glu Pro Arg Asn His Arg Ala Pro Pro Leu Thr Pro Ser Lys Pro
    435                 440                 445

Pro Val Val Asp Trp Ala Ser Gly Val Ser Pro Lys Pro Asp Pro
450                 455                 460

Lys Thr Ile Ser Lys His Val Gln Arg Met Val Asp Ser Val Phe Lys
465                 470                 475                 480

Asn Tyr Asp Leu Asp Gln Asp Gly Tyr Ile Ser Gln Glu Glu Phe Glu
                485                 490                 495

Lys Ile Ala Ala Ser Phe Pro Phe Ser Phe Cys Val Met Asp Lys Asp
                500                 505                 510

Arg Glu Gly Leu Ile Ser Arg Asp Glu Ile Thr Ala Tyr Phe Met Arg
    515                 520                 525

Ala Ser Ser Ile Tyr Ser Lys Leu Gly Leu Gly Phe Pro His Asn Phe
530                 535                 540

Gln Glu Thr Thr Tyr Leu Lys Pro Thr Phe Cys Asp Asn Cys Ala Gly
545                 550                 555                 560

Phe Leu Trp Gly Val Ile Lys Gln Gly Tyr Arg Cys Lys Asp Cys Gly
                565                 570                 575

Met Asn Cys His Lys Gln Cys Lys Asp Leu Val Val Phe Glu Cys Lys
                580                 585                 590

Lys Arg Ser Lys Ser Pro Ala Val Ser Thr Glu Asn Ile Ser Ser Val
    595                 600                 605

Val Pro Met Ser Thr Leu Cys Pro Leu Gly Thr Lys Asp Leu Leu His
610                 615                 620

Ala Pro Glu Glu Gly Ser Phe Ile Phe Gln Asn Gly Glu Val Val Asp
```

-continued

```
          625                 630                 635                 640
His Ser Glu Glu Ser Lys Asp Arg Thr Ile Met Leu Leu Gly Val Ser
                    645                 650                 655
Ser Gln Lys Ile Ser Val Arg Leu Lys Arg Thr Val Ala His Lys Thr
                660                 665                 670
Thr Gln Thr Glu Ser Phe Pro Trp Val Gly Glu Met Pro Pro Gly
            675                 680                 685
His Phe Val Leu Thr Ser Pro Arg Lys Ser Ala Gln Gly Ala Leu Tyr
        690                 695                 700
Val His Ser Pro Ala Ser Pro Cys Pro Ser Pro Ala Leu Val Arg Lys
705                 710                 715                 720
Arg Ala Phe Val Lys Trp Glu Asn Lys Glu Ser Leu Ile Lys Pro Lys
                725                 730                 735
Pro Glu Leu His Leu Arg Leu Arg Thr Tyr Gln Leu Glu Gln Glu
            740                 745                 750
Val Asn Thr Leu Arg Ala Asp Asn Asp Ala Leu Lys Ile Gln Leu Lys
                755                 760                 765
Tyr Ala Gln Lys Gln Ile Glu Ser Leu Gln Leu Gly Lys Ser Asn His
    770                 775                 780
Val Leu Ala Gln Met Asp His Gly Asp Gly Thr
785                 790                 795

<210> SEQ ID NO 7
<211> LENGTH: 5075
<212> TYPE: DNA
<213> ORGANISM: Homo sapiens
<220> FEATURE:
<221> NAME/KEY: CDS
<222> LOCATION: (104)..(2494)

<400> SEQUENCE: 7 cccgggggg agagagccgg caggcggcgg cggtggtggc gggggcgatg cgccgcgccc        60
ggccgcgcta ggtgagccgg caccgggagc gcgggccgcg gcc atg ggc acc ctg       115
                                                Met Gly Thr Leu
                                                  1 ggc aag gcg aga gag gct ccg cgg aaa cct tcc cat ggc tgc aga gct       163
Gly Lys Ala Arg Glu Ala Pro Arg Lys Pro Ser His Gly Cys Arg Ala
  5              10                 15                  20 gcc tct aaa gca aga cta gag gca aag cca gcc aac agc ccc ttc ccc       211
Ala Ser Lys Ala Arg Leu Glu Ala Lys Pro Ala Asn Ser Pro Phe Pro
                25                  30                  35 tcc cat ccc agc ttg gcc cac atc acc cag ttc cga atg atg gtg tct       259
Ser His Pro Ser Leu Ala His Ile Thr Gln Phe Arg Met Met Val Ser
            40                  45                  50 ctg gga cat tta gcc aaa gga gcc agc ctg gac gat ctc att gac agc       307
Leu Gly His Leu Ala Lys Gly Ala Ser Leu Asp Asp Leu Ile Asp Ser
        55                  60                  65 tgc att caa tct ttt gat gca gat gga aac ctg tgt cga agt aac caa       355
Cys Ile Gln Ser Phe Asp Ala Asp Gly Asn Leu Cys Arg Ser Asn Gln
    70                  75                  80 ctg ttg caa gtc atg ctg acc atg cac cga att gtc atc tcc tct gca       403
Leu Leu Gln Val Met Leu Thr Met His Arg Ile Val Ile Ser Ser Ala
85                  90                  95                 100 gaa ctg ctc caa aaa gtt atc acc ctc tat aag gat gct ttg gca aag       451
Glu Leu Leu Gln Lys Val Ile Thr Leu Tyr Lys Asp Ala Leu Ala Lys
                105                 110                 115 aat tca cca gga ctt tgc ctg aag atc tgt tat ttt gta agg tat tgg       499
Asn Ser Pro Gly Leu Cys Leu Lys Ile Cys Tyr Phe Val Arg Tyr Trp
```

-continued

```
                  120                     125                     130
ata aca gaa ttc tgg gtc atg ttt aaa atg gac gcc agc ttg aca gac         547
Ile Thr Glu Phe Trp Val Met Phe Lys Met Asp Ala Ser Leu Thr Asp
        135                     140                     145 act atg gag gag ttt cag gaa ctg gtg aaa gct aag ggt gag gag tta         595
Thr Met Glu Glu Phe Gln Glu Leu Val Lys Ala Lys Gly Glu Glu Leu
    150                     155                     160 cat tgc cgc ctg att gac aca act caa atc aat gcc cgt gac tgg tcc         643
His Cys Arg Leu Ile Asp Thr Thr Gln Ile Asn Ala Arg Asp Trp Ser
165                     170                     175                     180 agg aaa ctt act caa agg ata aaa tca aat acc agc aag aaa cgg aaa         691
Arg Lys Leu Thr Gln Arg Ile Lys Ser Asn Thr Ser Lys Lys Arg Lys
                185                     190                     195 gtc tcc ctg ctc ttt gac cat ctg gaa cca gaa gag cta tcc gag cac         739
Val Ser Leu Leu Phe Asp His Leu Glu Pro Glu Glu Leu Ser Glu His
            200                     205                     210 ctc acc tac ctt gag ttc aag tct ttc cgg agg ata tcg ttc tct gat         787
Leu Thr Tyr Leu Glu Phe Lys Ser Phe Arg Arg Ile Ser Phe Ser Asp
        215                     220                     225 tat cag aat tac ctt gta aat agc tgt gtg aag gaa aac ccc acc atg         835
Tyr Gln Asn Tyr Leu Val Asn Ser Cys Val Lys Glu Asn Pro Thr Met
    230                     235                     240 gag cga tct att gct ctg tgc aac ggc atc tcc cag tgg gta caa ctg         883
Glu Arg Ser Ile Ala Leu Cys Asn Gly Ile Ser Gln Trp Val Gln Leu
245                     250                     255                     260 atg gtt ctc agc cgc ccc acg ccg cag ctc cga gca gaa gtc ttc atc         931
Met Val Leu Ser Arg Pro Thr Pro Gln Leu Arg Ala Glu Val Phe Ile
                265                     270                     275 aag ttc atc cag gtg gct cag aag ctc cac caa cta cag aac ttc aat         979
Lys Phe Ile Gln Val Ala Gln Lys Leu His Gln Leu Gln Asn Phe Asn
            280                     285                     290 aca ctg atg gct gtg ata ggt ggg ctg tgt cac agc tca atc tcg agg        1027
Thr Leu Met Ala Val Ile Gly Gly Leu Cys His Ser Ser Ile Ser Arg
        295                     300                     305 ctc aag gag aca agt tcg cat gtc cca cat gaa atc aat aag gtt ctc        1075
Leu Lys Glu Thr Ser Ser His Val Pro His Glu Ile Asn Lys Val Leu
    310                     315                     320 ggt gag atg act gag ctg ctg tcc tcc tcc aga aac tac gac aat tac        1123
Gly Glu Met Thr Glu Leu Leu Ser Ser Ser Arg Asn Tyr Asp Asn Tyr
325                     330                     335                     340 cgg cga gcc tat gga gag tgc acc gac ttc aag atc ccc att ctg ggt        1171
Arg Arg Ala Tyr Gly Glu Cys Thr Asp Phe Lys Ile Pro Ile Leu Gly
                345                     350                     355 gtg cat ctc aag gac ctc atc tcc ctg tat gaa gcc atg cct gac tat        1219
Val His Leu Lys Asp Leu Ile Ser Leu Tyr Glu Ala Met Pro Asp Tyr
            360                     365                     370 ctg ggg gac ggg aaa gtg aac gtc cat aag cta ctg gcc cta tac aat        1267
Leu Gly Asp Gly Lys Val Asn Val His Lys Leu Leu Ala Leu Tyr Asn
        375                     380                     385 cat atc agt gaa ttg gtc cag ctg caa gag gtg gcc cca ccc ttg gag        1315
His Ile Ser Glu Leu Val Gln Leu Gln Glu Val Ala Pro Pro Leu Glu
    390                     395                     400 gct aac aag gac ttg gta cac ttg ctg acg tta tcc ctg gat ctt tac        1363
Ala Asn Lys Asp Leu Val His Leu Leu Thr Leu Ser Leu Asp Leu Tyr
405                     410                     415                     420 tac act gag gat gaa atc tat gag ctt tcc tat gcc cgg gaa cca agg        1411
Tyr Thr Glu Asp Glu Ile Tyr Glu Leu Ser Tyr Ala Arg Glu Pro Arg
                425                     430                     435 aac cac aga gct cca cca cta aca cct tca aag cca cca gta gta gtg        1459
```

-continued

|  |  |  |  |  |  |  |  |  |  |  |  |  |  |  |
|--|--|--|--|--|--|--|--|--|--|--|--|--|--|--|
| Asn | His | Arg | Ala | Pro | Pro | Leu | Thr | Pro | Ser | Lys | Pro | Pro | Val | Val | Val |
|  |  |  |  | 440 |  |  |  | 445 |  |  |  | 450 |  |  | gac tgg gct tct gga gtg tct ccc aaa cct gat cca aaa acc att agc     1507
Asp Trp Ala Ser Gly Val Ser Pro Lys Pro Asp Pro Lys Thr Ile Ser
        455                 460                 465 aaa cac gtc cag agg atg gtg gat tct gtc ttc aag aac tat gat cac     1555
Lys His Val Gln Arg Met Val Asp Ser Val Phe Lys Asn Tyr Asp His
470                 475                 480 gac cag gat gga tac att tct cag gaa gaa ttt gaa aag att gct gcg     1603
Asp Gln Asp Gly Tyr Ile Ser Gln Glu Glu Phe Glu Lys Ile Ala Ala
485                 490                 495                 500 agt ttt cca ttt tcc ttc tgt gtg atg gac aaa gac agg gaa ggc ctc     1651
Ser Phe Pro Phe Ser Phe Cys Val Met Asp Lys Asp Arg Glu Gly Leu
                505                 510                 515 atc agc agg gat gag atc aca gcc tac ttc atg aga gcc agc tca atc     1699
Ile Ser Arg Asp Glu Ile Thr Ala Tyr Phe Met Arg Ala Ser Ser Ile
            520                 525                 530 tat tcc aag ctg ggc ctg ggc ttt cct cac aac ttc caa gag acc acc     1747
Tyr Ser Lys Leu Gly Leu Gly Phe Pro His Asn Phe Gln Glu Thr Thr
        535                 540                 545 tac ctg aag ccc act ttt tgt gac aac tgt gct gga ttt ctc tgg gga     1795
Tyr Leu Lys Pro Thr Phe Cys Asp Asn Cys Ala Gly Phe Leu Trp Gly
550                 555                 560 gtg atc aaa caa gga tat cga tgt aaa gac tgc ggg atg aac tgt cac     1843
Val Ile Lys Gln Gly Tyr Arg Cys Lys Asp Cys Gly Met Asn Cys His
565                 570                 575                 580 aaa caa tgc aaa gat ctg gtt gtg ttt gag tgt aag aag cga gcc aag     1891
Lys Gln Cys Lys Asp Leu Val Val Phe Glu Cys Lys Lys Arg Ala Lys
                585                 590                 595 aac cca gta gct ccc aca gag aac aac act tct gtg ggg cca gtg tcc     1939
Asn Pro Val Ala Pro Thr Glu Asn Asn Thr Ser Val Gly Pro Val Ser
            600                 605                 610 aac ctt tgc tca ttg gga gcc aaa gat ctg ctc cat gca cct gag gaa     1987
Asn Leu Cys Ser Leu Gly Ala Lys Asp Leu Leu His Ala Pro Glu Glu
        615                 620                 625 gga cct ttt aca ttc cct aat ggg gag gct gtg gaa cat ggt gag gag     2035
Gly Pro Phe Thr Phe Pro Asn Gly Glu Ala Val Glu His Gly Glu Glu
630                 635                 640 agt aag gat cgg acc atc atg ctg atg gga gtg tcc tca cag aag att     2083
Ser Lys Asp Arg Thr Ile Met Leu Met Gly Val Ser Ser Gln Lys Ile
645                 650                 655                 660 tct ctt cgg ctg aag agg gct gtt gcc cac aag gcc acc cag act gaa     2131
Ser Leu Arg Leu Lys Arg Ala Val Ala His Lys Ala Thr Gln Thr Glu
                665                 670                 675 tca cag cct tgg att ggc agt gag ggc cct tca ggt ccc ttt gtg ctg     2179
Ser Gln Pro Trp Ile Gly Ser Glu Gly Pro Ser Gly Pro Phe Val Leu
            680                 685                 690 tct tcc cca agg aag aca gcc cag gat act cta tat gtg ctt ccc agt     2227
Ser Ser Pro Arg Lys Thr Ala Gln Asp Thr Leu Tyr Val Leu Pro Ser
        695                 700                 705 ccc acc tct cca tgt cct agc cca gtc ttg gtc aga aag cgg gct ttt     2275
Pro Thr Ser Pro Cys Pro Ser Pro Val Leu Val Arg Lys Arg Ala Phe
710                 715                 720 gtc aag tgg gag aat aaa gac tcc ctc ata aaa tca aag gag gag ctc     2323
Val Lys Trp Glu Asn Lys Asp Ser Leu Ile Lys Ser Lys Glu Glu Leu
725                 730                 735                 740 cgt cac ctc aga ctg cct acc tac caa gaa ctg gaa cag gaa ata aat     2371
Arg His Leu Arg Leu Pro Thr Tyr Gln Glu Leu Glu Gln Glu Ile Asn
                745                 750                 755

| | | |
|---|---|---|
| act ctg aaa gca gat aat gat gcc cta aag atc caa ctg aaa tat gca<br>Thr Leu Lys Ala Asp Asn Asp Ala Leu Lys Ile Gln Leu Lys Tyr Ala<br>          760                 765                 770 | | 2419 |
| cag aag aaa ata gaa tcc ctc cag ctt gaa aaa agc aat cat gtc tta<br>Gln Lys Lys Ile Glu Ser Leu Gln Leu Glu Lys Ser Asn His Val Leu<br>      775                 780                 785 | | 2467 |
| gct caa atg gag cag ggt gac tgt tct tagcccagaa actaagtagc<br>Ala Gln Met Glu Gln Gly Asp Cys Ser<br>      790                 795 | | 2514 |
| acaatctgta gatgagtata gtgatctcat ttcctaaact gtaatgcaca gacctgagga | | 2574 |
| actttacact gaccagcttt aaaacagtac tttaaaagga aaagcctgtt actgtttatt | | 2634 |
| tacctaaaag attcctaatg tgcagcactg ttttctcttt cagttagttg actcaaaggg | | 2694 |
| ggaaaactaa agaatgcaaa acttttgcta ttcataccac tgatgttcat caaaagtatg | | 2754 |
| cgatctaaaa catgactatc atttcctgac aatggggcat ctcggtggcc tgcctggctg | | 2814 |
| attcttcctt aaaactaaaa tctctggaaa atggatttgc ttcttaccct gtgttttctg | | 2874 |
| caaactgact tactttgttc cagccaaagc ttgctaataa tagaaaacta cccatattcc | | 2934 |
| aaaagtagat ttcctctgta tcccagcata ctttgtgaac ctggctccct cttcactacc | | 2994 |
| tcagatctaa tcaattagtc catgtaccct ccttcctcac tacagtcata acacatgagc | | 3054 |
| atatctacct agaagccaat ttctactgat gtagccacaa cttttagag cctattaaa | | 3114 |
| catgacgtta tccaattgca ggtcaactta gttgtagc cttacaactt acaggcatca | | 3174 |
| gaaaataagt aatcaaatta ggtacctgga aacatagcta ttaccatctc atattactgt | | 3234 |
| ctaattaaaa taaacataac gcaaacatgt tgtccttat atattctaca gtggatagaa | | 3294 |
| ttaggaattg atggcttaaa aaaaaaagtc tatgaagagt ctgttaact cttcatgttc | | 3354 |
| catctttctc ttctgaagta aactatttg aaagttctct ttttgaaatg aatttgtgct | | 3414 |
| taactgtctt cactattaat actatttaga aataagctaa ttggatcagt ggcttaaata | | 3474 |
| atagctgact gtgtgtacat atgtatataa tatgtatata caatatcagg catgcatgtg | | 3534 |
| gcttggaatt ttgtttcctc cataaaatgt ggaagtgaat taaacaagtt ttagtcattt | | 3594 |
| atacaaagtc acaaatataa agttcagttt gtcacaagat taaattgctc acaaggtaaa | | 3654 |
| attgtattgt ttggcaaaat cacaagtaac aatcctgtga gttttctatt atgaaggtta | | 3714 |
| ataataaatg ggctcattta gttgcctggg cacctattca caaattcatt tgtcagcctc | | 3774 |
| tttttagttc tcttaaaaaa aaaaaaatca tatgatcatt ttccttttg ggggtactta | | 3834 |
| gcttccatgc ctataaagtc tggtaccaga ctgacttgaa attcataaac aagttgtcca | | 3894 |
| attgccaaga atatgttaac aattaaaagt tccaaactaa agccaatagc accaagtctt | | 3954 |
| cataagaata caaagtatac atacagtatt gcttacctgg aggattcaga tcatttagga | | 4014 |
| attctctttg atgaaagatc agttcccatt tgagttcctc cttgcactga gttttagtga | | 4074 |
| tatagaacta gcttgtagtt agtgtttcat tacattataa agaatagttt tacacacgta | | 4134 |
| tttaccgttt tccaaattta aactcagaaa tacccaaagc aggcctgctt aagcccacta | | 4194 |
| cctggcatat aaacttatag taacactttg ttactttctt tttaatagga caagcatgag | | 4254 |
| ttaggacaaa ctctaaaaat tcatattctt cactattctt gttttccttt gattgatata | | 4314 |
| gaccaaagat ggtgtactct aattttttaa aacagtaatg gaacacaatt tttttcattc | | 4374 |
| ttcctcctct ccattcgaag taaagatccc cagttagttt ttatataaat aatctatagg | | 4434 |
| gattcaaaag gtgtcacagt ccacttaatt agtcaaatta gcaatggcta aacagtatca | | 4494 |
| agtactgcag aatttatcac tgaaatggat aagaggaaat agtttagtca caggttttta | | 4554 |

```
cagtccagca agggccaaag aggtatagta tacaagttaa tagtatttgt gttgagcaac    4614
atggggctag tgggatcaca gaaatctgga aaaaaaaaaa aaaaggcttt ggcttatcaa    4674
gcctagtgta aatttctgca tctcacacga ctttagtttg gccaggtatt tatctgccaa    4734
aacaaggaca aatcttgttg tattaacagc agggtcactt ctcatttct ttgctgactt    4794 accttttttac tgaccgttgt gaatttctgt ctcaaaatgt ataatataga aatgcaagaa    4854
aaaaacaaat gtacagattg taaagttttt tgatacctaa tgtaagtttt ctttgtgtaa    4914
tatttatatg ataaaagaca ttaggatccc tacaaaaaaa aaaaaaaaaa aaaaaaaaa    4974 aaaaaaaaaa aaaaaaaaaa aaaaaaaaa aaaaaaaaa aaaaaaggg atcgacaatt    5034 acgactcccc ggggggggccc ggtccaattc ccccaaaagg g                        5075
```

<210> SEQ ID NO 8
<211> LENGTH: 797
<212> TYPE: PRT
<213> ORGANISM: Homo sapiens

<400> SEQUENCE: 8

```
Met Gly Thr Leu Gly Lys Ala Arg Glu Ala Pro Arg Lys Pro Ser His
1               5                   10                  15

Gly Cys Arg Ala Ala Ser Lys Ala Arg Leu Glu Ala Lys Pro Ala Asn
                20                  25                  30

Ser Pro Phe Pro Ser His Pro Ser Leu Ala His Ile Thr Gln Phe Arg
            35                  40                  45

Met Met Val Ser Leu Gly His Leu Ala Lys Gly Ala Ser Leu Asp Asp
        50                  55                  60

Leu Ile Asp Ser Cys Ile Gln Ser Phe Asp Ala Asp Gly Asn Leu Cys
65                  70                  75                  80

Arg Ser Asn Gln Leu Leu Gln Val Met Leu Thr Met His Arg Ile Val
                85                  90                  95

Ile Ser Ser Ala Glu Leu Leu Gln Lys Val Ile Thr Leu Tyr Lys Asp
            100                 105                 110

Ala Leu Ala Lys Asn Ser Pro Gly Leu Cys Leu Lys Ile Cys Tyr Phe
        115                 120                 125

Val Arg Tyr Trp Ile Thr Glu Phe Trp Val Met Phe Lys Met Asp Ala
    130                 135                 140

Ser Leu Thr Asp Thr Met Glu Glu Phe Gln Glu Leu Val Lys Ala Lys
145                 150                 155                 160

Gly Glu Glu Leu His Cys Arg Leu Ile Asp Thr Thr Gln Ile Asn Ala
                165                 170                 175

Arg Asp Trp Ser Arg Lys Leu Thr Gln Arg Ile Lys Ser Asn Thr Ser
            180                 185                 190

Lys Lys Arg Lys Val Ser Leu Leu Phe Asp His Leu Glu Pro Glu Glu
        195                 200                 205

Leu Ser Glu His Leu Thr Tyr Leu Glu Phe Lys Ser Phe Arg Arg Ile
    210                 215                 220

Ser Phe Ser Asp Tyr Gln Asn Tyr Leu Val Asn Ser Cys Val Lys Glu
225                 230                 235                 240

Asn Pro Thr Met Glu Arg Ser Ile Ala Leu Cys Asn Gly Ile Ser Gln
                245                 250                 255

Trp Val Gln Leu Met Val Leu Ser Arg Pro Thr Pro Gln Leu Arg Ala
            260                 265                 270

Glu Val Phe Ile Lys Phe Ile Gln Val Ala Gln Lys Leu His Gln Leu
```

-continued

```
                275                 280                 285
Gln Asn Phe Asn Thr Leu Met Ala Val Ile Gly Gly Leu Cys His Ser
290                 295                 300

Ser Ile Ser Arg Leu Lys Glu Thr Ser Ser His Val Pro His Glu Ile
305                 310                 315                 320

Asn Lys Val Leu Gly Glu Met Thr Glu Leu Leu Ser Ser Ser Arg Asn
                325                 330                 335

Tyr Asp Asn Tyr Arg Arg Ala Tyr Gly Glu Cys Thr Asp Phe Lys Ile
                340                 345                 350

Pro Ile Leu Gly Val His Leu Lys Asp Leu Ile Ser Leu Tyr Glu Ala
                355                 360                 365

Met Pro Asp Tyr Leu Gly Asp Gly Lys Val Asn Val His Lys Leu Leu
370                 375                 380

Ala Leu Tyr Asn His Ile Ser Glu Leu Val Gln Leu Gln Glu Val Ala
385                 390                 395                 400

Pro Pro Leu Glu Ala Asn Lys Asp Leu Val His Leu Leu Thr Leu Ser
                405                 410                 415

Leu Asp Leu Tyr Tyr Thr Glu Asp Glu Ile Tyr Glu Leu Ser Tyr Ala
                420                 425                 430

Arg Glu Pro Arg Asn His Arg Ala Pro Pro Leu Thr Pro Ser Lys Pro
                435                 440                 445

Pro Val Val Asp Trp Ala Ser Gly Val Ser Pro Lys Pro Asp Pro
                450                 455                 460

Lys Thr Ile Ser Lys His Val Gln Arg Met Val Asp Ser Val Phe Lys
465                 470                 475                 480

Asn Tyr Asp His Asp Gln Asp Gly Tyr Ile Ser Gln Glu Glu Phe Glu
                485                 490                 495

Lys Ile Ala Ala Ser Phe Pro Phe Ser Phe Cys Val Met Asp Lys Asp
                500                 505                 510

Arg Glu Gly Leu Ile Ser Arg Asp Glu Ile Thr Ala Tyr Phe Met Arg
                515                 520                 525

Ala Ser Ser Ile Tyr Ser Lys Leu Gly Leu Gly Phe Pro His Asn Phe
530                 535                 540

Gln Glu Thr Thr Tyr Leu Lys Pro Thr Phe Cys Asp Asn Cys Ala Gly
545                 550                 555                 560

Phe Leu Trp Gly Val Ile Lys Gln Gly Tyr Arg Cys Lys Asp Cys Gly
                565                 570                 575

Met Asn Cys His Lys Gln Cys Lys Asp Leu Val Val Phe Glu Cys Lys
                580                 585                 590

Lys Arg Ala Lys Asn Pro Val Ala Pro Thr Glu Asn Asn Thr Ser Val
                595                 600                 605

Gly Pro Val Ser Asn Leu Cys Ser Leu Gly Ala Lys Asp Leu Leu His
610                 615                 620

Ala Pro Glu Glu Gly Pro Phe Thr Phe Pro Asn Gly Glu Ala Val Glu
625                 630                 635                 640

His Gly Glu Glu Ser Lys Asp Arg Thr Ile Met Leu Met Gly Val Ser
                645                 650                 655

Ser Gln Lys Ile Ser Leu Arg Leu Lys Arg Ala Val Ala His Lys Ala
                660                 665                 670

Thr Gln Thr Glu Ser Gln Pro Trp Ile Gly Ser Glu Gly Pro Ser Gly
                675                 680                 685

Pro Phe Val Leu Ser Ser Pro Arg Lys Thr Ala Gln Asp Thr Leu Tyr
690                 695                 700
```

-continued

```
Val Leu Pro Ser Pro Thr Ser Pro Cys Pro Ser Pro Val Leu Val Arg
705                 710                 715                 720

Lys Arg Ala Phe Val Lys Trp Glu Asn Lys Asp Ser Leu Ile Lys Ser
            725                 730                 735

Lys Glu Glu Leu Arg His Leu Arg Leu Pro Thr Tyr Gln Glu Leu Glu
        740                 745                 750

Gln Glu Ile Asn Thr Leu Lys Ala Asp Asn Asp Ala Leu Lys Ile Gln
            755                 760                 765

Leu Lys Tyr Ala Gln Lys Lys Ile Glu Ser Leu Gln Leu Glu Lys Ser
    770                 775                 780

Asn His Val Leu Ala Gln Met Glu Gln Gly Asp Cys Ser
785                 790                 795

<210> SEQ ID NO 9
<211> LENGTH: 3373
<212> TYPE: DNA
<213> ORGANISM: Rattus norvegicus
<220> FEATURE:
<221> NAME/KEY: CDS
<222> LOCATION: (197)..(2848)

<400> SEQUENCE: 9
cgctaagcct ggggtggtgg taggaaggtc cagctcctcc ggccgatggc tgtccacttt      60
cctcccccca tcacaggtca gctggccagg tgagaaccac tggcaggtgg gcccagctgt     120
ggtggagagt ccagctgtgg gggcaccgca ggtgcgaggt ctcccggacg tggttccgga    180
gggcacgctg ctcaat atg gtg ctg aag aga atg cac cgt ccc cgg tgc tgc   232
               Met Val Leu Lys Arg Met His Arg Pro Arg Cys Cys
                 1               5                  10 tct tac cag cta gtg ttc gag cac cgg cgc cca agc tgc atc cag gga    280
Ser Tyr Gln Leu Val Phe Glu His Arg Arg Pro Ser Cys Ile Gln Gly
        15                  20                  25 ctt cgc tgg acg cca ctt acc aac agt gag ggc tcc ctg gac ttc aga    328
Leu Arg Trp Thr Pro Leu Thr Asn Ser Glu Gly Ser Leu Asp Phe Arg
    30                  35                  40 gtg agc ctg gag cag gcc acc aca gag cat gtg cac aag gcc ggg aag    376
Val Ser Leu Glu Gln Ala Thr Thr Glu His Val His Lys Ala Gly Lys
45                  50                  55                  60 ctc ctg tac cgt cat ctc ttg gca acg tac cct acc ctc atc cga gac    424
Leu Leu Tyr Arg His Leu Leu Ala Thr Tyr Pro Thr Leu Ile Arg Asp
                65                  70                  75 aga aaa tac cat ctg cga cta cat cgg cag tgc tgc tct ggc cgg gag    472
Arg Lys Tyr His Leu Arg Leu His Arg Gln Cys Cys Ser Gly Arg Glu
            80                  85                  90 cta gtg gat ggg atc ttg gct ctg ggt ctt ggg gtc cac tca cgg agc    520
Leu Val Asp Gly Ile Leu Ala Leu Gly Leu Gly Val His Ser Arg Ser
        95                  100                 105 caa gct gtg ggc atc tgc cag gtg ttg ctg gat gag ggt gcc ctt tgc    568
Gln Ala Val Gly Ile Cys Gln Val Leu Leu Asp Glu Gly Ala Leu Cys
    110                 115                 120 cat gta aaa cat gac tgg acc ttc cag gac cga gac gcc caa ttc tac    616
His Val Lys His Asp Trp Thr Phe Gln Asp Arg Asp Ala Gln Phe Tyr
125                 130                 135                 140 aga ttc cct gga ccg gag ccc cag cct gca gga act cat gac gtg gaa    664
Arg Phe Pro Gly Pro Glu Pro Gln Pro Ala Gly Thr His Asp Val Glu
                145                 150                 155 gag gag ctt gtt gag gca atg gcc cta ctc tcc cag cga ggg cct gat    712
Glu Glu Leu Val Glu Ala Met Ala Leu Leu Ser Gln Arg Gly Pro Asp
            160                 165                 170
```

-continued

```
gcc cta ctc act gtt gca ctc cgg aag tcc ccg ggt cag cgt aca gat        760
Ala Leu Leu Thr Val Ala Leu Arg Lys Ser Pro Gly Gln Arg Thr Asp
        175                 180                 185 gaa gag ctg gac ctc atc ttc gag gag ctc gta cat atc aag gcg gtg        808
Glu Glu Leu Asp Leu Ile Phe Glu Glu Leu Val His Ile Lys Ala Val
190                 195                 200 gct cac ctt tct aac tcg gtg aaa cgg gaa cta gct gct gtt ctg ctc        856
Ala His Leu Ser Asn Ser Val Lys Arg Glu Leu Ala Ala Val Leu Leu
205                 210                 215                 220 ttt gaa cca cac agc aag gca gga act gtg ttg ttc agc cag ggg gac        904
Phe Glu Pro His Ser Lys Ala Gly Thr Val Leu Phe Ser Gln Gly Asp
                225                 230                 235 aag ggt acc tca tgg tac att atc tgg aag gga tct gtc aat gtg gtg        952
Lys Gly Thr Ser Trp Tyr Ile Ile Trp Lys Gly Ser Val Asn Val Val
            240                 245                 250 acc cgt ggc aag ggg ctg gtg acc acg ttg cac gag gga gat gac ttt       1000
Thr Arg Gly Lys Gly Leu Val Thr Thr Leu His Glu Gly Asp Asp Phe
        255                 260                 265 gga cag ctg gct ctg gtg aac gac gca cct cga gca gcc acc atc atc       1048
Gly Gln Leu Ala Leu Val Asn Asp Ala Pro Arg Ala Ala Thr Ile Ile
270                 275                 280 ctt cga gaa aat aac tgt cac ttt ctg cgt gtg gac aag cag gac ttc       1096
Leu Arg Glu Asn Asn Cys His Phe Leu Arg Val Asp Lys Gln Asp Phe
285                 290                 295                 300 aac cgc atc atc aag gat gtg gaa gca aaa acc atg aga ctg gaa gaa       1144
Asn Arg Ile Ile Lys Asp Val Glu Ala Lys Thr Met Arg Leu Glu Glu
                305                 310                 315 cac ggc aaa gtg gtg tta gtt ttg gag aga acc tct cag ggt gct ggc       1192
His Gly Lys Val Val Leu Val Leu Glu Arg Thr Ser Gln Gly Ala Gly
            320                 325                 330 cct tcc cgc cct ccg acc cca ggc agg aac cga tat acg gta atg tct       1240
Pro Ser Arg Pro Pro Thr Pro Gly Arg Asn Arg Tyr Thr Val Met Ser
        335                 340                 345 ggc acc cca gag aaa atc cta gaa ctc ctg ttg gag gct atg aga ccg       1288
Gly Thr Pro Glu Lys Ile Leu Glu Leu Leu Leu Glu Ala Met Arg Pro
350                 355                 360 gat tcc agt gct cat gac cca aca gag aca ttc ctc agt gac ttc ctg       1336
Asp Ser Ser Ala His Asp Pro Thr Glu Thr Phe Leu Ser Asp Phe Leu
365                 370                 375                 380 ctg acg cac agt gtc ttc atg ccc tgc aca cag ctc ttt gcc gcc ctc       1384
Leu Thr His Ser Val Phe Met Pro Cys Thr Gln Leu Phe Ala Ala Leu
                385                 390                 395 ctg cac cac ttc cac gtg gag cca tca gag cct gcc ggg ggc agc gag       1432
Leu His His Phe His Val Glu Pro Ser Glu Pro Ala Gly Gly Ser Glu
            400                 405                 410 cag gaa cgc agc acc tac atc tgc aac aag agg cag cag att ctg cgt       1480
Gln Glu Arg Ser Thr Tyr Ile Cys Asn Lys Arg Gln Gln Ile Leu Arg
        415                 420                 425 ctg gtc agc cgg tgg gtg gcc ctc tac agc ccc atg ctc cgc tca gat       1528
Leu Val Ser Arg Trp Val Ala Leu Tyr Ser Pro Met Leu Arg Ser Asp
430                 435                 440 ccc gtg gcc acc agc ttc ctc cag aaa ctc tca gac ctg gtg agc aga       1576
Pro Val Ala Thr Ser Phe Leu Gln Lys Leu Ser Asp Leu Val Ser Arg
445                 450                 455                 460 gat acc cga ctt agc aac ttg ctg agg gaa cag tat ccg gag aga cgg       1624
Asp Thr Arg Leu Ser Asn Leu Leu Arg Glu Gln Tyr Pro Glu Arg Arg
                465                 470                 475 cga cac cac agg ttg gag aat ggc tgt ggg aat gta tct cct cag acc       1672
Arg His His Arg Leu Glu Asn Gly Cys Gly Asn Val Ser Pro Gln Thr
```

-continued

```
                480                 485                 490
aag gcc cgg aat gca cct gtt tgg ttt cct aac cat gag gaa ccc ctc      1720
Lys Ala Arg Asn Ala Pro Val Trp Phe Pro Asn His Glu Glu Pro Leu
        495                 500                 505 cca agc agc gct ggg gcc atc cga gtc ggg gac aaa gtc ccc tat gat      1768
Pro Ser Ser Ala Gly Ala Ile Arg Val Gly Asp Lys Val Pro Tyr Asp
510                 515                 520 atc tgc aga ccc gac cac tcg gtg ctg acc ctg cac ctg ccg gtg aca      1816
Ile Cys Arg Pro Asp His Ser Val Leu Thr Leu His Leu Pro Val Thr
525                 530                 535                 540 gcc tcc gtg agg gaa gtg atg gca gct ttg gcc cat gag gac cac tgg      1864
Ala Ser Val Arg Glu Val Met Ala Ala Leu Ala His Glu Asp His Trp
                545                 550                 555 acc aag ggg cag gtg ctg gta aag gtc aat tct gcc ggt gat gtc gtt      1912
Thr Lys Gly Gln Val Leu Val Lys Val Asn Ser Ala Gly Asp Val Val
        560                 565                 570 ggc ttg cag cca gat gcc cgc ggt gtg gcc aca tcc ctg ggg ctc aat      1960
Gly Leu Gln Pro Asp Ala Arg Gly Val Ala Thr Ser Leu Gly Leu Asn
575                 580                 585 gag cgg atc ttt gtt gtc gac cca cag gaa gtg cac gag ctg acc cca      2008
Glu Arg Ile Phe Val Val Asp Pro Gln Glu Val His Glu Leu Thr Pro
590                 595                 600 cac cct gag cag ctg ggg ccc act ctg ggt tct tct gag atg ctg gac      2056
His Pro Glu Gln Leu Gly Pro Thr Leu Gly Ser Ser Glu Met Leu Asp
605                 610                 615                 620 cta gtg agt gcc aag gac ctg gca ggc cag ctc aca gag cat gac tgg      2104
Leu Val Ser Ala Lys Asp Leu Ala Gly Gln Leu Thr Glu His Asp Trp
                625                 630                 635 aac ctc ttc aac agg atc cac cag gtg gag ctg atc cac tat gta ctg      2152
Asn Leu Phe Asn Arg Ile His Gln Val Glu Leu Ile His Tyr Val Leu
        640                 645                 650 ggc ccc cag cac ctg cgg gac gtc acc act gca aac ctg gag cgc ttc      2200
Gly Pro Gln His Leu Arg Asp Val Thr Thr Ala Asn Leu Glu Arg Phe
655                 660                 665 atg cga cgc ttc aac gag ctg cag tac tgg gtg gcc acc gaa ctc tgt      2248
Met Arg Arg Phe Asn Glu Leu Gln Tyr Trp Val Ala Thr Glu Leu Cys
670                 675                 680 ctc tgc ccg gtt cct ggc ccc cgg gct cag cta ctc cgg aag ttc atc      2296
Leu Cys Pro Val Pro Gly Pro Arg Ala Gln Leu Leu Arg Lys Phe Ile
685                 690                 695                 700 aag ctg gca gcc cac ctc aag gag cag aag aat ctc aac tct ttc ttt      2344
Lys Leu Ala Ala His Leu Lys Glu Gln Lys Asn Leu Asn Ser Phe Phe
                705                 710                 715 gcg gtc atg ttt ggc ctc agc aac tcg gcc atc agc cgc ctg gcc cac      2392
Ala Val Met Phe Gly Leu Ser Asn Ser Ala Ile Ser Arg Leu Ala His
        720                 725                 730 acc tgg gag cgt ctg ccc cat aaa gta cgg aag ctg tac tcg gcc ctg      2440
Thr Trp Glu Arg Leu Pro His Lys Val Arg Lys Leu Tyr Ser Ala Leu
735                 740                 745 gaa agg ttg ctg gac cct tcc tgg aac cac cga gtg tac cga ttg gct      2488
Glu Arg Leu Leu Asp Pro Ser Trp Asn His Arg Val Tyr Arg Leu Ala
750                 755                 760 ctc acc aag ctc tct cct cct gtc atc cct ttc atg ccc ctg cta ctc      2536
Leu Thr Lys Leu Ser Pro Pro Val Ile Pro Phe Met Pro Leu Leu Leu
765                 770                 775                 780 aaa gac atg acc ttc att cat gaa ggg aac cac aca ctg gta gaa aac      2584
Lys Asp Met Thr Phe Ile His Glu Gly Asn His Thr Leu Val Glu Asn
                785                 790                 795 ctc atc aac ttt gag aag atg cga atg atg gcc aga gcc gtg cgg atg      2632
Leu Ile Asn Phe Glu Lys Met Arg Met Met Ala Arg Ala Val Arg Met
```

-continued

```
Leu Ile Asn Phe Glu Lys Met Arg Met Met Ala Arg Ala Val Arg Met
                800                 805                 810 ctc cac cac tgc cga agc cac agc acc gcg cct cta tca cca ctc aga    2680
Leu His His Cys Arg Ser His Ser Thr Ala Pro Leu Ser Pro Leu Arg
            815                 820                 825 agc cgg gtt tcc cac atc cac gag gac agc cag gca tca aga atc tcc    2728
Ser Arg Val Ser His Ile His Glu Asp Ser Gln Ala Ser Arg Ile Ser
        830                 835                 840 aca tgt tcc gag cag tcc ctg agc acc cgg agt cca gcc agc acc tgg    2776
Thr Cys Ser Glu Gln Ser Leu Ser Thr Arg Ser Pro Ala Ser Thr Trp
845                 850                 855                 860 gct tat gtc cag cag ctg aag gtc att gac aac cag cgg gaa ctg tcc    2824
Ala Tyr Val Gln Gln Leu Lys Val Ile Asp Asn Gln Arg Glu Leu Ser
                865                 870                 875 cgc ctc tcc cgg gaa ctg gaa cca tgaggaagga ctggctggag caggcacttc   2878
Arg Leu Ser Arg Glu Leu Glu Pro
                880 tctcagagaa agccagagcc tgtgcaacca agaggtccag aggccagcca cagctgggca  2938 gggctctcca cagagcggac tcaaggccct ggagtgggca gtgtcgaggc agctgtcctc  2998 tgtgatgact gtcagctgtg aagatctttg atgttcacgg ccaaggaaaa ggggccattg  3058 aggccccaga gggtaggag agctgggagg tgcaggactc tggttcagta gagagccctc   3118 ccaccgggct ttctgcatgt ctgtatgtct gtacatgcag ctgtgtgtcc tggatgccag  3178 gccctgtgct tgtattcaca ggagccagcg agctcacatc tgcatggtgt gtgtgtgtgt  3238 gtgtgtgtgt gtgtgtgtgt gtgtgtgtga cactgggtg gtgccttgcc tgggagaggg   3298 tggggagttc tgctattctc accacacatc tgagataaac agctgggtgt gggcaaaaaa  3358 aaaaaaaaaa aaaaa                                                   3373
```

<210> SEQ ID NO 10
<211> LENGTH: 884
<212> TYPE: PRT
<213> ORGANISM: Rattus norvegicus

<400> SEQUENCE: 10

```
Met Val Leu Lys Arg Met His Arg Pro Arg Cys Cys Ser Tyr Gln Leu
1               5                   10                  15

Val Phe Glu His Arg Arg Pro Ser Cys Ile Gln Gly Leu Arg Trp Thr
            20                  25                  30

Pro Leu Thr Asn Ser Glu Gly Ser Leu Asp Phe Arg Val Ser Leu Glu
        35                  40                  45

Gln Ala Thr Thr Glu His Val His Lys Ala Gly Lys Leu Leu Tyr Arg
    50                  55                  60

His Leu Leu Ala Thr Tyr Pro Thr Leu Ile Arg Asp Arg Lys Tyr His
65                  70                  75                  80

Leu Arg Leu His Arg Gln Cys Cys Ser Gly Arg Glu Leu Val Asp Gly
                85                  90                  95

Ile Leu Ala Leu Gly Leu Gly Val His Ser Arg Ser Gln Ala Val Gly
            100                 105                 110

Ile Cys Gln Val Leu Leu Asp Glu Gly Ala Leu Cys His Val Lys His
        115                 120                 125

Asp Trp Thr Phe Gln Asp Arg Asp Ala Gln Phe Tyr Arg Phe Pro Gly
    130                 135                 140

Pro Glu Pro Gln Pro Ala Gly Thr His Asp Val Glu Glu Glu Leu Val
145                 150                 155                 160
```

-continued

```
Glu Ala Met Ala Leu Leu Ser Gln Arg Gly Pro Asp Ala Leu Leu Thr
            165                 170                 175

Val Ala Leu Arg Lys Ser Pro Gly Gln Arg Thr Asp Glu Glu Leu Asp
        180                 185                 190

Leu Ile Phe Glu Glu Leu Val His Ile Lys Ala Val Ala His Leu Ser
    195                 200                 205

Asn Ser Val Lys Arg Glu Leu Ala Ala Val Leu Leu Phe Glu Pro His
210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Val Thr Arg Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Asn
        275                 280                 285

Asn Cys His Phe Leu Arg Val Asp Lys Gln Asp Phe Asn Arg Ile Ile
    290                 295                 300

Lys Asp Val Glu Ala Lys Thr Met Arg Leu Glu His Gly Lys Val
305                 310                 315                 320

Val Leu Val Leu Glu Arg Thr Ser Gln Gly Ala Gly Pro Ser Arg Pro
                325                 330                 335

Pro Thr Pro Gly Arg Asn Arg Tyr Thr Val Met Ser Gly Thr Pro Glu
            340                 345                 350

Lys Ile Leu Glu Leu Leu Glu Ala Met Arg Pro Asp Ser Ser Ala
        355                 360                 365

His Asp Pro Thr Glu Thr Phe Leu Ser Asp Phe Leu Thr His Ser
    370                 375                 380

Val Phe Met Pro Cys Thr Gln Leu Phe Ala Ala Leu His His Phe
385                 390                 395                 400

His Val Glu Pro Ser Glu Pro Ala Gly Gly Ser Gln Glu Arg Ser
                405                 410                 415

Thr Tyr Ile Cys Asn Lys Arg Gln Gln Ile Leu Arg Leu Val Ser Arg
            420                 425                 430

Trp Val Ala Leu Tyr Ser Pro Met Leu Arg Ser Asp Pro Val Ala Thr
        435                 440                 445

Ser Phe Leu Gln Lys Leu Ser Asp Leu Val Ser Arg Asp Thr Arg Leu
    450                 455                 460

Ser Asn Leu Leu Arg Glu Gln Tyr Pro Glu Arg Arg His His Arg
465                 470                 475                 480

Leu Glu Asn Gly Cys Gly Asn Val Ser Pro Gln Thr Lys Ala Arg Asn
                485                 490                 495

Ala Pro Val Trp Phe Pro Asn His Glu Glu Pro Leu Pro Ser Ser Ala
            500                 505                 510

Gly Ala Ile Arg Val Gly Asp Lys Val Pro Tyr Asp Ile Cys Arg Pro
        515                 520                 525

Asp His Ser Val Leu Thr Leu His Leu Pro Val Thr Ala Ser Val Arg
    530                 535                 540

Glu Val Met Ala Ala Leu Ala His Glu Asp His Trp Thr Lys Gly Gln
545                 550                 555                 560

Val Leu Val Lys Val Asn Ser Ala Gly Asp Val Val Gly Leu Gln Pro
                565                 570                 575

Asp Ala Arg Gly Val Ala Thr Ser Leu Gly Leu Asn Glu Arg Ile Phe
```

```
                  580                 585                 590
Val Val Asp Pro Gln Glu Val His Glu Leu Thr Pro His Pro Glu Gln
            595                 600                 605

Leu Gly Pro Thr Leu Gly Ser Ser Glu Met Leu Asp Leu Val Ser Ala
        610                 615                 620

Lys Asp Leu Ala Gly Gln Leu Thr Glu His Asp Trp Asn Leu Phe Asn
625                 630                 635                 640

Arg Ile His Gln Val Glu Leu Ile His Tyr Val Leu Gly Pro Gln His
                645                 650                 655

Leu Arg Asp Val Thr Thr Ala Asn Leu Glu Arg Phe Met Arg Arg Phe
            660                 665                 670

Asn Glu Leu Gln Tyr Trp Val Ala Thr Glu Leu Cys Leu Cys Pro Val
        675                 680                 685

Pro Gly Pro Arg Ala Gln Leu Leu Arg Lys Phe Ile Lys Leu Ala Ala
        690                 695                 700

His Leu Lys Glu Gln Lys Asn Leu Asn Ser Phe Phe Ala Val Met Phe
705                 710                 715                 720

Gly Leu Ser Asn Ser Ala Ile Ser Arg Leu Ala His Thr Trp Glu Arg
                725                 730                 735

Leu Pro His Lys Val Arg Lys Leu Tyr Ser Ala Leu Glu Arg Leu Leu
            740                 745                 750

Asp Pro Ser Trp Asn His Arg Val Tyr Arg Leu Ala Leu Thr Lys Leu
        755                 760                 765

Ser Pro Pro Val Ile Pro Phe Met Pro Leu Leu Leu Lys Asp Met Thr
        770                 775                 780

Phe Ile His Glu Gly Asn His Thr Leu Val Glu Asn Leu Ile Asn Phe
785                 790                 795                 800

Glu Lys Met Arg Met Met Ala Arg Ala Val Arg Met Leu His His Cys
                805                 810                 815

Arg Ser His Ser Thr Ala Pro Leu Ser Pro Leu Arg Ser Arg Val Ser
            820                 825                 830

His Ile His Glu Asp Ser Gln Ala Ser Arg Ile Ser Thr Cys Ser Glu
        835                 840                 845

Gln Ser Leu Ser Thr Arg Ser Pro Ala Ser Thr Trp Ala Tyr Val Gln
        850                 855                 860

Gln Leu Lys Val Ile Asp Asn Gln Arg Glu Leu Ser Arg Leu Ser Arg
865                 870                 875                 880

Glu Leu Glu Pro

<210> SEQ ID NO 11
<211> LENGTH: 3394
<212> TYPE: DNA
<213> ORGANISM: Homo sapiens
<220> FEATURE:
<221> NAME/KEY: CDS
<222> LOCATION: (216)..(2858)

<400> SEQUENCE: 11
ggatcccctt atcaaagctg atgggggtcg ctggggaccc cccagccttt tgctagagcc      60
tgcacggctg tgggagcttg aaaagaaaca tgaaggtggg ctggccaggt gagagctgct     120
ggcaggtggg cctggctgtg gaggatagcc cagctctggg agcaccgcgg gtgggagccc     180
tccctgacgt ggtgccggag gggacactac tcaac atg gtg ttg aga agg atg       233
                                      Met Val Leu Arg Arg Met
                                        1               5
```

-continued

| | | |
|---|---|---|
| cac cgg ccc cga agc tgc tcc tac cag ctg ctg ctg gag cac cag cat<br>His Arg Pro Arg Ser Cys Ser Tyr Gln Leu Leu Leu Glu His Gln His<br>          10                   15                20 | 281 |
| ccg agc tgc atc cag ggg ctg cgc tgg aca cca ctc acc aac agc gag<br>Pro Ser Cys Ile Gln Gly Leu Arg Trp Thr Pro Leu Thr Asn Ser Glu<br>        25                   30                 35 | 329 |
| gag tcc ctg gat ttc agc gag agc ctg gag cag gcc tcc aca gag cgg<br>Glu Ser Leu Asp Phe Ser Glu Ser Leu Glu Gln Ala Ser Thr Glu Arg<br>40                     45                 50 | 377 |
| gtg ctc agg gct ggg agg cag ctg cat cag cat cta ctg gcc acc tgc<br>Val Leu Arg Ala Gly Arg Gln Leu His Gln His Leu Leu Ala Thr Cys<br>55                  60                65                70 | 425 |
| cca aac ctc atc cga gac cgg aag tac cac ctt agg ctc tat cgg cag<br>Pro Asn Leu Ile Arg Asp Arg Lys Tyr His Leu Arg Leu Tyr Arg Gln<br>               75                80                85 | 473 |
| tgc tgc tct ggc cgg gag ctg gtg gat ggg atc ttg gcc ctg gga ctt<br>Cys Cys Ser Gly Arg Glu Leu Val Asp Gly Ile Leu Ala Leu Gly Leu<br>          90                   95                100 | 521 |
| ggg gtc cat tcc cgg agc caa gtt gtg gga atc tgc cag gtg ctg ctg<br>Gly Val His Ser Arg Ser Gln Val Val Gly Ile Cys Gln Val Leu Leu<br>105                 110                115 | 569 |
| gat gaa ggt gcc ctc tgc cat gtg aaa cac gac tgg gcc ttc cag gac<br>Asp Glu Gly Ala Leu Cys His Val Lys His Asp Trp Ala Phe Gln Asp<br>120                 125                130 | 617 |
| cga gat gcc caa ttc tac cgg ttc ccc ggg ccc gag ccc gag ccc gtg<br>Arg Asp Ala Gln Phe Tyr Arg Phe Pro Gly Pro Glu Pro Glu Pro Val<br>135                 140                145                150 | 665 |
| gga act cat gag atg gag gag gag ttg gcc gaa gct gtg gcc ctg ctc<br>Gly Thr His Glu Met Glu Glu Glu Leu Ala Glu Ala Val Ala Leu Leu<br>                     155                160                165 | 713 |
| tcc cag cgg ggg cct gac gcc ctg ctc act gtg gca ctt cga aag ccc<br>Ser Gln Arg Gly Pro Asp Ala Leu Leu Thr Val Ala Leu Arg Lys Pro<br>170                 175                180 | 761 |
| cca ggt cag cgc acg gat gaa gag ctg gac ctc atc ttt gag gag ctg<br>Pro Gly Gln Arg Thr Asp Glu Glu Leu Asp Leu Ile Phe Glu Glu Leu<br>185                 190                195 | 809 |
| ctg cac atc aag gct gtg gcc cac ctc tcc aac tcg gtg aag cga gaa<br>Leu His Ile Lys Ala Val Ala His Leu Ser Asn Ser Val Lys Arg Glu<br>200                 205                210 | 857 |
| tta gcg gct gtt ctg ctc ttt gaa cca cac agc aag gca ggg acc gtg<br>Leu Ala Ala Val Leu Leu Phe Glu Pro His Ser Lys Ala Gly Thr Val<br>215                 220                225                230 | 905 |
| ttg ttc agc cag ggg gac aag ggc act tcg tgg tac att atc tgg aag<br>Leu Phe Ser Gln Gly Asp Lys Gly Thr Ser Trp Tyr Ile Ile Trp Lys<br>                     235                240                245 | 953 |
| gga tct gtc aac gtg gtg acc cat ggc aag ggg ctg gtg acc acc ctg<br>Gly Ser Val Asn Val Val Thr His Gly Lys Gly Leu Val Thr Thr Leu<br>250                 255                260 | 1001 |
| cat gag gga gat gat ttt gga cag ctg gct ctg gtg aat gat gca ccc<br>His Glu Gly Asp Asp Phe Gly Gln Leu Ala Leu Val Asn Asp Ala Pro<br>265                 270                275 | 1049 |
| cgg gca gcc acc atc atc ctg cga gaa tac aac tgt cat ttc ctg cgt<br>Arg Ala Ala Thr Ile Ile Leu Arg Glu Tyr Asn Cys His Phe Leu Arg<br>280                 285                290 | 1097 |
| gtg gac aag cag gac ttc aac cgt atc atc aag gat gtg gag gca aag<br>Val Asp Lys Gln Asp Phe Asn Arg Ile Ile Lys Asp Val Glu Ala Lys<br>295                 300                305                310 | 1145 |
| acc atg cgg ctg gaa gaa cat ggc aaa gtg gtg ctg gtg ctg gag aga<br>Thr Met Arg Leu Glu Glu His Gly Lys Val Val Leu Val Leu Glu Arg<br>                     315                320                325 | 1193 |

-continued

| | |
|---|---|
| gcc tct cag ggc gcc ggc cct tcc cga ccc cca acc cca ggc agg aac<br>Ala Ser Gln Gly Ala Gly Pro Ser Arg Pro Pro Thr Pro Gly Arg Asn<br>330     335     340 | 1241 |
| cgg tat aca gtg atg tct ggc act cca gat aag atc cta gag ctt ctg<br>Arg Tyr Thr Val Met Ser Gly Thr Pro Asp Lys Ile Leu Glu Leu Leu<br>   345     350     355 | 1289 |
| ttg gag gcc atg gga cta gat tcc agt gct cat gac cca aaa gaa aca<br>Leu Glu Ala Met Gly Leu Asp Ser Ser Ala His Asp Pro Lys Glu Thr<br>360     365     370 | 1337 |
| ttc ctc agc gac ttc ctc ctg acc cac agg gtc ttc atg ccc agc gcc<br>Phe Leu Ser Asp Phe Leu Leu Thr His Arg Val Phe Met Pro Ser Ala<br>375     380     385     390 | 1385 |
| caa ctc tgc gct gcc ctt ctg cac cac ttc cat gtg gag cct gcg ggt<br>Gln Leu Cys Ala Ala Leu Leu His His Phe His Val Glu Pro Ala Gly<br>   395     400     405 | 1433 |
| ggc agc gag cag gag cgc agc acc tac gtc tgc aac aag agg cag cag<br>Gly Ser Glu Gln Glu Arg Ser Thr Tyr Val Cys Asn Lys Arg Gln Gln<br>410     415     420 | 1481 |
| atc ttg cgg ctg gtc agc cag tgg gtg gcc ctg tat ggc tcc atg ctc<br>Ile Leu Arg Leu Val Ser Gln Trp Val Ala Leu Tyr Gly Ser Met Leu<br>425     430     435 | 1529 |
| cac act gac cct gtg gcc acc agc ttc ctc cac aaa ctc tca gac ctg<br>His Thr Asp Pro Val Ala Thr Ser Phe Leu His Lys Leu Ser Asp Leu<br>440     445     450 | 1577 |
| gtg ggc agg gac acc cga ctc agc aac ctg ctg agg gag cag tgg cca<br>Val Gly Arg Asp Thr Arg Leu Ser Asn Leu Leu Arg Glu Gln Trp Pro<br>455     460     465     470 | 1625 |
| gag agg cgg cga tgc cac agg ttg gag aat ggc tgt ggg aat gca tct<br>Glu Arg Arg Arg Cys His Arg Leu Glu Asn Gly Cys Gly Asn Ala Ser<br>   475     480     485 | 1673 |
| cct cag atg aag gcc cgg aac ttg cct gtt tgg ctc ccc aac cag gac<br>Pro Gln Met Lys Ala Arg Asn Leu Pro Val Trp Leu Pro Asn Gln Asp<br>490     495     500 | 1721 |
| gag ccc ctt cct ggc agc agc tgt gcc atc caa gtt ggg gat aaa gtc<br>Glu Pro Leu Pro Gly Ser Ser Cys Ala Ile Gln Val Gly Asp Lys Val<br>505     510     515 | 1769 |
| ccc tat gac atc tgc cgg cca gac cac tca gtg ttg acc ctg cag ctg<br>Pro Tyr Asp Ile Cys Arg Pro Asp His Ser Val Leu Thr Leu Gln Leu<br>520     525     530 | 1817 |
| cct gtg aca gcc tcc gtg aga gag gtg atg gca gcg ttg gcc cag gag<br>Pro Val Thr Ala Ser Val Arg Glu Val Met Ala Ala Leu Ala Gln Glu<br>535     540     545     550 | 1865 |
| gat ggc tgg acc aag ggg cag gtg ctg gtg aag gtc aat tct gca ggt<br>Asp Gly Trp Thr Lys Gly Gln Val Leu Val Lys Val Asn Ser Ala Gly<br>   555     560     565 | 1913 |
| gat gcc att ggc ctg cag cca gat gcc cgt ggt gtg gcc aca tct ctg<br>Asp Ala Ile Gly Leu Gln Pro Asp Ala Arg Gly Val Ala Thr Ser Leu<br>570     575     580 | 1961 |
| ggg ctc aat gag cgt ctc ttt gtt gtc aac cca cag gaa gtg cat gag<br>Gly Leu Asn Glu Arg Leu Phe Val Val Asn Pro Gln Glu Val His Glu<br>585     590     595 | 2009 |
| ctg atc cca cac cct gac cag ctg ggg ccc act gtg ggc tct gct gag<br>Leu Ile Pro His Pro Asp Gln Leu Gly Pro Thr Val Gly Ser Ala Glu<br>600     605     610 | 2057 |
| ggg ctg gac ctg gtg agt gcc aag gac ctg gca ggc cag ctg acg gac<br>Gly Leu Asp Leu Val Ser Ala Lys Asp Leu Ala Gly Gln Leu Thr Asp<br>615     620     625     630 | 2105 |
| cac gac tgg agc ctc ttc aac agt atc cac cag gtg gag ctg atc cac<br>His Asp Trp Ser Leu Phe Asn Ser Ile His Gln Val Glu Leu Ile His | 2153 |

```
                    635              640             645
tat gtg ctg ggc ccc cag cat ctg cgg gat gtc acc acc gcc aac ctg    2201
Tyr Val Leu Gly Pro Gln His Leu Arg Asp Val Thr Thr Ala Asn Leu
            650                 655                 660 gag cgc ttc atg cgc cgc ttc aat gag ctg cag tac tgg gtg gcc acc    2249
Glu Arg Phe Met Arg Arg Phe Asn Glu Leu Gln Tyr Trp Val Ala Thr
            665                 670                 675 gag ctg tgt ctc tgc ccc gtg ccc ggc ccc cgg gcc cag ctg ctc aaa    2297
Glu Leu Cys Leu Cys Pro Val Pro Gly Pro Arg Ala Gln Leu Leu Lys
            680                 685                 690 aag ttc att aag ctg gcg gcc cac ctc aag gag cag aag aat gtc aat    2345
Lys Phe Ile Lys Leu Ala Ala His Leu Lys Glu Gln Lys Asn Val Asn
695                 700                 705                 710 tcc ttc ttt gcc gtc atg ttt ggc ctc agc aac tcg ccc atc agc cgc    2393
Ser Phe Phe Ala Val Met Phe Gly Leu Ser Asn Ser Pro Ile Ser Arg
                715                 720                 725 cta gcc cac acc tgg gag cgg ctg cct cac aaa gtc cgg aag ctg tac    2441
Leu Ala His Thr Trp Glu Arg Leu Pro His Lys Val Arg Lys Leu Tyr
            730                 735                 740 tcc gcc ctc gag agg ctg ctg gat ccc tca tgg aac cac cgg gta tac    2489
Ser Ala Leu Glu Arg Leu Leu Asp Pro Ser Trp Asn His Arg Val Tyr
            745                 750                 755 cga ctg gcc ctc gcc aag ctc tcc cct cct gtc atc ccc ttc atg ccc    2537
Arg Leu Ala Leu Ala Lys Leu Ser Pro Pro Val Ile Pro Phe Met Pro
            760                 765                 770 ctt ctt ctc aaa gac atg acc ttc att cat gag gga aac cac aca cta    2585
Leu Leu Leu Lys Asp Met Thr Phe Ile His Glu Gly Asn His Thr Leu
775                 780                 785                 790 gtg gag aat ctc atc aac ttt gag aag atg aga atg atg gcc aga gcc    2633
Val Glu Asn Leu Ile Asn Phe Glu Lys Met Arg Met Met Ala Arg Ala
                795                 800                 805 gcg cgg atg ctg cac cac tgc cga agc cac aac cct gtg cct ctc tca    2681
Ala Arg Met Leu His His Cys Arg Ser His Asn Pro Val Pro Leu Ser
            810                 815                 820 cca ctc aga agc cga gtt tcc cac ctc cac gag gac agc cag gtg gcg    2729
Pro Leu Arg Ser Arg Val Ser His Leu His Glu Asp Ser Gln Val Ala
            825                 830                 835 agg att tcc aca tgc tcg gag cag tcc ctg agc acc cgg agt cca gcc    2777
Arg Ile Ser Thr Cys Ser Glu Gln Ser Leu Ser Thr Arg Ser Pro Ala
840                 845                 850 agc acc tgg gct tat gtc cag cag ctg aag gtc att gac aac cag cgg    2825
Ser Thr Trp Ala Tyr Val Gln Gln Leu Lys Val Ile Asp Asn Gln Arg
855                 860                 865                 870 gaa ctc tcc cgc ctg tcc cga gag ctg gag cca tgaggagggg ctgggactgg  2878
Glu Leu Ser Arg Leu Ser Arg Glu Leu Glu Pro
                875                 880 agctggagca ggcacttgca gccgggaaag ccagggtgtg ccgggccaag atactcacag  2938
gctggccaca gctgggcaag gctctccgtg gagtggactc gagtccctgg agcaggcagt  2998
gtggaggcag ccatcccctg tgatgactgg cagctaagga ggacctcgga gtggaccaaa  3058
gccaggaata acgaatgacc aagggccaag gaagggagga cagagaggcc ccaggagtgg  3118
gtggagagtg gagtgcgctg ggacgttgtg tgcaatagag aggtctccac accagatgtc  3178
ttccagattc tgtgcctctg gctttgttgt ccagccaggc ctgcagttta ttttcacagt  3238
ggacagagag agagagagag gctgcatgtg tgtaccgtgt gtggcaaggg cagggccttg  3298
gcctggggca ggggcccctg ctttctttcc acagctttct tccaacagca ggcagtgggg  3358
ctgcgggcct gaaaaaaaaa aaaaaaaaaa aaaaaa                            3394
```

<210> SEQ ID NO 12
<211> LENGTH: 881
<212> TYPE: PRT
<213> ORGANISM: Homo sapiens

<400> SEQUENCE: 12

```
Met Val Leu Arg Arg Met His Arg Pro Arg Ser Cys Ser Tyr Gln Leu
1               5                   10                  15

Leu Leu Glu His Gln His Pro Ser Cys Ile Gln Gly Leu Arg Trp Thr
            20                  25                  30

Pro Leu Thr Asn Ser Glu Glu Ser Leu Asp Phe Ser Glu Ser Leu Glu
        35                  40                  45

Gln Ala Ser Thr Glu Arg Val Leu Arg Ala Gly Arg Gln Leu His Gln
    50                  55                  60

His Leu Leu Ala Thr Cys Pro Asn Leu Ile Arg Asp Arg Lys Tyr His
65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
    210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Val Thr His Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Tyr
        275                 280                 285

Asn Cys His Phe Leu Arg Val Asp Lys Gln Asp Phe Asn Arg Ile Ile
    290                 295                 300

Lys Asp Val Glu Ala Lys Thr Met Arg Leu Glu Glu His Gly Lys Val
305                 310                 315                 320

Val Leu Val Leu Glu Arg Ala Ser Gln Gly Ala Gly Pro Ser Arg Pro
                325                 330                 335

Pro Thr Pro Gly Arg Asn Arg Tyr Thr Val Met Ser Gly Thr Pro Asp
            340                 345                 350

Lys Ile Leu Glu Leu Leu Leu Glu Ala Met Gly Leu Asp Ser Ser Ala
        355                 360                 365

His Asp Pro Lys Glu Thr Phe Leu Ser Asp Phe Leu Leu Thr His Arg
```

```
                370             375             380
Val Phe Met Pro Ser Ala Gln Leu Cys Ala Ala Leu Leu His His Phe
385                 390             395                 400

His Val Glu Pro Ala Gly Gly Ser Gln Glu Arg Ser Thr Tyr Val
            405             410                 415

Cys Asn Lys Arg Gln Gln Ile Leu Arg Leu Val Ser Gln Trp Val Ala
            420             425             430

Leu Tyr Gly Ser Met Leu His Thr Asp Pro Val Ala Thr Ser Phe Leu
            435             440             445

His Lys Leu Ser Asp Leu Val Gly Arg Asp Thr Arg Leu Ser Asn Leu
450             455             460

Leu Arg Glu Gln Trp Pro Glu Arg Arg Cys His Arg Leu Glu Asn
465             470             475             480

Gly Cys Gly Asn Ala Ser Pro Gln Met Lys Ala Arg Asn Leu Pro Val
            485             490             495

Trp Leu Pro Asn Gln Asp Glu Pro Leu Pro Gly Ser Ser Cys Ala Ile
            500             505             510

Gln Val Gly Asp Lys Val Pro Tyr Asp Ile Cys Arg Pro Asp His Ser
            515             520             525

Val Leu Thr Leu Gln Leu Pro Val Thr Ala Ser Val Arg Glu Val Met
            530             535             540

Ala Ala Leu Ala Gln Glu Asp Gly Trp Thr Lys Gly Gln Val Leu Val
545             550             555             560

Lys Val Asn Ser Ala Gly Asp Ala Ile Gly Leu Gln Pro Asp Ala Arg
            565             570             575

Gly Val Ala Thr Ser Leu Gly Leu Asn Glu Arg Leu Phe Val Val Asn
            580             585             590

Pro Gln Glu Val His Glu Leu Ile Pro His Pro Asp Gln Leu Gly Pro
        595             600             605

Thr Val Gly Ser Ala Glu Gly Leu Asp Leu Val Ser Ala Lys Asp Leu
            610             615             620

Ala Gly Gln Leu Thr Asp His Asp Trp Ser Leu Phe Asn Ser Ile His
625             630             635             640

Gln Val Glu Leu Ile His Tyr Val Leu Gly Pro Gln His Leu Arg Asp
            645             650             655

Val Thr Thr Ala Asn Leu Glu Arg Phe Met Arg Arg Phe Asn Glu Leu
            660             665             670

Gln Tyr Trp Val Ala Thr Glu Leu Cys Leu Cys Pro Val Pro Gly Pro
            675             680             685

Arg Ala Gln Leu Leu Lys Lys Phe Ile Lys Leu Ala Ala His Leu Lys
690             695             700

Glu Gln Lys Asn Val Asn Ser Phe Phe Ala Val Met Phe Gly Leu Ser
705             710             715             720

Asn Ser Pro Ile Ser Arg Leu Ala His Thr Trp Glu Arg Leu Pro His
            725             730             735

Lys Val Arg Lys Leu Tyr Ser Ala Leu Glu Arg Leu Leu Asp Pro Ser
            740             745             750

Trp Asn His Arg Val Tyr Arg Leu Ala Leu Ala Lys Leu Ser Pro Pro
            755             760             765

Val Ile Pro Phe Met Pro Leu Leu Lys Asp Met Thr Phe Ile His
            770             775             780

Glu Gly Asn His Thr Leu Val Glu Asn Leu Ile Asn Phe Glu Lys Met
785             790             795             800
```

```
Arg Met Met Ala Arg Ala Ala Arg Met Leu His His Cys Arg Ser His
            805                 810                 815

Asn Pro Val Pro Leu Ser Pro Leu Arg Ser Arg Val Ser His Leu His
            820                 825                 830

Glu Asp Ser Gln Val Ala Arg Ile Ser Thr Cys Ser Glu Gln Ser Leu
            835                 840                 845

Ser Thr Arg Ser Pro Ala Ser Thr Trp Ala Tyr Val Gln Gln Leu Lys
        850                 855                 860

Val Ile Asp Asn Gln Arg Glu Leu Ser Arg Leu Ser Arg Glu Leu Glu
865                 870                 875                 880

Pro

<210> SEQ ID NO 13
<211> LENGTH: 4109
<212> TYPE: DNA
<213> ORGANISM: Homo sapiens
<220> FEATURE:
<221> NAME/KEY: CDS
<222> LOCATION: (216)..(1883)

<400> SEQUENCE: 13
```

| | |
|---|---:|
| ggatccccdtt atcaaagctg atgggggtcg ctggggaccc cccagccttt tgctagagcc | 60 |
| tgcacggctg tgggagcttg aaaagaaaca tgaaggtggg ctggccaggt gagagctgct | 120 |
| ggcaggtggg cctggctgtg gaggatagcc cagctctggg agcaccgcgg gtgggagccc | 180 |

```
tccctgacgt ggtgccggag gggacactac tcaac atg gtg ttg aga agg atg        233
                                      Met Val Leu Arg Arg Met
                                      1               5 cac cgg ccc cga agc tgc tcc tac cag ctg ctg ctg gag cac cag cat        281
His Arg Pro Arg Ser Cys Ser Tyr Gln Leu Leu Leu Glu His Gln His
            10                  15                  20 ccg agc tgc atc cag ggg ctg cgc tgg aca cca ctc acc aac agc gag        329
Pro Ser Cys Ile Gln Gly Leu Arg Trp Thr Pro Leu Thr Asn Ser Glu
        25                  30                  35 gag tcc ctg gat ttc agc gag agc ctg gag cag gcc tcc aca gag cgg        377
Glu Ser Leu Asp Phe Ser Glu Ser Leu Glu Gln Ala Ser Thr Glu Arg
    40                  45                  50 gtg ctc agg gct ggg agg cag ctg cat cag cat cta ctg gcc acc tgc        425
Val Leu Arg Ala Gly Arg Gln Leu His Gln His Leu Leu Ala Thr Cys
55                  60                  65                  70 cca aac ctc atc cga gac cgg aag tac cac ctt agg ctc tat cgg cag        473
Pro Asn Leu Ile Arg Asp Arg Lys Tyr His Leu Arg Leu Tyr Arg Gln
            75                  80                  85 tgc tgc tct ggc cgg gag ctg gtg gat ggg atc ttg gcc ctg gga ctt        521
Cys Cys Ser Gly Arg Glu Leu Val Asp Gly Ile Leu Ala Leu Gly Leu
        90                  95                  100 ggg gtc cat tcc cgg agc caa gtt gtg gga atc tgc cag gtg ctg ctg        569
Gly Val His Ser Arg Ser Gln Val Val Gly Ile Cys Gln Val Leu Leu
    105                 110                 115 gat gaa ggt gcc ctc tgc cat gtg aaa cac gac tgg gcc ttc cag gac        617
Asp Glu Gly Ala Leu Cys His Val Lys His Asp Trp Ala Phe Gln Asp
120                 125                 130 cga gat gcc caa ttc tac cgg ttc ccc ggg ccc gag ccc gag ccc gtg        665
Arg Asp Ala Gln Phe Tyr Arg Phe Pro Gly Pro Glu Pro Glu Pro Val
135                 140                 145                 150 gga act cat gag atg gag gag gag ttg gcc gaa gct gtg gcc ctg ctc        713
Gly Thr His Glu Met Glu Glu Glu Leu Ala Glu Ala Val Ala Leu Leu
            155                 160                 165
```

| | | |
|---|---|---|
| tcc cag cgg ggg cct gac gcc ctg ctc act gtg gca ctt cga aag ccc<br>Ser Gln Arg Gly Pro Asp Ala Leu Leu Thr Val Ala Leu Arg Lys Pro<br>170                        175                  180 | 761 |
| cca ggt cag cgc acg gat gaa gag ctg gac ctc atc ttt gag gag ctg<br>Pro Gly Gln Arg Thr Asp Glu Glu Leu Asp Leu Ile Phe Glu Glu Leu<br>                 185                     190                 195 | 809 |
| ctg cac atc aag gct gtg gcc cac ctc tcc aac tcg gtg aag cga gaa<br>Leu His Ile Lys Ala Val Ala His Leu Ser Asn Ser Val Lys Arg Glu<br>200                        205                  210 | 857 |
| tta gcg gct gtt ctg ctc ttt gaa cca cac agc aag gca ggg acc gtg<br>Leu Ala Ala Val Leu Leu Phe Glu Pro His Ser Lys Ala Gly Thr Val<br>215                  220                  225               230 | 905 |
| ttg ttc agc cag ggg gac aag ggc act tcg tgg tac att atc tgg aag<br>Leu Phe Ser Gln Gly Asp Lys Gly Thr Ser Trp Tyr Ile Ile Trp Lys<br>                 235                     240                 245 | 953 |
| gga tct gtc aac gtg gtg acc cat ggc aag ggg ctg gtg acc acc ctg<br>Gly Ser Val Asn Val Val Thr His Gly Lys Gly Leu Val Thr Thr Leu<br>250                        255                  260 | 1001 |
| cat gag gga gat gat ttt gga cag ctg gct ctg gtg aat gat gca ccc<br>His Glu Gly Asp Asp Phe Gly Gln Leu Ala Leu Val Asn Asp Ala Pro<br>265                  270                  275 | 1049 |
| cgg gca gcc acc atc atc ctg cga gaa tac aac tgt cat ttc ctg cgt<br>Arg Ala Ala Thr Ile Ile Leu Arg Glu Tyr Asn Cys His Phe Leu Arg<br>280                        285                  290 | 1097 |
| gtg gac aag cag gac ttc aac cgt atc atc aag gat gtg gag gca aag<br>Val Asp Lys Gln Asp Phe Asn Arg Ile Ile Lys Asp Val Glu Ala Lys<br>295                      300                  305               310 | 1145 |
| acc atg cgg ctg gaa gaa cat ggc aaa gtg gtg ctg gtg ctg gag aga<br>Thr Met Arg Leu Glu Glu His Gly Lys Val Val Leu Val Leu Glu Arg<br>                 315                     320                 325 | 1193 |
| gcc tct cag ggc gcc ggc cct tcc cga ccc cca acc cca ggc agg aac<br>Ala Ser Gln Gly Ala Gly Pro Ser Arg Pro Pro Thr Pro Gly Arg Asn<br>                 330                     335                 340 | 1241 |
| cgg tat aca gtg atg tct ggc act cca gat aag atc cta gag ctt ctg<br>Arg Tyr Thr Val Met Ser Gly Thr Pro Asp Lys Ile Leu Glu Leu Leu<br>345                        350                  355 | 1289 |
| ttg gag gcc atg gga cta gat tcc agt gct cat gac cca aaa gaa aca<br>Leu Glu Ala Met Gly Leu Asp Ser Ser Ala His Asp Pro Lys Glu Thr<br>360                        365                  370 | 1337 |
| ttc ctc agc gac ttc ctc ctg acc cac agg gtc ttc atg ccc agc gcc<br>Phe Leu Ser Asp Phe Leu Leu Thr His Arg Val Phe Met Pro Ser Ala<br>375                        380                  385               390 | 1385 |
| caa ctc tgc gct gcc ctt ctg cac cac ttc cat gtg gag cct gcg ggt<br>Gln Leu Cys Ala Ala Leu Leu His His Phe His Val Glu Pro Ala Gly<br>                 395                     400                 405 | 1433 |
| ggc agc gag cag gag cgc agc acc tac gtc tgc aac aag agg cag cag<br>Gly Ser Glu Gln Glu Arg Ser Thr Tyr Val Cys Asn Lys Arg Gln Gln<br>                 410                     415                 420 | 1481 |
| atc ttg cgg ctg gtc agc cag tgg gtg gcc ctg tat ggc tcc atg ctc<br>Ile Leu Arg Leu Val Ser Gln Trp Val Ala Leu Tyr Gly Ser Met Leu<br>                 425                     430                 435 | 1529 |
| cac act gac cct gtg gcc acc agc ttc ctc cag aaa ctc tca gac ctg<br>His Thr Asp Pro Val Ala Thr Ser Phe Leu Gln Lys Leu Ser Asp Leu<br>440                        445                  450 | 1577 |
| gtg ggc agg gac acc cga ctc agc aac ctg ctg agg gag cag tgg cca<br>Val Gly Arg Asp Thr Arg Leu Ser Asn Leu Leu Arg Glu Gln Trp Pro<br>455                        460                  465               470 | 1625 |
| gag agg cgg cga tgc cac agg ttg gag aat ggc tgt ggg aat gca tct<br>Glu Arg Arg Arg Cys His Arg Leu Glu Asn Gly Cys Gly Asn Ala Ser<br>                 475                     480                 485 | 1673 |

```
cct cag atg aag gtg tct gcc tgg ccc cag ttt ctt tcc tct gct cct    1721
Pro Gln Met Lys Val Ser Ala Trp Pro Gln Phe Leu Ser Ser Ala Pro
            490                 495                 500 cct gga ctg cag gca cct cct tcg ccc cct gac cct gag ggg ctc tgt    1769
Pro Gly Leu Gln Ala Pro Pro Ser Pro Pro Asp Pro Glu Gly Leu Cys
        505                 510                 515 ggg cgt ggg aag ctc tcc tcc cac aga cac acc ctt ggg tct ctg ata    1817
Gly Arg Gly Lys Leu Ser Ser His Arg His Thr Leu Gly Ser Leu Ile
520                 525                 530 ggt gtt cac ggg gcc ctt gct gca tgt ggt gcc ctg ggc cag gcc gtg    1865
Gly Val His Gly Ala Leu Ala Ala Cys Gly Ala Leu Gly Gln Ala Val
535                 540                 545                 550 cca gga ggc gca gag gcc taaggtggcc tccctcctcg cccactccct           1913
Pro Gly Gly Ala Glu Ala
                555 gactcaatgg gccttttatt ccttttggga ggtaattcat gcccacaggt agagcctggg  1973 agatgaggaa tggtggctgg agttggcccc tgaggcccac ggggctcctg gtggccagtg  2033 ctgtgggagc tcagaggaag gcgaggcccc tccctggaaa gtcagagggg ccccaggcc   2093 attctcagct ggggcttaaa gggaagcaaa gaggggatga aagatgtgaa ctgcagccag  2153 gatttggttg aggaatggtg ggagaaagaa ctggaaaggt agattaggtt ggtggtgggg  2213 agggctgcac tgggaataaa atccaggggc ctcaccatcc agcaggctcc ccatggtccc  2273 accctactgt gtgtcccagc ccctgcctgc tggagactct tactggcttc ttctcctccg  2333 caggcgaagc ccgttctccc ctcagggcct ttgcacttat cccttagcct ggaagggtct  2393 ttctctggct ctgcctggca ggatccttct cgttctcatc tcagccaaat gctgggttcc  2453 cagacaggcc cctcccgtt tccctatccg gagcaccctc ccctttctcc caccacgctc   2513 tgccttggtg tcctctgtga ttttttcaa agcactctcg ccatgtggag ttgttttctt   2573 tgcctacttg ctttctgtcc tttggtatct ctcccatccc actggagagt tgacttccct  2633 cctgcgggcc cccacctccg cttctccttg ctcacatgct gcctggctct tggctgacgc  2693 tcagaaactg atgtgggctc accctcgcag gctgggcact cgctaggtg ctgatgctgc   2753 acctcattca accctggcct gtggtggctg cagtcaggca aggggcagag cagttcaaca  2813 acccgtgatg tgcagtgaca cgggacactt tccctgaatg tgcactggag tcggctcttc  2873 caactgtagg tccgctgcct taaaccagga aggggaagag ccaactccag tgcagattca  2933 gggaaagtgt cccgtgtaag cgactactgg agttgagagc tgcaggggc aagggtggag   2993 gaagaagagg attcctggtg ggcaaaccca ggaggaaagg gaacccagga ggaggatccc  3053 tggaggagcg agagtaagag taggaccca gagcaggcag gaggtgggca gggcccctg    3113 ggcaaggaca ggggtctgat ctttgtccta agagcagtgc aaaccattaa agggtttga   3173 gccaaggttg gcaaagtctg atttgtgttt tgaataggtc agctaaagag cctgggcttt  3233 ctccagcaga caatggacac cactgaagtc gagtgcggga gcttcacagg gctctggtca  3293 ggcagattgg aggaggaggg ctggaggcac ctgggaggga ggaggaggag catagttggg  3353 ccattggagt agtaaggagt gaggcctcgt gggcaggtgg aactggagtt agcctgggca  3413 ggggaggagg gggcacagaa gacccacttc aaagaagaat cttcaaagca agatgacaag  3473 ctacggaagt gtgaggagc ctggagctgg ggagaatggc tggggaacag agtggtctgg   3533 gaggcaggat gcaaggatcc gatgggtata tggagtgtga ggtaatggtt cattcatgtg  3593 gaaggatgca gggggttttt gagaccaggg tttggaagag agttcagcac tgctggtagt  3653
```

-continued

```
tttgggaatc acccatgtgc aggcgacaca tgaggcagta aggaactctg caggggtccc    3713
tgagatttgg aaatgtaggg aagagcaatg gattgaggtc cgaacctgga ggatctgcta    3773
tacgcagagc tgggaggagg gacagagtca gtaccagagt cggaaaaaag cagggtggga    3833
aggggaacct gagtcaggag acttgcctgg caggcgctgc cctgccagca gaggcctgac    3893
agtggtttcc atgaactgca tccctgctgt gggctgggac agggccactg acacagtatc    3953
ggagcacaga aggggaaagg agcaggaggg attccaactc tgccagttag cagctgtgtg    4013
gctttgggca tgttacttaa cctctctgag cctcatttat ttcatccata aaatggaaat    4073
aaaaataata cttttgtcaa aaaaaaaaaa aaaaaa                              4109
```

<210> SEQ ID NO 14
<211> LENGTH: 556
<212> TYPE: PRT
<213> ORGANISM: Homo sapiens

<400> SEQUENCE: 14

```
Met Val Leu Arg Arg Met His Arg Pro Arg Ser Cys Ser Tyr Gln Leu
1               5                   10                  15

Leu Leu Glu His Gln His Pro Ser Cys Ile Gln Gly Leu Arg Trp Thr
            20                  25                  30

Pro Leu Thr Asn Ser Glu Glu Ser Leu Asp Phe Ser Glu Ser Leu Glu
        35                  40                  45

Gln Ala Ser Thr Glu Arg Val Leu Arg Ala Gly Arg Gln Leu His Gln
    50                  55                  60

His Leu Leu Ala Thr Cys Pro Asn Leu Ile Arg Asp Arg Lys Tyr His
65                  70                  75                  80

Leu Arg Leu Tyr Arg Gln Cys Cys Ser Gly Arg Glu Leu Val Asp Gly
                85                  90                  95

Ile Leu Ala Leu Gly Leu Gly Val His Ser Arg Ser Gln Val Val Gly
            100                 105                 110

Ile Cys Gln Val Leu Leu Asp Glu Gly Ala Leu Cys His Val Lys His
        115                 120                 125

Asp Trp Ala Phe Gln Asp Arg Asp Ala Gln Phe Tyr Arg Phe Pro Gly
    130                 135                 140

Pro Glu Pro Glu Pro Val Gly Thr His Glu Met Glu Glu Glu Leu Ala
145                 150                 155                 160

Glu Ala Val Ala Leu Leu Ser Gln Arg Gly Pro Asp Ala Leu Leu Thr
                165                 170                 175

Val Ala Leu Arg Lys Pro Pro Gly Gln Arg Thr Asp Glu Glu Leu Asp
            180                 185                 190

Leu Ile Phe Glu Glu Leu Leu His Ile Lys Ala Val Ala His Leu Ser
        195                 200                 205

Asn Ser Val Lys Arg Glu Leu Ala Ala Val Leu Leu Phe Glu Pro His
    210                 215                 220

Ser Lys Ala Gly Thr Val Leu Phe Ser Gln Gly Asp Lys Gly Thr Ser
225                 230                 235                 240

Trp Tyr Ile Ile Trp Lys Gly Ser Val Asn Val Thr His Gly Lys
                245                 250                 255

Gly Leu Val Thr Thr Leu His Glu Gly Asp Asp Phe Gly Gln Leu Ala
            260                 265                 270

Leu Val Asn Asp Ala Pro Arg Ala Ala Thr Ile Ile Leu Arg Glu Tyr
        275                 280                 285

Asn Cys His Phe Leu Arg Val Asp Lys Gln Asp Phe Asn Arg Ile Ile
```

```
                   290                   295                   300
Lys Asp Val Glu Ala Lys Thr Met Arg Leu Glu His Gly Lys Val
305                 310                 315                 320

Val Leu Val Leu Glu Arg Ala Ser Gln Gly Ala Gly Pro Ser Arg Pro
                    325                 330                 335

Pro Thr Pro Gly Arg Asn Arg Tyr Thr Val Met Ser Gly Thr Pro Asp
                340                 345                 350

Lys Ile Leu Glu Leu Leu Glu Ala Met Gly Leu Asp Ser Ser Ala
            355                 360                 365

His Asp Pro Lys Glu Thr Phe Leu Ser Asp Phe Leu Thr His Arg
    370                 375                 380

Val Phe Met Pro Ser Ala Gln Leu Cys Ala Ala Leu Leu His His Phe
385                 390                 395                 400

His Val Glu Pro Ala Gly Gly Ser Glu Gln Glu Arg Ser Thr Tyr Val
                405                 410                 415

Cys Asn Lys Arg Gln Gln Ile Leu Arg Leu Val Ser Gln Trp Val Ala
                420                 425                 430

Leu Tyr Gly Ser Met Leu His Thr Asp Pro Val Ala Thr Ser Phe Leu
            435                 440                 445

Gln Lys Leu Ser Asp Leu Val Gly Arg Asp Thr Arg Leu Ser Asn Leu
    450                 455                 460

Leu Arg Glu Gln Trp Pro Glu Arg Arg Arg Cys His Arg Leu Glu Asn
465                 470                 475                 480

Gly Cys Gly Asn Ala Ser Pro Gln Met Lys Val Ser Ala Trp Pro Gln
                485                 490                 495

Phe Leu Ser Ser Ala Pro Pro Gly Leu Gln Ala Pro Ser Pro Pro
                500                 505                 510

Asp Pro Glu Gly Leu Cys Gly Arg Gly Lys Leu Ser Ser His Arg His
            515                 520                 525

Thr Leu Gly Ser Leu Ile Gly Val His Gly Ala Leu Ala Ala Cys Gly
    530                 535                 540

Ala Leu Gly Gln Ala Val Pro Gly Gly Ala Glu Ala
545                 550                 555
```

<210> SEQ ID NO 15
<211> LENGTH: 1966
<212> TYPE: DNA
<213> ORGANISM: Rattus norvegicus
<220> FEATURE:
<221> NAME/KEY: CDS
<222> LOCATION: (3)..(875)

<400> SEQUENCE: 15

```
aa ggt gtg ctc aaa cct aat gat gtt tca gta ttt acg acg ctc acc        47
   Gly Val Leu Lys Pro Asn Asp Val Ser Val Phe Thr Thr Leu Thr
     1               5                  10                  15 att aat gga cgc ctg ttt gcc tgc ccg cga gag caa ttc gac tca ctg       95
Ile Asn Gly Arg Leu Phe Ala Cys Pro Arg Glu Gln Phe Asp Ser Leu
                 20                  25                  30 act ccc ttg cca gaa cag gag ggc ccg acc act ggg aca gtg ggg acg      143
Thr Pro Leu Pro Glu Gln Glu Gly Pro Thr Thr Gly Thr Val Gly Thr
             35                  40                  45 ttt gaa ctg atg agc tcg aaa gac ttg gcg tac cag atg aca acg tat      191
Phe Glu Leu Met Ser Ser Lys Asp Leu Ala Tyr Gln Met Thr Thr Tyr
         50                  55                  60 gac tgg gaa ctc ttc aac tgt gtg ctc gag ctg gag cta atc tac cac      239
Asp Trp Glu Leu Phe Asn Cys Val Leu Glu Leu Glu Leu Ile Tyr His
     65                  70                  75
```

```
           65                  70                  75
aca ttt gga agg cat aat ttt aaa aag acc aca gca aac ttg gat ttg      287
Thr Phe Gly Arg His Asn Phe Lys Lys Thr Thr Ala Asn Leu Asp Leu
 80                  85                  90                  95 ttc ctg agg aga ttt aat gaa att cag ttt tgg gtt gtc act gag atc      335
Phe Leu Arg Arg Phe Asn Glu Ile Gln Phe Trp Val Val Thr Glu Ile
                    100                 105                 110 tgc ctt tgt tcc cag ctc agc aag cgt gtt cag ctt ttg aaa aaa tgt      383
Cys Leu Cys Ser Gln Leu Ser Lys Arg Val Gln Leu Leu Lys Lys Cys
                115                 120                 125 atc aag ata gcg gct cac tgc aag gag tac aaa aac ttg aat tcc ttc      431
Ile Lys Ile Ala Ala His Cys Lys Glu Tyr Lys Asn Leu Asn Ser Phe
            130                 135                 140 ttc ggc atc gtc atg ggg ctc agt aac gtg gct gag agc cgc ctg gca      479
Phe Gly Ile Val Met Gly Leu Ser Asn Val Ala Glu Ser Arg Leu Ala
    145                 150                 155 tta aca tgg gag aaa ctg ccg agc aag ttt aag aag ttc tat gcg gag      527
Leu Thr Trp Glu Lys Leu Pro Ser Lys Phe Lys Lys Phe Tyr Ala Glu
160                 165                 170                 175 ttt gag agc tta atg gat cct tcc aga aat cac aag gcg tac agg ctg      575
Phe Glu Ser Leu Met Asp Pro Ser Arg Asn His Lys Ala Tyr Arg Leu
                    180                 185                 190 aca gca gct aaa ctg gag ccc ccc ctc atc cct ttc atg ccc ttg ctt      623
Thr Ala Ala Lys Leu Glu Pro Pro Leu Ile Pro Phe Met Pro Leu Leu
                195                 200                 205 att aaa gat atg aca ttt act cat gag ggg aac aag aca ttc att gac      671
Ile Lys Asp Met Thr Phe Thr His Glu Gly Asn Lys Thr Phe Ile Asp
            210                 215                 220 aat cta gta aac ttt gaa aaa atg cgc atg att gca aat act gcc aga      719
Asn Leu Val Asn Phe Glu Lys Met Arg Met Ile Ala Asn Thr Ala Arg
    225                 230                 235 acg gtg cgc tac tac agg agc cag cca ttc aat ccg gat gct gct caa      767
Thr Val Arg Tyr Tyr Arg Ser Gln Pro Phe Asn Pro Asp Ala Ala Gln
240                 245                 250                 255 gct aat aag aac cat cag gat gtc cgg agt tat gta cgg caa tta aat      815
Ala Asn Lys Asn His Gln Asp Val Arg Ser Tyr Val Arg Gln Leu Asn
                    260                 265                 270 gtg att gac aac cag aga act tta tca cag atg tca cac aga tta gag      863
Val Ile Asp Asn Gln Arg Thr Leu Ser Gln Met Ser His Arg Leu Glu
                275                 280                 285 cct cgc agg cca tagacatctg cagtgcccag agtgatgctc cgtctccagt          915
Pro Arg Arg Pro
            290 ccacaatctt tcaaaagatg ctgtgtatgc tactactgac tgtgttgcta ctagagaatt    975 ccccagaatg agcaagagac acctcctgag agccctcgg ggccacatcc tgctttccga    1035 ccacacagga gaaggatctg tcttgtctaa cgcggacatg ccgtagctta ggaaccatca   1095 gctgtagtca tcttcttcac ggttggcaca ccaccgcagg ctcacgtgaa gcataacctt   1155 ggcgaggcta caccaggccc ctgacatccc ttcccaggct gttgcagcat gagactgtcc   1215 cgtggatagg tttgacttgg aatcgctgca atgatataat tgaatgattt gtttacttag   1275 caccttattt ggggtctggg ttctggggag ggtgttgacc ataaaagtcc aaattatcca   1335 tcatgttcct ccatcgtcat aatcttacct ctgaaggaat ggaacctcat cacaacacta   1395 tgaaacatta tgactgttca gtctgtaatt tcggaatgat ctatagaata atatgtttac   1455 attgtaactt ttaaaaactt acaaatcagg attacacaca tgagaattcc actaagaaac   1515 accaaggttc ttaatatcgc cagcgttaag atagaaagta acatttcaga agagcacaat   1575
```

```
atacacaaaa catttttca aattgaaata ttttcctggg cattaaaaaa cctttccact    1635
acaaatttat tgttactgat gaaaaaaaaa gcatattttc tggacttaaa tgttattaca    1695
aaaatcttaa ttttcagcaa ttgttttgca ctttcagata gattgtaaat aggttatgca    1755
gtcaatggta tagaattatt tatttgctac ataatagaca ttgtgccaaa taattccttt    1815
ttatttattt tattcagtat gaaattttgg agtacatttt ttctgttttc ttaattagac    1875
tacatttaat gtataggaat tgtatgtaca tatctcttct gtaaataaca gccagtatct    1935
tcattaaata tacttgacaa gaaaaaaaaa a                                   1966
```

<210> SEQ ID NO 16
<211> LENGTH: 291
<212> TYPE: PRT
<213> ORGANISM: Rattus norvegicus

<400> SEQUENCE: 16

```
Gly Val Leu Lys Pro Asn Asp Val Ser Val Phe Thr Thr Leu Thr Ile
1               5                   10                  15

Asn Gly Arg Leu Phe Ala Cys Pro Arg Glu Gln Phe Asp Ser Leu Thr
            20                  25                  30

Pro Leu Pro Glu Gln Glu Gly Pro Thr Thr Gly Thr Val Gly Thr Phe
        35                  40                  45

Glu Leu Met Ser Ser Lys Asp Leu Ala Tyr Gln Met Thr Thr Tyr Asp
    50                  55                  60

Trp Glu Leu Phe Asn Cys Val Leu Glu Leu Glu Leu Ile Tyr His Thr
65                  70                  75                  80

Phe Gly Arg His Asn Phe Lys Lys Thr Thr Ala Asn Leu Asp Leu Phe
                85                  90                  95

Leu Arg Arg Phe Asn Glu Ile Gln Phe Trp Val Val Thr Glu Ile Cys
            100                 105                 110

Leu Cys Ser Gln Leu Ser Lys Arg Val Gln Leu Leu Lys Lys Cys Ile
        115                 120                 125

Lys Ile Ala Ala His Cys Lys Glu Tyr Lys Asn Leu Asn Ser Phe Phe
    130                 135                 140

Gly Ile Val Met Gly Leu Ser Asn Val Ala Glu Ser Arg Leu Ala Leu
145                 150                 155                 160

Thr Trp Glu Lys Leu Pro Ser Lys Phe Lys Lys Phe Tyr Ala Glu Phe
                165                 170                 175

Glu Ser Leu Met Asp Pro Ser Arg Asn His Lys Ala Tyr Arg Leu Thr
            180                 185                 190

Ala Ala Lys Leu Glu Pro Pro Leu Ile Pro Phe Met Pro Leu Leu Ile
        195                 200                 205

Lys Asp Met Thr Phe Thr His Glu Gly Asn Lys Thr Phe Ile Asp Asn
    210                 215                 220

Leu Val Asn Phe Glu Lys Met Arg Met Ile Ala Asn Thr Ala Arg Thr
225                 230                 235                 240

Val Arg Tyr Tyr Arg Ser Gln Pro Phe Asn Pro Asp Ala Ala Gln Ala
                245                 250                 255

Asn Lys Asn His Gln Asp Val Arg Ser Tyr Val Arg Gln Leu Asn Val
            260                 265                 270

Ile Asp Asn Gln Arg Thr Leu Ser Gln Met Ser His Arg Leu Glu Pro
        275                 280                 285

Arg Arg Pro
    290
```

```
<210> SEQ ID NO 17
<211> LENGTH: 3013
<212> TYPE: DNA
<213> ORGANISM: Homo sapiens
<220> FEATURE:
<221> NAME/KEY: CDS
<222> LOCATION: (407)..(2953)

<400> SEQUENCE: 17
gatccagcga agatgtggat ataatcttca ctcgactgaa agaagttaaa gcttttgaga      60
aatttcaccc aaatctcctt catcagattt gcttatgtgg ttattatgag aatctggaaa     120
agggaataac attatttcgc cagggtgata tggaacaaac tggtatgctg cctggcaggg     180
tctttggatg ttaaagtatc tgagaccagc agtcaccagg atgctgtgac catctgtacc     240
ctgggaattg ggacggcctt tggagagtcc attctggaca acacaccccg ccatgcaacc     300
atcgttacca gggagagcag tgaactgctc cgcatcgagc agaaggactt caaggcacta     360
tgggagaaat atcgacagta tatggcagga cttctggctc ctccctt atg gta tta      415
                                                    Met Val Leu
                                                      1 tgg aaa cgg gct cta aca atg aca gga ttc ctg aca agg aga aca cac       463
Trp Lys Arg Ala Leu Thr Met Thr Gly Phe Leu Thr Arg Arg Thr His
  5                  10                  15 ctc att gaa cct cac gtt cct ctt cgt cct gct aac acc att acc aag       511
Leu Ile Glu Pro His Val Pro Leu Arg Pro Ala Asn Thr Ile Thr Lys
 20                  25                  30                  35 gtc cct tca gag aag atc ctc aga gct gga aaa att tta cga aat gcc       559
Val Pro Ser Glu Lys Ile Leu Arg Ala Gly Lys Ile Leu Arg Asn Ala
                 40                  45                  50 att ctc tct cga gca cct cac atg ata aga gat aga aaa tac cac cta       607
Ile Leu Ser Arg Ala Pro His Met Ile Arg Asp Arg Lys Tyr His Leu
             55                  60                  65 aag aca tac aga caa tgc tgt gtg gga act gaa ctg gtg gac tgg atg       655
Lys Thr Tyr Arg Gln Cys Cys Val Gly Thr Glu Leu Val Asp Trp Met
         70                  75                  80 atc gac gag aca cca tgt gtt cac tcc cgg act caa gct gtt ggc atg       703
Ile Asp Glu Thr Pro Cys Val His Ser Arg Thr Gln Ala Val Gly Met
 85                  90                  95 tgg caa gtc ctg tta gaa gat ggt gtt ctc aac cac gtg gac cag gag       751
Trp Gln Val Leu Leu Glu Asp Gly Val Leu Asn His Val Asp Gln Glu
100                 105                 110                 115 cac cat ttc caa gac ttt tat tta ttc tat cga ttt ctg gat gat gag       799
His His Phe Gln Asp Phe Tyr Leu Phe Tyr Arg Phe Leu Asp Asp Glu
                120                 125                 130 cac gag gat gcc cct ttg cct act gag gag gag aag aag gag tgt gat       847
His Glu Asp Ala Pro Leu Pro Thr Glu Glu Glu Lys Lys Glu Cys Asp
            135                 140                 145 gag gag ctc cag gac acc atg ctg ctg ctg tca cag atg ggc ccc gac       895
Glu Glu Leu Gln Asp Thr Met Leu Leu Leu Ser Gln Met Gly Pro Asp
        150                 155                 160 gcc cac atg agg atg atc ctt cgc aaa cca cct ggc cag agg act gtg       943
Ala His Met Arg Met Ile Leu Arg Lys Pro Pro Gly Gln Arg Thr Val
    165                 170                 175 gat gac cta gag att atc tat gag gag ctt ctt cat att aaa gcc tta       991
Asp Asp Leu Glu Ile Ile Tyr Glu Glu Leu Leu His Ile Lys Ala Leu
180                 185                 190                 195 tcc cat ctt tct acc aca gtg aaa cga gag tta gca ggt gtt ctc att      1039
Ser His Leu Ser Thr Thr Val Lys Arg Glu Leu Ala Gly Val Leu Ile
                200                 205                 210
```

-continued

| | | |
|---|---|---|
| ttt gag tct cac gcc aaa gga ggg act gtg ttg ttt aac cag ggg gaa<br>Phe Glu Ser His Ala Lys Gly Gly Thr Val Leu Phe Asn Gln Gly Glu<br>215 220 225 | 1087 | |
| gaa ggt acc tcc tgg tac att att cta aaa gga tca gtg aat gta gtc<br>Glu Gly Thr Ser Trp Tyr Ile Ile Leu Lys Gly Ser Val Asn Val Val<br>230 235 240 | 1135 | |
| att tac ggc aag ggt gtg gtc tgc acc ctg cat gaa gga gat gac ttc<br>Ile Tyr Gly Lys Gly Val Val Cys Thr Leu His Glu Gly Asp Asp Phe<br>245 250 255 | 1183 | |
| ggc aag tta gca cta gtg aat gat gcc cca cga gct gcc tct atc gtc<br>Gly Lys Leu Ala Leu Val Asn Asp Ala Pro Arg Ala Ala Ser Ile Val<br>260 265 270 275 | 1231 | |
| tta cga gaa gat aac tgc cat ttc tta aga gta gac aag gag gat ttc<br>Leu Arg Glu Asp Asn Cys His Phe Leu Arg Val Asp Lys Glu Asp Phe<br>280 285 290 | 1279 | |
| aac cgg atc cta agg gac gtg gag gcg aat aca gtc aga ctt aaa gaa<br>Asn Arg Ile Leu Arg Asp Val Glu Ala Asn Thr Val Arg Leu Lys Glu<br>295 300 305 | 1327 | |
| cat gac caa gat gtc ttg gtg ctg gag aag gtc cca gca ggg aac aga<br>His Asp Gln Asp Val Leu Val Leu Glu Lys Val Pro Ala Gly Asn Arg<br>310 315 320 | 1375 | |
| gct tct aat caa gga aac tca cag cct cag caa aag tat act gtg atg<br>Ala Ser Asn Gln Gly Asn Ser Gln Pro Gln Gln Lys Tyr Thr Val Met<br>325 330 335 | 1423 | |
| tca gga aca cct gaa aaa att tta gag cat ttt cta gaa aca ata cgc<br>Ser Gly Thr Pro Glu Lys Ile Leu Glu His Phe Leu Glu Thr Ile Arg<br>340 345 350 355 | 1471 | |
| ctt gag gca act tta aat gaa gca aca gat tct gtt tta aat gac ttt<br>Leu Glu Ala Thr Leu Asn Glu Ala Thr Asp Ser Val Leu Asn Asp Phe<br>360 365 370 | 1519 | |
| att atg atg cac tgt gtt ttt atg cca aat acc cag ctt tgc ccg gca<br>Ile Met Met His Cys Val Phe Met Pro Asn Thr Gln Leu Cys Pro Ala<br>375 380 385 | 1567 | |
| ctg gtg gcc cac tac cac gca cag cct tca caa ggt aca gaa cag gag<br>Leu Val Ala His Tyr His Ala Gln Pro Ser Gln Gly Thr Glu Gln Glu<br>390 395 400 | 1615 | |
| aaa atg gat tat gcc ctc aac aat aag agg cga gtc atc cgc ctg gtt<br>Lys Met Asp Tyr Ala Leu Asn Asn Lys Arg Arg Val Ile Arg Leu Val<br>405 410 415 | 1663 | |
| cta cag tgg gct gcc atg tat gga gac ctc ctg caa gag gat gac gta<br>Leu Gln Trp Ala Ala Met Tyr Gly Asp Leu Leu Gln Glu Asp Asp Val<br>420 425 430 435 | 1711 | |
| tct atg gcc ttc ctg gag gag ttt tat gta tct gta tca gat gat gcc<br>Ser Met Ala Phe Leu Glu Glu Phe Tyr Val Ser Val Ser Asp Asp Ala<br>440 445 450 | 1759 | |
| cgg atg att gct gcc ctc aag gag caa ctg cca gag ttg gag aag att<br>Arg Met Ile Ala Ala Leu Lys Glu Gln Leu Pro Glu Leu Glu Lys Ile<br>455 460 465 | 1807 | |
| gtc aag caa atc tca gaa gat gca aag gca cca caa aag aag cac aag<br>Val Lys Gln Ile Ser Glu Asp Ala Lys Ala Pro Gln Lys Lys His Lys<br>470 475 480 | 1855 | |
| gtt ctt ttg caa cag ttc aat acg ggc gat gag aga gcc cag aag cgc<br>Val Leu Leu Gln Gln Phe Asn Thr Gly Asp Glu Arg Ala Gln Lys Arg<br>485 490 495 | 1903 | |
| cag cct atc cgc ggc tct gat gaa gtt ctg ttt aag gtc tat tgc atg<br>Gln Pro Ile Arg Gly Ser Asp Glu Val Leu Phe Lys Val Tyr Cys Met<br>500 505 510 515 | 1951 | |
| gac cac acc tac aca acc att cgg gtg cca gtg gcc act tcg gtg aag<br>Asp His Thr Tyr Thr Thr Ile Arg Val Pro Val Ala Thr Ser Val Lys | 1999 | |

```
                    520                 525                 530
gaa gtc atc agt gca gtt gcc gac aag ctg ggc tcc ggg gag ggc ctg       2047
Glu Val Ile Ser Ala Val Ala Asp Lys Leu Gly Ser Gly Glu Gly Leu
            535                 540                 545 atc ata gtc aag atg agt tcc gga gga gaa aag gtg gtc ctc aaa cct       2095
Ile Ile Val Lys Met Ser Ser Gly Gly Glu Lys Val Val Leu Lys Pro
        550                 555                 560 aat gat gtt tca gta ttt acg acg ctc acc att aat gga cgc ctg ttt       2143
Asn Asp Val Ser Val Phe Thr Thr Leu Thr Ile Asn Gly Arg Leu Phe
565                 570                 575 gct tgc ccg cga gag caa ttc gat tca ctg act ccc tta cca gaa cag       2191
Ala Cys Pro Arg Glu Gln Phe Asp Ser Leu Thr Pro Leu Pro Glu Gln
580                 585                 590                 595 gaa ggc cca act gtt gga aca gtg gga act ttt gaa ctg atg agc tcc       2239
Glu Gly Pro Thr Val Gly Thr Val Gly Thr Phe Glu Leu Met Ser Ser
            600                 605                 610 aaa gat tta gca tac cag atg aca att tat gat tgg gaa ctc ttc aac       2287
Lys Asp Leu Ala Tyr Gln Met Thr Ile Tyr Asp Trp Glu Leu Phe Asn
        615                 620                 625 tgc gtg cat gag ctg gag cta atc tat cac aca ttt gga agg cat aat       2335
Cys Val His Glu Leu Glu Leu Ile Tyr His Thr Phe Gly Arg His Asn
    630                 635                 640 ttt aaa aag acc aca gca aac ttg gat ttg ttc ctg agg aga ttt aat       2383
Phe Lys Lys Thr Thr Ala Asn Leu Asp Leu Phe Leu Arg Arg Phe Asn
645                 650                 655 gaa att cag ttt tgg gtc gtc act gag atc tgc ctt tgt tct cag ctc       2431
Glu Ile Gln Phe Trp Val Val Thr Glu Ile Cys Leu Cys Ser Gln Leu
660                 665                 670                 675 agc aag cgt gtt cag cta tta aaa aaa ttt att aag ata gca gcc cac       2479
Ser Lys Arg Val Gln Leu Leu Lys Lys Phe Ile Lys Ile Ala Ala His
            680                 685                 690 tgt aag gag tat aaa aat ctg aat tcc ttt ttt gcc atc gtc atg gga       2527
Cys Lys Glu Tyr Lys Asn Leu Asn Ser Phe Phe Ala Ile Val Met Gly
        695                 700                 705 cta agt aac att gct gtg agc cgc ttg gca cta acg tgg gag aaa ctg       2575
Leu Ser Asn Ile Ala Val Ser Arg Leu Ala Leu Thr Trp Glu Lys Leu
    710                 715                 720 cca agc aag ttc aag aag ttc tat gcg gag ttt gaa agt tta atg gac       2623
Pro Ser Lys Phe Lys Lys Phe Tyr Ala Glu Phe Glu Ser Leu Met Asp
725                 730                 735 cct tca agg aac cac agg gcc tac agg ctg aca gta gct aag ctg gaa       2671
Pro Ser Arg Asn His Arg Ala Tyr Arg Leu Thr Val Ala Lys Leu Glu
740                 745                 750                 755 cct cct ctc atc ccc ttc atg cct ttg ctc att aaa gat atg aca ttt       2719
Pro Pro Leu Ile Pro Phe Met Pro Leu Leu Ile Lys Asp Met Thr Phe
            760                 765                 770 act cat gag ggg aac aag acg ttc att gac aat cta gta aac ttt gaa       2767
Thr His Glu Gly Asn Lys Thr Phe Ile Asp Asn Leu Val Asn Phe Glu
        775                 780                 785 aaa atg cgc atg att gca aat acg gcc aga aca gtg aga tac tac agg       2815
Lys Met Arg Met Ile Ala Asn Thr Ala Arg Thr Val Arg Tyr Tyr Arg
    790                 795                 800 agc caa ccc ttc aat cct gat gca gct caa gct aat aag aac cat cag       2863
Ser Gln Pro Phe Asn Pro Asp Ala Ala Gln Ala Asn Lys Asn His Gln
805                 810                 815 gat gtc cgg agt tat gta cgg caa tta aat gtg att gac aac cag aga       2911
Asp Val Arg Ser Tyr Val Arg Gln Leu Asn Val Ile Asp Asn Gln Arg
820                 825                 830                 835 act tta tca cag atg tca cac aga tta gag cct cgt cga cca               2953
Thr Leu Ser Gln Met Ser His Arg Leu Glu Pro Arg Arg Pro
```

-continued

```
Thr Leu Ser Gln Met Ser His Arg Leu Glu Pro Arg Arg Pro
                840                 845 tagacatttc aaatgcccaa agcaacagtt tgtctccagt ccacaatttt caaaaatgcc    3013

<210> SEQ ID NO 18
<211> LENGTH: 849
<212> TYPE: PRT
<213> ORGANISM: Homo sapiens

<400> SEQUENCE: 18

Met Val Leu Trp Lys Arg Ala Leu Thr Met Thr Gly Phe Leu Thr Arg
1               5                   10                  15

Arg Thr His Leu Ile Glu Pro His Val Pro Leu Arg Pro Ala Asn Thr
            20                  25                  30

Ile Thr Lys Val Pro Ser Glu Lys Ile Leu Arg Ala Gly Lys Ile Leu
        35                  40                  45

Arg Asn Ala Ile Leu Ser Arg Ala Pro His Met Ile Arg Asp Arg Lys
    50                  55                  60

Tyr His Leu Lys Thr Tyr Arg Gln Cys Cys Val Gly Thr Glu Leu Val
65                  70                  75                  80

Asp Trp Met Ile Asp Glu Thr Pro Cys Val His Ser Arg Thr Gln Ala
                85                  90                  95

Val Gly Met Trp Gln Val Leu Leu Glu Asp Gly Val Leu Asn His Val
            100                 105                 110

Asp Gln Glu His His Phe Gln Asp Phe Tyr Leu Phe Tyr Arg Phe Leu
        115                 120                 125

Asp Asp Glu His Glu Asp Ala Pro Leu Pro Thr Glu Glu Lys Lys
    130                 135                 140

Glu Cys Asp Glu Glu Leu Gln Asp Thr Met Leu Leu Ser Gln Met
145                 150                 155                 160

Gly Pro Asp Ala His Met Arg Met Ile Leu Arg Lys Pro Pro Gly Gln
                165                 170                 175

Arg Thr Val Asp Asp Leu Glu Ile Ile Tyr Glu Glu Leu Leu His Ile
            180                 185                 190

Lys Ala Leu Ser His Leu Ser Thr Thr Val Lys Arg Glu Leu Ala Gly
        195                 200                 205

Val Leu Ile Phe Glu Ser His Ala Lys Gly Gly Thr Val Leu Phe Asn
    210                 215                 220

Gln Gly Glu Gly Thr Ser Trp Tyr Ile Ile Leu Lys Gly Ser Val
225                 230                 235                 240

Asn Val Val Ile Tyr Gly Lys Gly Val Val Cys Thr Leu His Glu Gly
                245                 250                 255

Asp Asp Phe Gly Lys Leu Ala Leu Val Asn Asp Ala Pro Arg Ala Ala
            260                 265                 270

Ser Ile Val Leu Arg Glu Asp Asn Cys His Phe Leu Arg Val Asp Lys
        275                 280                 285

Glu Asp Phe Asn Arg Ile Leu Arg Asp Val Glu Ala Asn Thr Val Arg
    290                 295                 300

Leu Lys Glu His Asp Gln Asp Val Leu Val Leu Glu Lys Val Pro Ala
305                 310                 315                 320

Gly Asn Arg Ala Ser Asn Gln Gly Asn Ser Gln Pro Gln Gln Lys Tyr
                325                 330                 335

Thr Val Met Ser Gly Thr Pro Glu Lys Ile Leu Glu His Phe Leu Glu
            340                 345                 350
```

-continued

```
Thr Ile Arg Leu Glu Ala Thr Leu Asn Glu Ala Thr Asp Ser Val Leu
        355                 360                 365

Asn Asp Phe Ile Met Met His Cys Val Phe Met Pro Asn Thr Gln Leu
370                 375                 380

Cys Pro Ala Leu Val Ala His Tyr His Ala Gln Pro Ser Gln Gly Thr
385                 390                 395                 400

Glu Gln Glu Lys Met Asp Tyr Ala Leu Asn Asn Lys Arg Arg Val Ile
            405                 410                 415

Arg Leu Val Leu Gln Trp Ala Ala Met Tyr Gly Asp Leu Leu Gln Glu
        420                 425                 430

Asp Val Ser Met Ala Phe Leu Glu Glu Phe Tyr Val Ser Val Ser
        435                 440                 445

Asp Asp Ala Arg Met Ile Ala Ala Leu Lys Glu Gln Leu Pro Glu Leu
450                 455                 460

Glu Lys Ile Val Lys Gln Ile Ser Glu Asp Ala Lys Ala Pro Gln Lys
465                 470                 475                 480

Lys His Lys Val Leu Leu Gln Gln Phe Asn Thr Gly Asp Glu Arg Ala
            485                 490                 495

Gln Lys Arg Gln Pro Ile Arg Gly Ser Asp Glu Val Leu Phe Lys Val
        500                 505                 510

Tyr Cys Met Asp His Thr Tyr Thr Thr Ile Arg Val Pro Val Ala Thr
        515                 520                 525

Ser Val Lys Glu Val Ile Ser Ala Val Ala Asp Lys Leu Gly Ser Gly
        530                 535                 540

Glu Gly Leu Ile Ile Val Lys Met Ser Ser Gly Glu Lys Val Val
545                 550                 555                 560

Leu Lys Pro Asn Asp Val Ser Val Phe Thr Thr Leu Thr Ile Asn Gly
                565                 570                 575

Arg Leu Phe Ala Cys Pro Arg Glu Gln Phe Asp Ser Leu Thr Pro Leu
            580                 585                 590

Pro Glu Gln Glu Gly Pro Thr Val Gly Thr Val Gly Thr Phe Glu Leu
        595                 600                 605

Met Ser Ser Lys Asp Leu Ala Tyr Gln Met Thr Ile Tyr Asp Trp Glu
        610                 615                 620

Leu Phe Asn Cys Val His Glu Leu Glu Leu Ile Tyr His Thr Phe Gly
625                 630                 635                 640

Arg His Asn Phe Lys Lys Thr Thr Ala Asn Leu Asp Leu Phe Leu Arg
                645                 650                 655

Arg Phe Asn Glu Ile Gln Phe Trp Val Val Thr Glu Ile Cys Leu Cys
            660                 665                 670

Ser Gln Leu Ser Lys Arg Val Gln Leu Leu Lys Lys Phe Ile Lys Ile
        675                 680                 685

Ala Ala His Cys Lys Glu Tyr Lys Asn Leu Asn Ser Phe Phe Ala Ile
        690                 695                 700

Val Met Gly Leu Ser Asn Ile Ala Val Ser Arg Leu Ala Leu Thr Trp
705                 710                 715                 720

Glu Lys Leu Pro Ser Lys Phe Lys Lys Phe Tyr Ala Glu Phe Glu Ser
                725                 730                 735

Leu Met Asp Pro Ser Arg Asn His Arg Ala Tyr Arg Leu Thr Val Ala
            740                 745                 750

Lys Leu Glu Pro Pro Leu Ile Pro Phe Met Pro Leu Leu Ile Lys Asp
        755                 760                 765

Met Thr Phe Thr His Glu Gly Asn Lys Thr Phe Ile Asp Asn Leu Val
```

```
                770                 775                 780
Asn Phe Glu Lys Met Arg Met Ile Ala Asn Thr Ala Arg Thr Val Arg
785                 790                 795                 800

Tyr Tyr Arg Ser Gln Pro Phe Asn Pro Asp Ala Ala Gln Ala Asn Lys
                805                 810                 815

Asn His Gln Asp Val Arg Ser Tyr Val Arg Gln Leu Asn Val Ile Asp
            820                 825                 830

Asn Gln Arg Thr Leu Ser Gln Met Ser His Arg Leu Glu Pro Arg Arg
        835                 840                 845

Pro

<210> SEQ ID NO 19
<211> LENGTH: 24
<212> TYPE: PRT
<213> ORGANISM: Caenorhabditis elegans

<400> SEQUENCE: 19

Phe Val Gln Ala Ser Pro Ser Asp Ile Ser Thr Ser Leu Ser His Ile
1               5                   10                  15

Asp Tyr Arg Val Leu Ser Arg Ile
            20

<210> SEQ ID NO 20
<211> LENGTH: 43
<212> TYPE: PRT
<213> ORGANISM: Caenorhabditis elegans

<400> SEQUENCE: 20

Arg Ala Glu Ile Leu Val Lys Phe Val His Val Ala Lys His Leu Arg
1               5                   10                  15

Lys Ile Asn Asn Phe Asn Thr Leu Met Ser Val Val Gly Gly Ile Thr
            20                  25                  30

His Ser Ser Val Ala Arg Leu Ala Lys Thr Tyr
        35                  40

<210> SEQ ID NO 21
<211> LENGTH: 22
<212> TYPE: PRT
<213> ORGANISM: Caenorhabditis elegans

<400> SEQUENCE: 21

Phe Arg Ile Pro Ile Ile Gly Val His Leu Lys Asp Leu Val Ala Ile
1               5                   10                  15

Asn Cys Ser Gly Ala Asn
            20

<210> SEQ ID NO 22
<211> LENGTH: 24
<212> TYPE: PRT
<213> ORGANISM: Homo sapiens

<400> SEQUENCE: 22

Leu His Asp Phe His Ser His Glu Ile Ala Glu Gln Leu Thr Leu Leu
1               5                   10                  15

Asp Ala Glu Leu Phe Tyr Lys Ile
            20

<210> SEQ ID NO 23
<211> LENGTH: 41
<212> TYPE: PRT
```

<213> ORGANISM: Homo sapiens

<400> SEQUENCE: 23

Arg Glu Arg Leu Leu Leu Lys Phe Ile Lys Ile Met Lys His Leu Arg
1               5                   10                  15

Lys Leu Asn Asn Phe Asn Ser Tyr Leu Ala Ile Leu Ser Ala Leu Asp
            20                  25                  30

Ser Ala Pro Ile Arg Arg Leu Glu Trp
        35                  40

<210> SEQ ID NO 24
<211> LENGTH: 22
<212> TYPE: PRT
<213> ORGANISM: Homo sapiens

<400> SEQUENCE: 24

Pro Cys Ile Pro Tyr Leu Gly Leu Ile Leu Gln Asp Leu Thr Phe Val
1               5                   10                  15

His Leu Gly Asn Pro Asp
            20

<210> SEQ ID NO 25
<211> LENGTH: 24
<212> TYPE: PRT
<213> ORGANISM: Mus musculus

<400> SEQUENCE: 25

Leu Leu Asp Ile Asp Pro Tyr Thr Tyr Ala Thr Gln Leu Thr Val Leu
1               5                   10                  15

Glu His Asp Leu Tyr Leu Arg Ile
            20

<210> SEQ ID NO 26
<211> LENGTH: 43
<212> TYPE: PRT
<213> ORGANISM: Mus musculus

<400> SEQUENCE: 26

Arg Ser Lys Leu Thr Gln Tyr Phe Val Thr Val Ala Gln His Cys Lys
1               5                   10                  15

Glu Leu Asn Asn Phe Ser Ser Met Thr Ala Ile Val Ser Ala Leu Tyr
            20                  25                  30

Ser Ser Pro Ile Tyr Arg Leu Lys Lys Thr Trp
        35                  40

<210> SEQ ID NO 27
<211> LENGTH: 22
<212> TYPE: PRT
<213> ORGANISM: Mus musculus

<400> SEQUENCE: 27

Ala Cys Val Pro Phe Phe Gly Val Tyr Leu Ser Asp Leu Thr Phe Thr
1               5                   10                  15

Phe Val Gly Asn Pro Asp
            20

<210> SEQ ID NO 28
<211> LENGTH: 24
<212> TYPE: PRT
<213> ORGANISM: Rattus rattus

<400> SEQUENCE: 28

Phe Glu Asn His Ser Ala Met Glu Ile Ala Glu Gln Leu Thr Leu Leu
1               5                   10                  15

Asp His Leu Val Phe Lys Ser Ile
            20

<210> SEQ ID NO 29
<211> LENGTH: 43
<212> TYPE: PRT
<213> ORGANISM: Rattus rattus

<400> SEQUENCE: 29

Arg Ala Ser Thr Ile Glu Lys Trp Val Ala Val Ala Asp Ile Cys Arg
1               5                   10                  15

Cys Leu His Asn Tyr Asn Ala Val Leu Glu Ile Thr Ser Ser Ile Asn
            20                  25                  30

Arg Ser Ala Ile Phe Arg Leu Lys Lys Thr Trp
        35                  40

<210> SEQ ID NO 30
<211> LENGTH: 22
<212> TYPE: PRT
<213> ORGANISM: Rattus rattus

<400> SEQUENCE: 30

Pro Cys Val Pro Tyr Leu Gly Met Tyr Leu Thr Asp Leu Ala Phe Leu
1               5                   10                  15

Glu Glu Gly Thr Pro Asn
            20

<210> SEQ ID NO 31
<211> LENGTH: 24
<212> TYPE: PRT
<213> ORGANISM: Homo sapiens

<400> SEQUENCE: 31

Leu Leu Thr Leu His Pro Ile Glu Ile Ala Arg Gln Leu Thr Leu Leu
1               5                   10                  15

Glu Ser Asp Leu Tyr Arg Ala Val
            20

<210> SEQ ID NO 32
<211> LENGTH: 43
<212> TYPE: PRT
<213> ORGANISM: Homo sapiens

<400> SEQUENCE: 32

Arg Val Ala Val Val Ser Arg Ile Ile Glu Ile Leu Gln Val Phe Gln
1               5                   10                  15

Glu Leu Asn Asn Phe Asn Gly Val Leu Glu Val Val Ser Ala Met Asn
            20                  25                  30

Ser Ser Pro Val Tyr Arg Leu Asp Arg Thr Phe
        35                  40

<210> SEQ ID NO 33
<211> LENGTH: 23
<212> TYPE: PRT
<213> ORGANISM: Homo sapiens

<400> SEQUENCE: 33

Pro Pro Cys Val Pro Phe Phe Gly Ile Tyr Leu Thr Asn Ile Leu Lys
1               5                   10                  15

Thr Glu Glu Gly Asn Pro Glu
            20

<210> SEQ ID NO 34
<211> LENGTH: 24
<212> TYPE: PRT
<213> ORGANISM: Saccharomyces cerevisiae

<400> SEQUENCE: 34

Ala Leu Asn Val Ser Pro Trp Ser Leu Ala Lys Thr Leu Thr Leu Leu
1               5                   10                  15

Glu Ser Ser Leu Tyr Leu Asp Ile
            20

<210> SEQ ID NO 35
<211> LENGTH: 43
<212> TYPE: PRT
<213> ORGANISM: Saccharomyces cerevisiae

<400> SEQUENCE: 35

Gln Thr His Thr Ile Ser Tyr Trp Leu Gln Val Ala Leu Ala Cys Leu
1               5                   10                  15

Tyr Leu Arg Asn Leu Asn Ser Leu Ala Ser Ile Ile Thr Ser Leu Gln
            20                  25                  30

Asn His Ser Ile Glu Arg Leu Ser Leu Pro Ile
        35                  40

<210> SEQ ID NO 36
<211> LENGTH: 22
<212> TYPE: PRT
<213> ORGANISM: Saccharomyces cerevisiae

<400> SEQUENCE: 36

Pro Cys Val Pro Phe Thr Ser Leu Leu Ile Arg Asp Ile Thr Phe Ile
1               5                   10                  15

Arg Asp Gly Asn Asp Thr
            20

<210> SEQ ID NO 37
<211> LENGTH: 20
<212> TYPE: PRT
<213> ORGANISM: Caenorhabditis elegans

<400> SEQUENCE: 37

Ala Val Phe Lys His Tyr Asp His Asp Arg Asp Gly Phe Ile Ser Gln
1               5                   10                  15

Glu Glu Phe Gln
            20

<210> SEQ ID NO 38
<211> LENGTH: 20
<212> TYPE: PRT
<213> ORGANISM: Homo sapiens

<400> SEQUENCE: 38

Glu Ala Phe Ser Leu Phe Asp Lys Asp Gly Asp Gly Thr Ile Thr Thr
1               5                   10                  15

Lys Phe Leu Gly
            20

<210> SEQ ID NO 39

```
<211> LENGTH: 20
<212> TYPE: PRT
<213> ORGANISM: Homo sapiens

<400> SEQUENCE: 39

Leu Met Leu Lys Leu Phe Asp Ser Asn Asn Asp Gly Lys Leu Glu Leu
1               5                   10                  15

Thr Glu Met Ala
            20

<210> SEQ ID NO 40
<211> LENGTH: 20
<212> TYPE: PRT
<213> ORGANISM: Homo sapiens

<400> SEQUENCE: 40

Phe Ala Phe Arg Ile Tyr Asp Met Asp Lys Asp Gly Tyr Ile Ser Asn
1               5                   10                  15

Gly Glu Leu Phe
            20

<210> SEQ ID NO 41
<211> LENGTH: 20
<212> TYPE: PRT
<213> ORGANISM: Homo sapiens

<400> SEQUENCE: 41

Lys Val Phe His Met Leu Asp Lys Asp Lys Ser Gly Phe Ile Glu Glu
1               5                   10                  15

Asp Glu Leu Gly
            20

<210> SEQ ID NO 42
<211> LENGTH: 20
<212> TYPE: PRT
<213> ORGANISM: Homo sapiens

<400> SEQUENCE: 42

Glu Cys Phe Arg Ile Phe Asp Arg Lys Ala Asp Gly Tyr Ile Asp Pro
1               5                   10                  15

Glu Glu Leu Ala
            20

<210> SEQ ID NO 43
<211> LENGTH: 50
<212> TYPE: PRT
<213> ORGANISM: Caenorhabditis elegans

<400> SEQUENCE: 43

His Asn Phe His Glu Thr Thr Phe Leu Thr Pro Thr Thr Cys Asn His
1               5                   10                  15

Cys Asn Lys Leu Leu Trp Gly Ile Leu Arg Gln Gly Phe Lys Cys Lys
            20                  25                  30

Asp Cys Gly Leu Ala Val His Ser Cys Cys Lys Ser Asn Ala Val Ala
        35                  40                  45

Glu Cys
    50

<210> SEQ ID NO 44
<211> LENGTH: 50
<212> TYPE: PRT
<213> ORGANISM: Homo sapiens
```

-continued

```
<400> SEQUENCE: 44

His Lys Phe Ile Ala Arg Phe Phe Lys Gln Pro Thr Phe Cys Ser His
1               5                   10                  15

Cys Thr Asp Phe Ile Trp Gly Phe Gly Lys Gln Gly Phe Gln Cys Gln
                20                  25                  30

Val Cys Cys Phe Val Val His Lys Arg Cys His Glu Phe Val Thr Phe
            35                  40                  45

Ser Cys
    50

<210> SEQ ID NO 45
<211> LENGTH: 50
<212> TYPE: PRT
<213> ORGANISM: Homo sapiens

<400> SEQUENCE: 45

His Lys Phe Thr Ala Arg Phe Phe Lys Gln Pro Thr Phe Cys Ser His
1               5                   10                  15

Cys Thr Asp Phe Ile Trp Gly Phe Gly Lys Gln Gly Phe Gln Cys Gln
                20                  25                  30

Val Cys Cys Phe Val Val His Lys Arg Cys His Glu Phe Val Thr Phe
            35                  40                  45

Ser Cys
    50

<210> SEQ ID NO 46
<211> LENGTH: 50
<212> TYPE: PRT
<213> ORGANISM: Homo sapiens

<400> SEQUENCE: 46

His Lys Phe Thr Ala Arg Phe Phe Lys Gln Pro Thr Phe Cys Ser His
1               5                   10                  15

Cys Thr Asp Phe Ile Trp Gly Ile Gly Lys Gln Gly Leu Gln Cys Gln
                20                  25                  30

Val Cys Ser Phe Val Val His Arg Arg Cys His Glu Phe Val Thr Phe
            35                  40                  45

Glu Cys
    50

<210> SEQ ID NO 47
<211> LENGTH: 24
<212> TYPE: PRT
<213> ORGANISM: Caenorhabditis elegans

<400> SEQUENCE: 47

Leu His Leu Ile Asp Ser Gln Glu Leu Ala His Gln Leu Phe Leu Phe
1               5                   10                  15

His Leu Gln Leu Leu Arg Ser Thr
                20

<210> SEQ ID NO 48
<211> LENGTH: 43
<212> TYPE: PRT
<213> ORGANISM: Homo sapiens

<400> SEQUENCE: 48

Arg Val Gln Leu Leu Lys Lys Phe Ile Lys Ile Ala Ala His Cys Lys
1               5                   10                  15
```

-continued

Glu Tyr Lys Asn Leu Asn Ser Phe Phe Ala Ile Val Met Gly Leu Ser
            20                  25                  30

Asn Ile Ala Val Ser Arg Leu Ala Leu Thr Trp
        35                  40

<210> SEQ ID NO 49
<211> LENGTH: 43
<212> TYPE: PRT
<213> ORGANISM: Caenorhabditis elegans

<400> SEQUENCE: 49

Arg Met Glu Ile Leu Lys Lys Phe Ile Ser Ile Ala Thr Ile Ala Arg
1               5                   10                  15

Glu Tyr Arg Asp Leu Leu Thr Val Phe Ala Ile Thr Leu Gly Leu Ser
            20                  25                  30

Met Thr Ser Ile Ser Arg Leu Thr Leu Thr Trp
        35                  40

<210> SEQ ID NO 50
<211> LENGTH: 22
<212> TYPE: PRT
<213> ORGANISM: Caenorhabditis elegans

<400> SEQUENCE: 50

Pro Tyr Ile Pro Phe Val Pro Leu Ile Leu Lys Asp Leu Met Phe Ile
1               5                   10                  15

His Gln Gly Asn Lys Ser
            20

<210> SEQ ID NO 51
<211> LENGTH: 69
<212> TYPE: PRT
<213> ORGANISM: Caenorhabditis elegans

<400> SEQUENCE: 51

Val Phe Arg Gln Gly Glu Ile Gly Val Tyr Trp Tyr Ile Val Leu Lys
1               5                   10                  15

Gly Ala Val Glu Val Asn Val Asn Gly Lys Ile Val Cys Leu Leu Arg
            20                  25                  30

Glu Gly Asp Asp Phe Gly Lys Leu Ala Leu Val Asn Asp Leu Pro Arg
        35                  40                  45

Ala Ala Thr Ile Val Thr Tyr Glu Asp Asp Ser Met Phe Leu Val Val
    50                  55                  60

Asp Lys His His Phe
65

<210> SEQ ID NO 52
<211> LENGTH: 67
<212> TYPE: PRT
<213> ORGANISM: Homo sapiens

<400> SEQUENCE: 52

Val Ile Gln Gln Gly Asp Glu Gly Asp Asn Phe Tyr Val Ile Asp Gln
1               5                   10                  15

Gly Glu Thr Asp Val Tyr Val Asn Asn Glu Trp Ala Thr Val Gly Glu
            20                  25                  30

Gly Gly Ser Phe Gly Glu Leu Ala Leu Ile Tyr Gly Thr Pro Arg Ala
        35                  40                  45

Ala Thr Val Lys Ala Lys Thr Asn Val Lys Leu Trp Gly Ile Asp Arg

```
                  50                  55                  60

Asp Ser Tyr
 65

<210> SEQ ID NO 53
<211> LENGTH: 71
<212> TYPE: PRT
<213> ORGANISM: Homo sapiens

<400> SEQUENCE: 53

Val Ile Asp Gln Gly Asp Asp Gly Asp Asn Phe Tyr Val Ile Glu Arg
 1               5                  10                  15

Gly Thr Tyr Asp Ile Leu Val Thr Lys Asp Asn Gln Thr Arg Val Gly
                20                  25                  30

Gln Tyr Asp Asn Arg Gly Ser Phe Gly Glu Leu Ala Leu Met Tyr Asn
            35                  40                  45

Thr Pro Arg Ala Ala Thr Ile Val Ala Thr Ser Glu Gly Ser Leu Trp
        50                  55                  60

Gly Leu Asp Arg Val Thr Phe
 65                  70

<210> SEQ ID NO 54
<211> LENGTH: 73
<212> TYPE: PRT
<213> ORGANISM: Homo sapiens

<400> SEQUENCE: 54

Ile Val Val Gln Gly Glu Pro Gly Asp Glu Phe Phe Ile Ile Leu Glu
 1               5                  10                  15

Gly Ser Ala Ala Val Leu Gln Arg Arg Ser Glu Asn Glu Glu Phe Val
                20                  25                  30

Val Gly Arg Leu Gly Pro Ser Asp Tyr Phe Gly Glu Ile Ala Leu Leu
            35                  40                  45

Met Asn Arg Pro Arg Ala Ala Thr Val Val Ala Arg Gly Pro Leu Lys
        50                  55                  60

Cys Val Lys Leu Asp Arg Pro Arg Phe
 65                  70

<210> SEQ ID NO 55
<211> LENGTH: 79
<212> TYPE: PRT
<213> ORGANISM: Homo sapiens

<400> SEQUENCE: 55

Ile Ile Thr Gln Gly Glu Lys Ala Asp Ser Phe Tyr Ile Ile Glu Ser
 1               5                  10                  15

Gly Glu Val Ser Ile Leu Ile Arg Ser Arg Thr Lys Ser Asn Lys Asp
                20                  25                  30

Gly Gly Asn Gln Glu Val Glu Ile Ala Arg His Lys Gly Gln Tyr Phe
            35                  40                  45

Gly Glu Leu Ala Leu Val Thr Asn Lys Pro Arg Ala Ala Ser Ala Tyr
        50                  55                  60

Ala Val Gly Asp Val Lys Cys Leu Val Met Asp Val Gln Ala Phe
 65                  70                  75

<210> SEQ ID NO 56
<211> LENGTH: 67
<212> TYPE: PRT
<213> ORGANISM: Homo sapiens
```

-continued

```
<400> SEQUENCE: 56

Ile Ile Lys Glu Gly Asp Val Gly Ser Leu Val Tyr Val Met Glu Asp
1               5                   10                  15

Gly Lys Val Glu Val Thr Lys Glu Gly Val Lys Cys Thr Met Gly Pro
            20                  25                  30

Gly Lys Val Phe Gly Glu Leu Ala Ile Leu Tyr Asn Cys Thr Arg Thr
        35                  40                  45

Ala Thr Val Lys Thr Leu Val Asn Val Lys Leu Trp Ala Ile Asp Arg
    50                  55                  60

Gln Cys Phe
65

<210> SEQ ID NO 57
<211> LENGTH: 67
<212> TYPE: PRT
<213> ORGANISM: Homo sapiens

<400> SEQUENCE: 57

Ile Ile Lys Glu Gly Asp Val Gly Ser Leu Val Tyr Val Met Glu Asp
1               5                   10                  15

Gly Lys Val Glu Val Thr Lys Glu Gly Val Lys Cys Thr Met Gly Pro
            20                  25                  30

Gly Lys Val Phe Gly Glu Leu Ala Ile Leu Tyr Asn Cys Thr Arg Thr
        35                  40                  45

Ala Thr Val Lys Thr Leu Val Asn Val Lys Leu Trp Ala Ile Asp Arg
    50                  55                  60

Gln Cys Phe
65

<210> SEQ ID NO 58
<211> LENGTH: 67
<212> TYPE: PRT
<213> ORGANISM: Homo sapiens

<400> SEQUENCE: 58

Ile Ile Lys Gln Gly Glu Pro Gly Asn His Ile Phe Val Leu Ala Glu
1               5                   10                  15

Gly Arg Leu Glu Val Phe Gln Gly Lys Leu Leu Ser Ser Ile Pro Met
            20                  25                  30

Trp Thr Thr Phe Gly Glu Leu Ala Ile Leu Tyr Asn Cys Thr Arg Thr
        35                  40                  45

Ala Ser Val Lys Ala Ile Thr Asn Val Lys Thr Trp Ala Leu Asp Arg
    50                  55                  60

Glu Val Phe
65

<210> SEQ ID NO 59
<211> LENGTH: 1011
<212> TYPE: PRT
<213> ORGANISM: Homo sapiens

<400> SEQUENCE: 59

Met Val Ala Ala His Ala Ala His Ser Ser Ser Ser Ala Glu Trp Ile
1               5                   10                  15

Ala Cys Leu Asp Lys Arg Pro Leu Glu Arg Ser Ser Glu Asp Val Asp
            20                  25                  30

Ile Ile Phe Thr Arg Leu Lys Glu Val Lys Ala Phe Glu Lys Phe His
```

-continued

```
                35                  40                  45
Pro Asn Leu Leu His Gln Ile Cys Leu Cys Gly Tyr Tyr Glu Asn Leu
 50                  55                  60
Glu Lys Gly Ile Thr Leu Phe Arg Gln Gly Asp Ile Gly Thr Asn Trp
 65                  70                  75                  80
Tyr Ala Val Leu Ala Gly Ser Leu Asp Val Lys Val Ser Glu Thr Ser
                 85                  90                  95
Ser His Gln Asp Ala Val Thr Ile Cys Thr Leu Gly Ile Gly Thr Ala
                100                 105                 110
Phe Gly Glu Ser Ile Leu Asp Asn Thr Pro Arg His Ala Thr Ile Val
                115                 120                 125
Thr Arg Glu Ser Ser Glu Leu Leu Arg Ile Glu Gln Lys Asp Phe Lys
                130                 135                 140
Ala Leu Trp Glu Lys Tyr Arg Gln Tyr Met Ala Gly Leu Leu Ala Pro
145                 150                 155                 160
Pro Tyr Gly Val Met Glu Thr Gly Ser Asn Asn Asp Arg Ile Pro Asp
                165                 170                 175
Lys Glu Asn Thr Pro Leu Ile Glu Pro His Val Pro Leu Arg Pro Ala
                180                 185                 190
Asn Thr Ile Thr Lys Val Pro Ser Glu Lys Ile Leu Arg Ala Gly Lys
                195                 200                 205
Ile Leu Arg Asn Ala Ile Leu Ser Arg Ala Pro His Met Ile Arg Asp
                210                 215                 220
Arg Lys Tyr His Leu Lys Thr Tyr Arg Gln Cys Cys Val Gly Thr Glu
225                 230                 235                 240
Leu Val Asp Trp Met Met Gln Gln Thr Pro Cys Val His Ser Arg Thr
                245                 250                 255
Gln Ala Val Gly Met Trp Gln Val Leu Leu Glu Asp Gly Val Leu Asn
                260                 265                 270
His Val Asp Gln Glu His His Phe Gln Asp Lys Tyr Leu Phe Tyr Arg
                275                 280                 285
Phe Leu Asp Asp Glu His Glu Asp Ala Pro Leu Pro Thr Glu Glu Glu
                290                 295                 300
Lys Lys Glu Cys Asp Glu Glu Leu Gln Asp Thr Met Leu Leu Leu Ser
305                 310                 315                 320
Gln Met Gly Pro Asp Ala His Met Arg Met Ile Leu Arg Lys Pro Pro
                325                 330                 335
Gly Gln Arg Thr Val Asp Asp Leu Glu Ile Ile Tyr Glu Glu Leu Leu
                340                 345                 350
His Ile Lys Ala Leu Ser His Leu Ser Thr Thr Val Lys Arg Glu Leu
                355                 360                 365
Ala Gly Val Leu Ile Phe Glu Ser His Ala Lys Gly Gly Thr Val Leu
                370                 375                 380
Phe Asn Gln Gly Glu Glu Gly Thr Ser Trp Tyr Ile Ile Leu Lys Gly
385                 390                 395                 400
Ser Val Asn Val Val Ile Tyr Gly Lys Gly Val Val Cys Thr Leu His
                405                 410                 415
Glu Gly Asp Asp Phe Gly Lys Leu Ala Leu Val Asn Asp Ala Pro Arg
                420                 425                 430
Ala Ala Ser Ile Val Leu Arg Glu Asp Asn Cys His Phe Leu Arg Val
                435                 440                 445
Asp Lys Glu Asp Phe Asn Arg Ile Leu Arg Asp Val Glu Ala Asn Thr
                450                 455                 460
```

-continued

```
Val Arg Leu Lys Glu His Asp Gln Asp Val Leu Val Leu Lys Val
465                 470                 475                 480

Pro Ala Gly Asn Arg Ala Ser Asn Gln Gly Asn Ser Gln Pro Gln Gln
                485                 490                 495

Lys Tyr Thr Val Met Ser Gly Thr Pro Glu Lys Ile Leu Glu His Phe
                500                 505                 510

Leu Glu Thr Ile Arg Leu Glu Ala Thr Leu Asn Glu Ala Thr Asp Ser
                515                 520                 525

Val Leu Asn Asp Phe Ile Met Met His Cys Val Phe Met Pro Asn Thr
530                 535                 540

Gln Leu Cys Pro Ala Leu Val Ala His Tyr His Ala Gln Pro Ser Gln
545                 550                 555                 560

Gly Thr Glu Gln Glu Lys Met Asp Tyr Ala Leu Asn Asn Lys Arg Arg
                565                 570                 575

Val Ile Arg Leu Val Leu Gln Trp Ala Ala Met Tyr Gly Asp Leu Leu
                580                 585                 590

Gln Glu Asp Asp Val Ser Met Ala Phe Leu Glu Glu Phe Tyr Val Ser
                595                 600                 605

Val Ser Asp Asp Ala Arg Met Ile Ala Ala Leu Lys Glu Gln Leu Pro
610                 615                 620

Glu Leu Glu Lys Ile Val Lys Gln Ile Ser Glu Asp Ala Lys Ala Pro
625                 630                 635                 640

Gln Lys Lys His Lys Val Leu Leu Gln Gln Phe Asn Thr Gly Asp Glu
                645                 650                 655

Arg Ala Gln Lys Arg Gln Pro Ile Arg Gly Ser Asp Glu Val Leu Phe
                660                 665                 670

Lys Val Tyr Cys Met Asp His Thr Tyr Thr Ile Arg Val Pro Val
                675                 680                 685

Ala Thr Ser Val Lys Glu Val Ile Ser Ala Val Ala Asp Lys Leu Gly
690                 695                 700

Ser Gly Glu Gly Leu Ile Ile Val Lys Met Ser Ser Gly Gly Glu Lys
705                 710                 715                 720

Val Val Leu Lys Pro Asn Asp Val Ser Val Phe Thr Thr Leu Thr Ile
                725                 730                 735

Asn Gly Arg Leu Phe Ala Cys Pro Arg Glu Gln Phe Asp Ser Leu Thr
                740                 745                 750

Pro Leu Pro Glu Gln Glu Gly Pro Thr Val Gly Thr Val Gly Thr Phe
                755                 760                 765

Glu Leu Met Ser Ser Lys Asp Leu Ala Tyr Gln Met Thr Ile Tyr Asp
770                 775                 780

Trp Glu Leu Phe Asn Cys Val His Glu Leu Glu Leu Ile Tyr His Thr
785                 790                 795                 800

Phe Gly Arg His Asn Phe Lys Lys Thr Thr Ala Asn Leu Asp Leu Phe
                805                 810                 815

Leu Arg Arg Phe Asn Glu Ile Gln Phe Trp Val Val Thr Glu Ile Cys
                820                 825                 830

Leu Cys Ser Gln Leu Ser Lys Arg Val Gln Leu Leu Lys Lys Phe Ile
                835                 840                 845

Lys Ile Ala Ala His Cys Lys Glu Tyr Lys Asn Leu Asn Ser Phe Phe
850                 855                 860

Ala Ile Val Met Gly Leu Ser Asn Ile Ala Val Ser Arg Leu Ala Leu
865                 870                 875                 880
```

-continued

```
Thr Trp Glu Lys Leu Pro Ser Lys Phe Lys Phe Tyr Ala Glu Phe
                885                 890                 895

Glu Ser Leu Met Asp Pro Ser Arg Asn His Arg Ala Tyr Arg Leu Thr
            900                 905                 910

Val Ala Lys Leu Glu Pro Pro Leu Ile Pro Phe Met Pro Leu Leu Ile
        915                 920                 925

Lys Asp Met Thr Phe Thr His Glu Gly Asn Lys Thr Phe Ile Asp Asn
    930                 935                 940

Leu Val Asn Phe Glu Lys Met Arg Met Ile Ala Asn Thr Ala Arg Thr
945                 950                 955                 960

Val Arg Tyr Tyr Arg Ser Gln Pro Phe Asn Pro Asp Ala Ala Gln Ala
                965                 970                 975

Asn Lys Asn His Gln Asp Val Arg Ser Tyr Val Arg Gln Leu Asn Val
            980                 985                 990

Ile Asp Asn Gln Arg Thr Leu Ser  Gln Met Ser His Arg  Leu Glu Pro
        995                 1000                 1005

Arg Arg  Pro
    1010

<210> SEQ ID NO 60
<211> LENGTH: 20
<212> TYPE: PRT
<213> ORGANISM: Homo sapiens

<400> SEQUENCE: 60

Ser Val Phe Lys Asn Tyr Asp His Asp Gln Asp Gly Tyr Ile Ser Gln
1               5                   10                  15

Glu Glu Phe Glu
            20

<210> SEQ ID NO 61
<211> LENGTH: 50
<212> TYPE: PRT
<213> ORGANISM: Homo sapiens

<400> SEQUENCE: 61

His Asn Phe Gln Glu Thr Thr Tyr Leu Lys Pro Thr Phe Cys Asp Asn
1               5                   10                  15

Cys Ala Gly Phe Leu Trp Gly Val Ile Lys Gln Gly Tyr Arg Cys Lys
            20                  25                  30

Asp Cys Gly Met Asn Cys His Lys Gln Cys Lys Asp Leu Val Val Phe
        35                  40                  45

Glu Cys
    50

<210> SEQ ID NO 62
<211> LENGTH: 24
<212> TYPE: PRT
<213> ORGANISM: Rattus norvegicus

<400> SEQUENCE: 62

Phe Glu Leu Met Ser Ser Lys Asp Leu Ala Tyr Gln Met Thr Thr Tyr
1               5                   10                  15

Asp Trp Glu Leu Phe Asn Cys Val
            20

<210> SEQ ID NO 63
<211> LENGTH: 24
<212> TYPE: PRT
```

<213> ORGANISM: Homo sapiens

<400> SEQUENCE: 63

Phe Asp His Leu Glu Pro Glu Glu Leu Ser Glu His Phe Thr Tyr Leu
1               5                   10                  15

Glu Phe Lys Ser Phe Arg Arg Ile
            20

<210> SEQ ID NO 64
<211> LENGTH: 43
<212> TYPE: PRT
<213> ORGANISM: Rattus norvegicus

<400> SEQUENCE: 64

Arg Val Gln Leu Leu Lys Lys Cys Ile Lys Ile Ala Ala His Cys Lys
1               5                   10                  15

Glu Tyr Lys Asn Leu Asn Ser Phe Phe Gly Ile Val Met Gly Leu Ser
            20                  25                  30

Asn Val Ala Glu Ser Arg Leu Ala Leu Thr Trp
        35                  40

<210> SEQ ID NO 65
<211> LENGTH: 43
<212> TYPE: PRT
<213> ORGANISM: Homo sapiens

<400> SEQUENCE: 65

Arg Ala Glu Val Phe Ile Lys Phe Ile Gln Val Ala Gln Lys Leu His
1               5                   10                  15

Gln Leu Gln Asn Phe Asn Thr Leu Met Ala Val Ile Gly Gly Leu Cys
            20                  25                  30

His Ser Ser Ile Ser Arg Leu Lys Glu Thr Ser
        35                  40

<210> SEQ ID NO 66
<211> LENGTH: 22
<212> TYPE: PRT
<213> ORGANISM: Rattus norvegicus

<400> SEQUENCE: 66

Pro Leu Ile Pro Phe Met Pro Leu Leu Ile Lys Asp Met Thr Phe Thr
1               5                   10                  15

His Glu Gly Asn Lys Thr
            20

<210> SEQ ID NO 67
<211> LENGTH: 22
<212> TYPE: PRT
<213> ORGANISM: Homo sapiens

<400> SEQUENCE: 67

Phe Lys Ile Pro Ile Leu Gly Val His Leu Lys Asp Leu Ile Ser Leu
1               5                   10                  15

Tyr Glu Ala Met Pro Asp
            20

What is claimed is:

1. An isolated nucleic acid comprising a recombinant vector comprising a nucleotide sequence selected from the group consisting of nucleic acids 854 to 2953 of SEQ ID NO: 17, and a sequence complementary to nucleic acids 854 to 2953 of SEQ ID NO: 17.

2. An isolated nucleic acid as in claim 1 wherein said vector is an expression vector and said nucleotide sequence is operably joined to a regulatory region.

3. An isolated nucleic acid as in claim 2 wherein said expression vector is a mammalian expression vector.

4. An isolated nucleic acid as in claim 3 wherein said mammalian expression vector expresses said nucleotide sequence in cells in culture, said cells being selected from the group consisting of fibroblast, liver, kidney, spleen, bone marrow, and neurological cells.

5. An isolated nucleic acid as in claim 2 wherein said vector is selected from the group consisting of vaccinia virus, adenovirus, retrovirus, neurotropic viruses, and Herpes simplex virus.

6. An isolated nucleic acid comprising a recombinant expression vector comprising a nucleotide sequence selected from the group consisting of nucleic acids 854 to 2953 of SEQ ID NO: 17, and a sequence complementary to nucleic acids 854 to 2953 of SEQ ID NO: 17; said nucleotide sequence being operably joined to a regulatory region, wherein said expression vector encodes at least a functional domain of an hcAMP-GEFII protein having the amino acid sequence of amino acids 150 to 849 of SEQ ID NO: 18, wherein said functional domain of the hcAMP-GEFII protein exhibits guanine nucleotide exchange factor activity in an in vitro assay.

7. An isolated nucleic acid as in claim 2 wherein said vector further comprises sequences encoding an exogenous protein operably joined to said nucleotide sequence and whereby said vector encodes a fusion protein.

8. An isolated nucleic acid as in claim 7 wherein said exogenous protein is selected from the group consisting of lacZ, trpE, maltose-binding protein, poly-His tags, and glutathione-S-transferase.

9. A host cell in culture, or a descendent cell thereof in culture, said host cell or descendent cell comprising a recombinant vector of any one of claims 1, 2 or 5–8, wherein said host cell is transformed in vitro with said vector.

10. A host cell in culture as in claim 9 wherein said host cell is selected from the group consisting of bacterial cells and yeast cells.

11. A host cell in culture as in claim 9 wherein said host cell is a mammalian host cell.

12. A host cell in culture as in claim 9 wherein said cell is selected from the group consisting of fibroblast, liver, kidney, spleen, bone marrow and neurological cells.

13. A host cell in culture as in claim 9 wherein said cell is an invertebrate cell.

14. A method for producing at least a functional domain of an hcAMP-GEFII protein (SEQ ID NO: 18), said method comprising culturing a host cell of any one of claims 10–13 under suitable conditions to produce said protein by expressing said nucleic acid, wherein said functional domain exhibits guanine nucleotide exchange factor activity in an in vitro assay.

15. A host cell in culture, or a descendant cell thereof in culture, said host cell or descendent cell comprising an expression vector of claim 3 or 4, wherein said host cell is transformed in vitro with said expression vector.

16. A host cell in culture as in claim 15 wherein said host cell is a mammalian host cell.

17. A host cell in culture as in claim 15 wherein said cell is selected from the group consisting of fibroblast, liver, kidney, spleen, bone marrow and neurological cells.

18. A method for producing at least a functional domain of an hcAMP-GEFII protein (SEQ ID NO: 18), said method comprising culturing a host cell of claim 9 under suitable conditions to produce said protein by expressing said nucleic acid, wherein said functional domain exhibits guanine nucleotide exchange factor activity in an in vitro assay.

* * * * *